United States Patent
Currie et al.

(10) Patent No.: US 9,249,123 B2
(45) Date of Patent: Feb. 2, 2016

(54) PYRIDINONES/PYRAZINONES, METHOD OF MAKING, AND METHOD OF USE THEREOF

(75) Inventors: Kevin S. Currie, North Branford, CT (US); Xiaojing Wang, Foster City, CA (US); Wendy B. Young, San Mateo, CA (US)

(73) Assignees: Genentech, Inc., South San Francisco, CA (US); Gilead Connecticut, Inc., Foster City, CA (US)

( * ) Notice: Subject to any disclaimer, the term of this patent is extended or adjusted under 35 U.S.C. 154(b) by 414 days.

(21) Appl. No.: 13/819,864

(22) PCT Filed: Aug. 31, 2011

(86) PCT No.: PCT/US2011/050034
§ 371 (c)(1),
(2), (4) Date: Jun. 5, 2013

(87) PCT Pub. No.: WO2012/031004
PCT Pub. Date: Mar. 8, 2012

(65) Prior Publication Data
US 2013/0281432 A1 Oct. 24, 2013

Related U.S. Application Data

(60) Provisional application No. 61/379,044, filed on Sep. 1, 2010.

(51) Int. Cl.

| | | |
|---|---|---|
| *A61K 31/381* | (2006.01) | |
| *A61K 31/40* | (2006.01) | |
| *A61K 31/4015* | (2006.01) | |
| *A61K 31/425* | (2006.01) | |
| *A61K 31/435* | (2006.01) | |
| *A61K 31/495* | (2006.01) | |
| *C07D 401/14* | (2006.01) | |
| *A61K 31/497* | (2006.01) | |
| *C07D 401/10* | (2006.01) | |
| *C07D 403/14* | (2006.01) | |
| *C07D 413/14* | (2006.01) | |
| *C07D 487/04* | (2006.01) | |
| *C07D 495/04* | (2006.01) | |
| *C07D 513/04* | (2006.01) | |
| *C07D 519/00* | (2006.01) | |
| *A61K 31/4439* | (2006.01) | |
| *A61K 31/4985* | (2006.01) | |
| *A61K 31/501* | (2006.01) | |
| *A61K 31/506* | (2006.01) | |
| *A61K 31/5377* | (2006.01) | |

(Continued)

(52) U.S. Cl.
CPC .......... *C07D 401/14* (2013.01); *A61K 31/4439* (2013.01); *A61K 31/497* (2013.01); *A61K 31/4985* (2013.01); *A61K 31/501* (2013.01); *A61K 31/506* (2013.01); *A61K 31/5377* (2013.01); *A61K 31/542* (2013.01); *A61K 45/06* (2013.01); *C07D 401/10* (2013.01); *C07D 403/14* (2013.01); *C07D 413/14* (2013.01); *C07D 487/04* (2013.01); *C07D 495/04* (2013.01); *C07D 498/04* (2013.01); *C07D 513/04* (2013.01); *C07D 519/00* (2013.01)

(58) Field of Classification Search
CPC . A61K 31/381; A61K 31/40; A61K 31/4015; A61K 31/425; A61K 31/435; A61K 31/495
See application file for complete search history.

(56) References Cited

U.S. PATENT DOCUMENTS

| | | |
|---|---|---|
| 7,884,108 B2 | 2/2011 | Blomgren et al. |
| 7,943,618 B2 | 5/2011 | Dewdney et al. |

(Continued)

FOREIGN PATENT DOCUMENTS

| | | |
|---|---|---|
| WO | 2009/039397 A2 | 3/2009 |
| WO | 2009/053269 A1 | 4/2009 |

(Continued)

OTHER PUBLICATIONS

International Search Report for PCT/US2011/050034 (Oct. 7, 2011).

(Continued)

*Primary Examiner* — Yong Chong
(74) *Attorney, Agent, or Firm* — Millen, White, Zelano & Branigan, P.C.

(57) ABSTRACT

Pyridone and pyrazinone compounds of Formula I including stereoisomers, tautomers, and pharmaceutically acceptable salts thereof, useful for inhibiting Btk kinase, and for treating immune disorders such as inflammation mediated by Btk kinase. Methods of using compounds of Formula I for in vitro, in situ, and in vivo diagnosis, and treatment of such disorders in mammalian cells, or associated pathological conditions, are disclosed.

19 Claims, 2 Drawing Sheets

(51) Int. Cl.
*A61K 31/542* (2006.01)
*A61K 45/06* (2006.01)
*C07D 498/04* (2006.01)

(56) References Cited

U.S. PATENT DOCUMENTS

| | | |
|---|---|---|
| 8,247,550 B2 | 8/2012 | Blomgren et al. |
| 8,299,077 B2 | 10/2012 | Berthel et al. |
| 2009/0082330 A1 | 3/2009 | Blomgren et al. |
| 2009/0105209 A1 | 4/2009 | Dewdney et al. |
| 2010/0004231 A1 | 1/2010 | Dewdney et al. |
| 2010/0222325 A1 | 9/2010 | Berthel et al. |
| 2011/0059944 A1 | 3/2011 | Blomgren et al. |

FOREIGN PATENT DOCUMENTS

| | | |
|---|---|---|
| WO | 2010/000633 A1 | 1/2010 |
| WO | 2010/100070 A1 | 9/2010 |

OTHER PUBLICATIONS

International Preliminary Report on Patentability for PCT/US2011/050034 (Mar. 5, 2013).

PYRIDINONES/PYRAZINONES, METHOD OF MAKING, AND METHOD OF USE THEREOF

CROSS REFERENCE TO RELATED APPLICATIONS

This non-provisional application filed under 37 CFR §1.53 (b), claims the benefit under 35 USC §119(e) of U.S. Provisional Application Ser. No. 61/379,044, filed on 1 Sep. 2010, which is incorporated by reference in entirety.

FIELD OF THE INVENTION

The invention relates generally to compounds for treating disorders mediated by Bruton's Tyrosine Kinase (Btk) including inflammation, immunological, and cancer, and more specifically to compounds which inhibit Btk activity. The invention also relates to methods of using the compounds for in vitro, in situ, and in vivo diagnosis or treatment of mammalian cells, or associated pathological conditions.

BACKGROUND OF THE INVENTION

Protein kinases, the largest family of human enzymes, encompass well over 500 proteins. Bruton's Tyrosine Kinase (Btk) is a member of the Tec family of tyrosine kinases, and is a regulator of early B-cell development as well as mature B-cell activation, signaling, and survival.

B-cell signaling through the B-cell receptor (BCR) can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice can also be resistant to developing collagen-induced arthritis and can be less susceptible to Staphylococcus-induced arthritis.

A large body of evidence supports the role of B-cells and the humoral immune system in the pathogenesis of autoimmune and/or inflammatory diseases. Protein-based therapeutics (such as Rituxan) developed to deplete B-cells, represent an approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in osteoclasts, mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases such as: SLE, rheumatoid arthritis, multiple vasculitides, idiopathic thrombocytopenic purpura (ITP), myasthenia gravis, allergic rhinitis, and asthma. In addition, Btk has been reported to play a role in apoptosis; thus, inhibition of Btk activity can be useful for cancer, as well as the treatment of B-cell lymphoma and leukemia. Moreover, given the role of Btk in osteoclast function, the inhibition of Btk activity can be useful for the treatment of bone disorders such as osteoporosis.

SUMMARY OF THE INVENTION

The invention relates generally to Formula I compounds with Bruton's Tyrosine Kinase (Btk) modulating activity.

Formula I compounds have the structures:

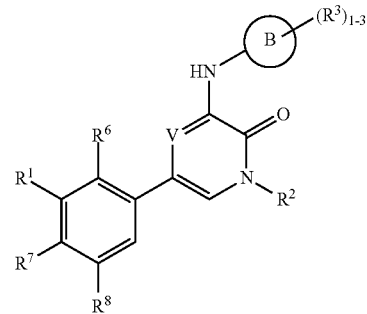

including stereoisomers, tautomers, or pharmaceutically acceptable salts thereof. The various substituents are defined herein below.

One aspect of the invention is a pharmaceutical composition comprised of a Formula I compound and a pharmaceutically acceptable carrier, glidant, diluent, or excipient. The pharmaceutical composition may further comprise a second therapeutic agent.

Another aspect of the invention is a process for making a pharmaceutical composition which comprises combining a Formula I compound with a pharmaceutically acceptable carrier.

The invention includes a method of treating a disease or disorder which method comprises administering a therapeutically effective amount of a Formula I compound to a patient with a disease or disorder selected from immune disorders, cancer, cardiovascular disease, viral infection, inflammation, metabolism/endocrine function disorders and neurological disorders, and mediated by Bruton's tyrosine kinase.

The invention includes a kit for treating a condition mediated by Bruton's tyrosine kinase, comprising: a) a first pharmaceutical composition comprising a Formula I compound; and b) instructions for use.

The invention includes a Formula I compound for use as a medicament, and for use in treating a disease or disorder selected from immune disorders, cancer, cardiovascular disease, viral infection, inflammation, metabolism/endocrine function disorders and neurological disorders, and mediated by Bruton's tyrosine kinase.

The invention includes use of a Formula I compound in the manufacture of a medicament for the treatment of immune disorders, cancer, cardiovascular disease, viral infection, inflammation, metabolism/endocrine function disorders and neurological disorders, and where the medicament mediates Bruton's tyrosine kinase.

The invention includes methods of making a Formula I compound.

DETAILED DESCRIPTION OF EXEMPLARY EMBODIMENTS

Figure 1:
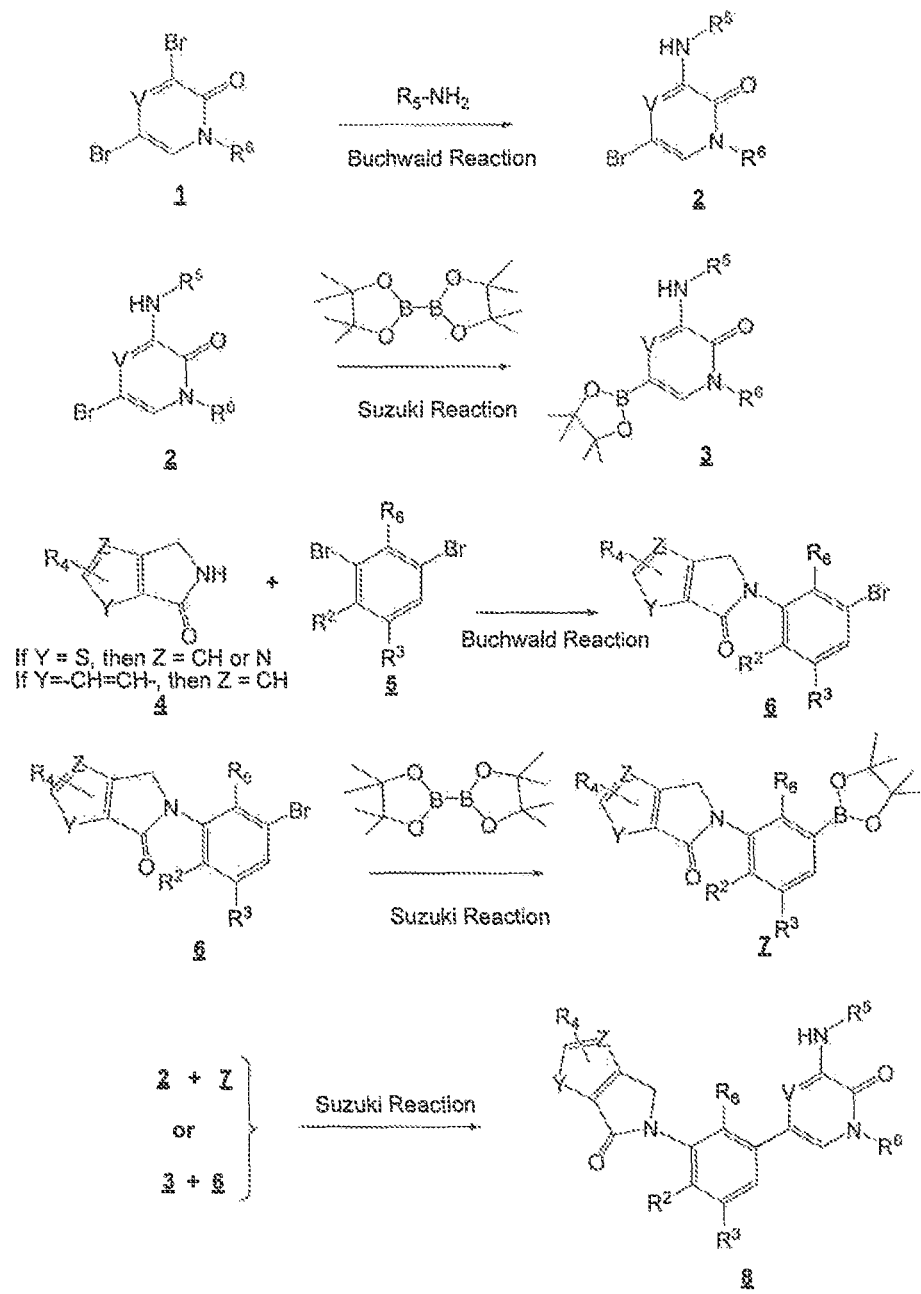
FIG. 1 shows an exemplary synthetic route to make Formula I compounds 8 which involves a Buchwald reaction to couple a bicyclic pyrolone 4 with a methyl or hydroxymethyl benzene 5 to yield intermediate 6, followed by either successive Suzuki reactions to prepare a boronate 7 and couple it with a bromo-pyridone or -pyrazinone 2, or a single Suzuki reaction to couple 6 with a pyridone- or pyrazinone-boronate 3. Bromo-pyridone or -pyrazinone 2 can be prepared by a Buchwald reaction of a dibromo-pyridone or -pyrazinone with a heterocyclic amine or an aniline. Pyridone- or pyrazinone-boronates 3 can be prepared by a Suzuki reactions of 2 with a diboronate.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus, sulfur, and silicon, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperidonyl, oxopiperazinyl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (═O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammaII, calicheamicin omegaII (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the Btk inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their minor image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable minor images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center (s). The prefixes d and l or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. In one aspect, a stereoisomer of this invention can be present in predominant form, e.g. greater than 50% ee (enantiomeric excess), greater than 80% ee, greater than 90% ee, greater than 95% ee, or greater than 99% ee.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "diastereomer" refers to stereoisomeric molecules which are not enantiomers. Diastereomers include cis-trans isomers and conformational isomers which have the same molecular formula but which have a different geometric structure.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The terms "compound of this invention," and "compounds of the present invention" include compounds of Formulas I and stereoisomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Pyridone and Pyrazinone Compounds

The present invention provides pyridone and pyrazinone compounds of Formula I, including Formulas Ia-bf, and pharmaceutical formulations thereof, which are potentially useful in the treatment of diseases, conditions and/or disorders modulated by Btk kinase Formula I compounds have the structure:

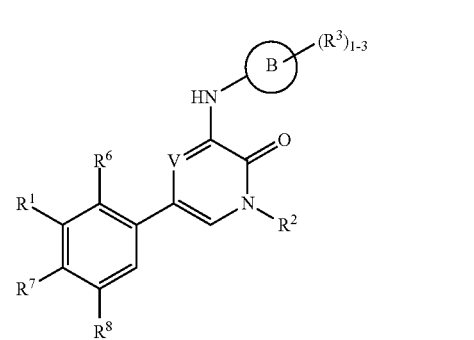

and stereoisomers, tautomers, or pharmaceutically acceptable salts thereof, wherein:

$R^1$ is selected from:

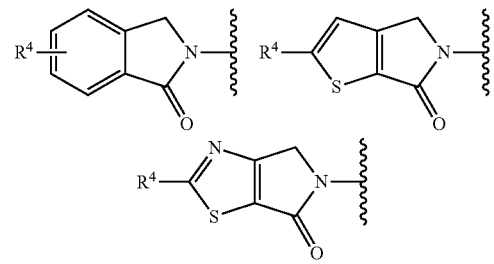

where the wavy line indicates the site of attachment;

$R^4$ is selected from OH, CN, $NR^bR^c$, piperidinyl, $C_3$-$C_6$ cycloalkyl optionally substituted with $C_1$-$C_6$ alkyl or $C_1$-$C_4$ haloalkyl, and $C_1$-$C_6$ alkyl optionally substituted with OH or $OC_1$-$C_4$ alkyl;

$R^2$ is H, $CH_3$ or $CF_3$;

ring B is selected from phenyl, 5-6 membered heteroaryl having at least one nitrogen ring atom, and 8-11 membered heterocyclyl having at least one nitrogen ring atom;

$R^3$ is independently selected from H, $-R^a$, $-OR^b$, $-SR^b$, $-NR^bR^c$, halo, cyano, nitro, $-COR^b$, $-CO_2R^b$, $-CONR^bR^c$, $-OCOR^b$, $-OCO_2R^a$, $-OCONR^bR^c$, $-NR^cCOR^b$, $-NR^cCO_2R^a$, $-NR^cCONR^bR^c$, $-CO_2R^b$, $-CONR^bR^c$, $-NR^cCOR^b$, $-SOR^a$, $-SO_2R^a$, $-SO_2NR^bR^c$, and $-NR^cSO_2R^a$; or two adjacent $R^3$ groups are optionally taken together to form a 5-6 membered ring having 0-2 heteroatoms selected from O, S or N, wherein said 5-6 membered ring is fused to ring B;

$R^a$ is $C_1$-$C_6$ alkyl, cycloalkyl, heterocycloalkyl, aryl, or heteroaryl, wherein each member of $R^a$ is optionally substituted with one to three $R^{11}$ groups;

$R^b$ is H, $C_1$-$C_6$ alkyl, cycloalkyl, heterocycloalkyl, aryl, or heteroaryl, wherein each member of $R^b$ except H is optionally substituted with one to three $R^{11}$ groups;

$R^c$ is H or $C_1$-$C_4$ alkyl optionally substituted with one or three $R^{11}$ groups; or $R^b$ and $R^c$, and the nitrogen to which they are attached, form an optionally substituted heterocycloalkyl group;

each $R^{11}$ is independently selected from $C_1$-$C_4$ alkyl, cycloalkyl, heterocycloalkyl, aryl, heteroaryl, aryl-$C_1$-$C_4$ alkyl-, heteroaryl-$C_1$-$C_4$ alkyl-, cycloalkyl-$C_1$-$C_4$ alkyl-, heterocycloalkyl-$C_1$-$C_4$ alkyl-, $C_1$-$C_4$ haloalkyl-, —$OC_1$-$C_4$ alkyl, —O-heterocycloalkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —NH($C_1$-$C_4$ alkyl), —N($C_1$-$C_4$ alkyl)($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —$CO_2H$, —C(O)$OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$ ($C_1$-$C_4$ alkyl), —$NHSO_2$(phenyl), and —$NHSO_2$($C_1$-$C_4$ haloalkyl);

$R^5$ is H or F;

$R^6$ is H, $CH_3$, F, Cl, CN, $OCH_3$, OH, or methyl substituted with OH, $OCH_3$ or one or more halo groups;

$R^7$ is H, $CH_3$, F, Cl, CN or $OCH_3$;

$R^8$ is H, $CH_3$, $CF_3$, F, Cl, CN or $OCH_3$;

V is CH or N;

each $R^9$ is independently $C_1$-$C_3$ alkyl; and each $R^{10}$ is independently H or $CH_3$.

Exemplary embodiments of Formula I compounds include $R^2$ is H or $CH_3$.

Exemplary embodiments of Formula I compounds include wherein $R^3$ is H, —$R^a$, —$NR^bR^c$ or —C(O)$R^b$.

Exemplary embodiments of Formula I compounds include wherein $R^3$ is selected from cyclopropyl, azetidinyl, morpholinyl, piperidinyl, oxopiperidinyl, piperazinyl, and oxopiperazinyl, optionally substituted with F, OH, $CH_3$, or $COCH_3$ Exemplary embodiments of Formula I compounds include wherein $R^3$ is:

where the wavy line indicates the site of attachment.

Exemplary embodiments of Formula I compounds include wherein $R^4$ is H, t-butyl, N-pyrrolidinyl, N-piperidinyl, N-azepanyl, 2-hydroxy-2-methylpropyl, prop-1-en-2-yl, —N($CH_3$)Et, i-propyl, cyclopentyl, cyclohexyl, 3-methylbutan-2-yl, —N($CH_3$)(i-Pr), or —NH(cyclopropyl).

Exemplary embodiments of Formula I compounds include wherein $R^5$ is H or F.

Exemplary embodiments of Formula I compounds include wherein $R^6$ is H, $CH_3$, F, or $CH_2OH$.

Exemplary embodiments of Formula I compounds include wherein $R^7$ is H or F.

Exemplary embodiments of Formula I compounds include wherein B is pyrazolo[1,5-a]pyrazin-2-yl, pyrazol-3-yl, pyrimidin-4-yl, or pyridin-2-yl.

Exemplary embodiments of Formula I compounds include wherein:

is selected from the structures:

-continued
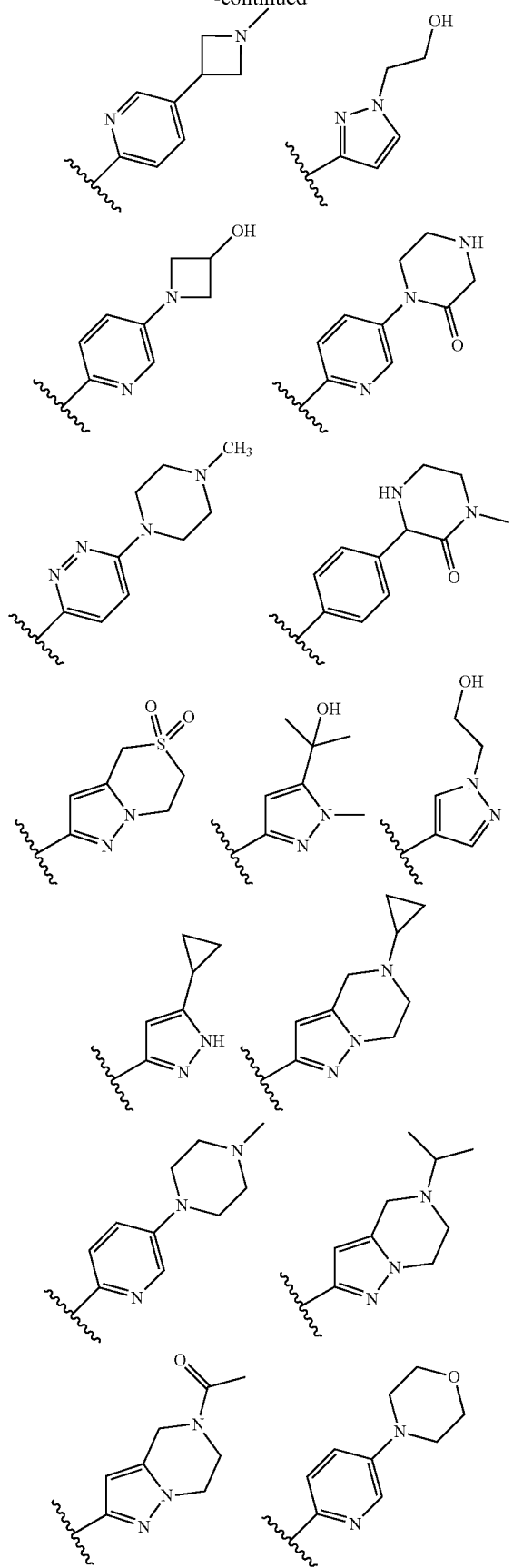
-continued
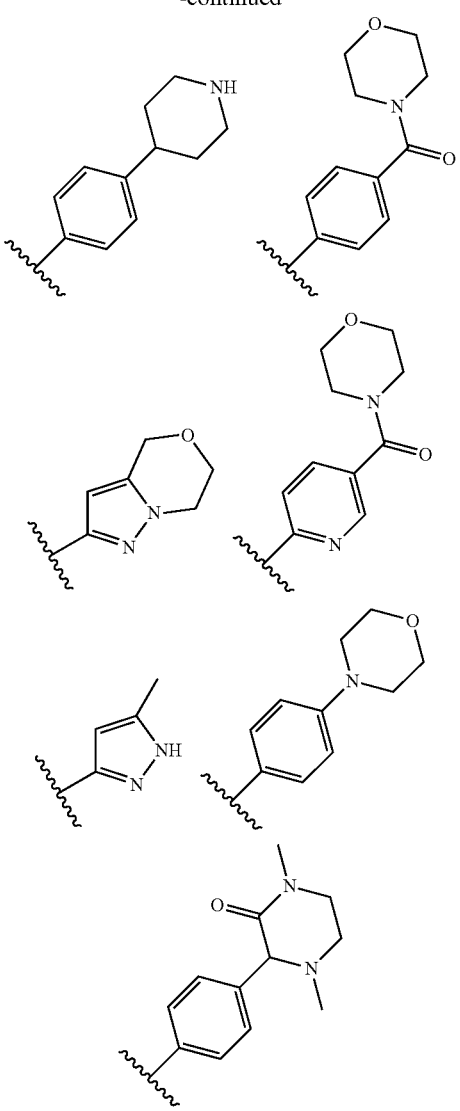
where the wavy line indicates the site of attachment.
Exemplary embodiments of Formula I compounds include compounds having the structure of Formula Ia:
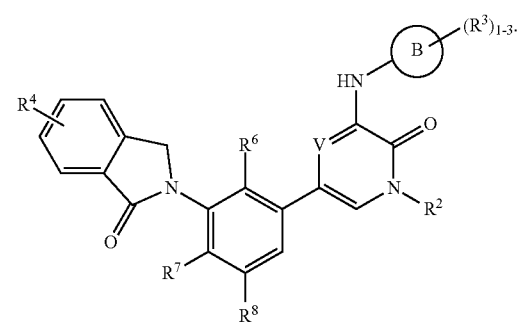
Exemplary embodiments of Formula I compounds include compounds having the structure of Formula Ib:

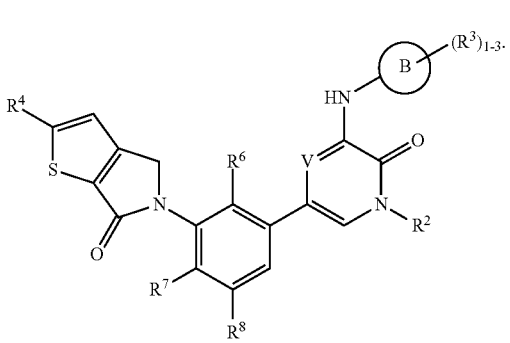

Exemplary embodiments of Formula I compounds include compounds having the structure of Formula Ic:

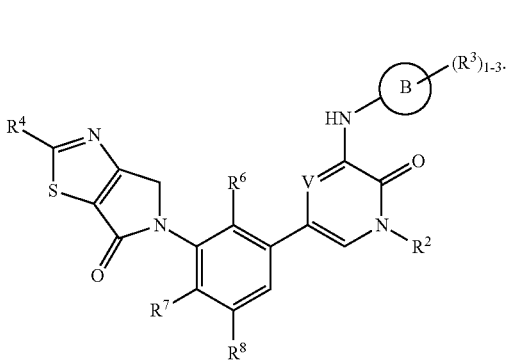

Exemplary embodiments of Formula I compounds include those from Table 1 and Table 2.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all diastereomers, including cis-trans (geometric) and conformational isomers. For example, if a Formula I compound incorporates a double bond or a fused ring, the cis- and trans-forms, as well as mixtures thereof, are embraced within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Formula I compounds were tested by a standard biochemical Btk Kinase Assay (Example 901).

A general procedure for a standard cellular Btk Kinase Assay that can be used to test Formula I compounds is a Ramos Cell Btk Assay (Example 902).

A standard cellular B-cell proliferation assay can be used to test Formula I compounds with B-cells purified from spleen of Balb/c mice (Example 903).

A standard T cell proliferation assay can be used to test Formula I compounds with T-cells purified from spleen of Balb/c mice (Example 904).

A CD86 Inhibition assay can be conducted on Formula I compounds for the inhibition of B cell activity using total mouse splenocytes purified from spleens of 8-16 week old Balb/c mice (Example 905).

A B-ALL Cell Survival Assay can be conducted on Formula I compounds to measure the number of viable B-ALL cells in culture (Example 906).

A CD69 Whole Blood Assay can be conducted on Formula I compounds to determine the ability of compounds to inhibit the production of CD69 by B lymphocytes in human whole blood activated by crosslinking surface IgM with goat F(ab')2 anti-human IgM (Example 907).

Exemplary Formula I compounds in Tables 1 and 2 were made, characterized, and tested for inhibition of Btk according to the methods of this invention, and have the following structures and corresponding names (ChemDraw Ultra, Version 9.0.1, and ChemBioDraw, Version 11.0, CambridgeSoft Corp., Cambridge Mass.). Where more than one name is associated with a Formula I compound or intermediate, the chemical structure shall define the compound.

TABLE 1

| No. | Structure | Name | M + H m/z | Btk IC$_{50}$ (μMol) |
|---|---|---|---|---|
| 101 | 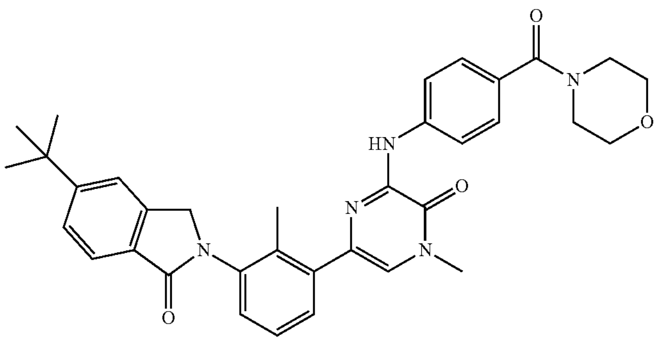 [SMILES: Cc1c(-c2cn(C)c(=O)c(Nc3ccc(C(=O)N4CCOCC4)cc3)n2)cccc1N1Cc2cc(C(C)(C)C)ccc2C1=O] | 5-tert-butyl-2-(2-methyl-3-(4-methyl-6-(4-(morpholine-4-carbonyl)phenyl-amino)-5-oxo-4,5-dihydropyrazin-2-yl)phenyl)isoindolin-1-one | 591.5 | 0.0364 |
| 102 | 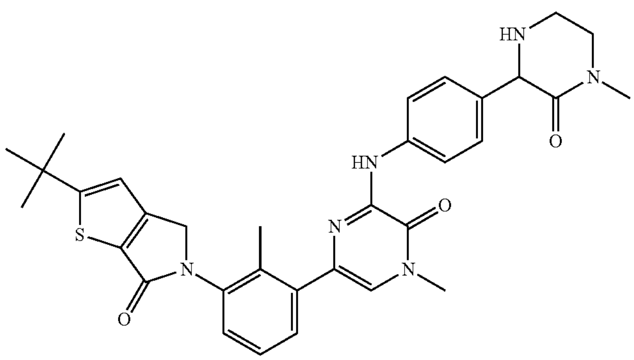 [SMILES: Cc1c(-c2cn(C)c(=O)c(Nc3ccc(C4NCCN(C)C4=O)cc3)n2)cccc1N1Cc2cc(C(C)(C)C)sc2C1=O] | 2-tert-butyl-5-(2-methyl-3-(4-methyl-6-(4-(4-methyl-3-oxopiperazin-2-yl)phenylamino)-5-oxo-4,5-dihydro-pyrazin-2-yl)phenyl)-4H-thieno[2,3-c]pyrrol-6(5H)-one | 597.2 | 0.0115 |
| 103 | 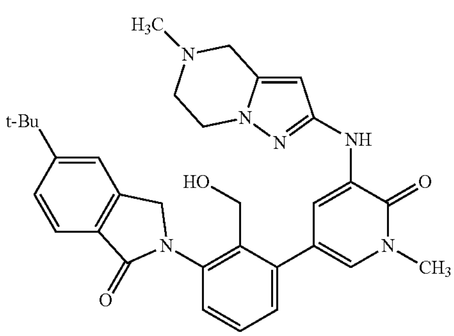 | 5-tert-butyl-2-(2-(hydroxymethyl)-3-(1-methyl-5-(5-methyl-4,5,6,7-tetrahydropyrazolo[1,5-a]pyrazin-2-ylamino)-6-oxo-1,6-dihydropyridin-3-yl)phenyl)isoindolin-1-one | 553.2 | |
| 104 | 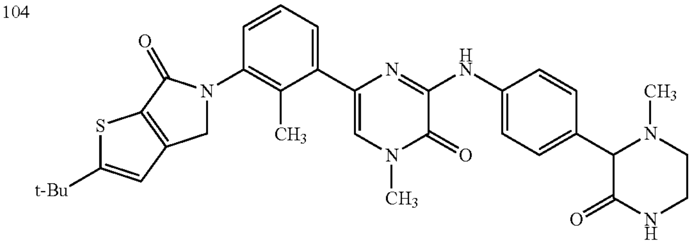 | 2-tert-butyl-5-(2-methyl-3-(4-methyl-6-(4-(1-methyl-3-oxopiperazin-2-yl)phenylamino)-5-oxo-4,5-dihydropyrazin-2-yl)phenyl)-4H-thieno[2,3-c]pyrrol-6(5H)-one | 597.7 | 0.095 |

TABLE 1-continued

| No. | Structure | Name | M + H m/z | Btk IC$_{50}$ (μMol) |
|---|---|---|---|---|
| 105 | 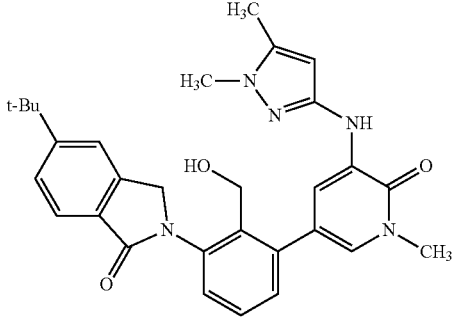<br>1c | 5-tert-butyl-2-(3-(5-(1,5-dimethyl-1H-pyrazol-3-ylamino)-1-methyl-6-oxo-1,6-dihydropyridin-3-yl)-2-(hydroxymethyl)phenyl)isoindolin-1-one | 512.3 | |
| 106 | 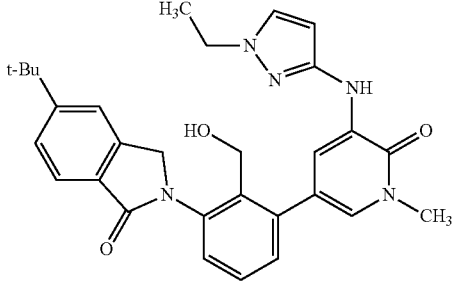<br>3d | 5-tert-butyl-2-(3-(5-(1-ethyl-1H-pyrazol-3-ylamino)-1-methyl-6-oxo-1,6-dihydropyridin-3-yl)-2-(hydroxymethyl)phenyl)isoindolin-1-one | 512.3 | |
| 107 | 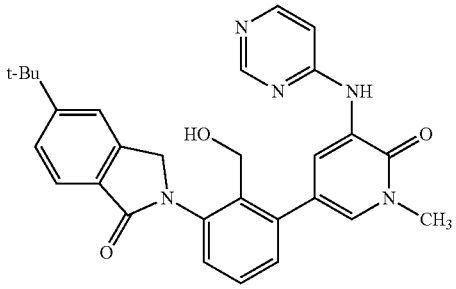<br>5b | 5-tert-butyl-2-(2-(hydroxymethyl)-3-(1-methyl-6-oxo-5-(pyrimidin-4-ylamino)-1,6-dihydropyridin-3-yl)phenyl)isoindolin-1-one | 496.2 | |
| 108 | 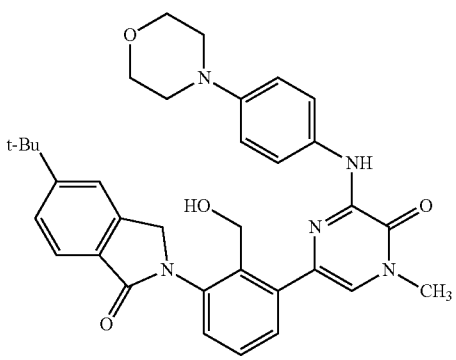<br>6b | 5-tert-butyl-2-(2-(hydroxymethyl)-3-(4-methyl-6-(4-morpholinophenylamino)-5-oxo-4,5-dihydropyrazin-2-yl)phenyl)isoindolin-1-one | 580.3 | |

TABLE 1-continued

| No. | Structure | Name | M + H m/z | Btk IC$_{50}$ (μMol) |
|---|---|---|---|---|
| 109 | 11b | 5-tert-butyl-2-(3-(6-(1-cyclopropyl-1H-pyrazol-4-ylamino)-4-methyl-5-oxo-4,5-dihydropyrazin-2-yl)-2-(hydroxymethyl)phenyl)isoindolin-1-one | 525.2 | |
| 110 | 12d | 5-tert-butyl-2-(3-(5-(3-cyclopropyl-1H-pyrazol-5-ylamino)-1-methyl-6-oxo-1,6-dihydropyridin-3-yl)-2-(hydroxymethyl)phenyl)isoindolin-1-one | 524.2 | |
| 111 | 13f | 5-tert-butyl-2-(3-(6-(1-ethyl-1H-pyrazol-4-ylamino)-4-methyl-5-oxo-4,5-dihydropyrazin-2-yl)-2-(hydroxymethyl)phenyl)isoindolin-1-one | 513.2 | |
| 112 | 15c | 5-tert-butyl-2-(2-(hydroxymethyl)-3-(4-methyl-5-oxo-6-(pyridin-3-ylamino)-4,5-dihydropyrazin-2-yl)phenyl)isoindolin-1-one | 496.2 | |
| 113 | 16d | 5-tert-butyl-2-(2-(hydroxymethyl)-3-(1-methyl-6-oxo-5-(pyridin-2-ylamino)-1,6-dihydropyridin-3-yl)phenyl)isoindolin-1-one | 495.2 | |

TABLE 1-continued

| No. | Structure | Name | M + H m/z | Btk IC$_{50}$ (μMol) |
|---|---|---|---|---|
| 114 | 4m | 2-tert-butyl-5-(2-(hydroxymethyl)-3-(1-methyl-5-(5-methyl-4,5,6,7-tetrahydropyrazolo[1,5-a]pyrazin-2-ylamino)-6-oxo-1,6-dihydropyridin-3-yl)phenyl)-4H-thieno[3,2-c]pyrrol-6(5H)-one | 559.4 | |
| 115 | 1k | 5-tert-butyl-2-(3-(5-(1-cyclopropyl-1H-pyrazol-3-ylamino)-1-methyl-6-oxo-1,6-dihydropyridin-3-yl)-2-(hydroxymethyl)phenyl)isoindolin-1-one | 524.2 | |
| 116 | 2n | 2-cyclopropyl-5-(2-(hydroxymethyl)-3-(1-methyl-6-oxo-5-(pyrimidin-4-ylamino)-1,6-dihydropyridin-3-yl)phenyl)-4H-thieno[3,2-c]pyrrol-6(5H)-one | 486.2 | |
| 117 | 6f | 2-(3-(5-(5-(azetidin-3-yl)pyridin-2-ylamino)-1-methyl-6-oxo-1,6-dihydropyridin-3-yl)-2-(hydroxymethyl)phenyl)-5-tert-butylisoindolin-1-one | 550.2 | |

TABLE 1-continued

| No. | Structure | Name | M + H m/z | Btk IC$_{50}$ (μMol) |
|---|---|---|---|---|
| 118 | 7a | 5-tert-butyl-2-(2-(hydroxymethyl)-3-(1-methyl-5-(5-(1-methylazetidin-3-yl)pyridin-2-ylamino)-6-oxo-1,6-dihydropyridin-3-yl)phenyl)isoindolin-1-one | 564.3 | |
| 119 | 12g | 2-(3-(6-(1-(2-hydroxyethyl)-1H-pyrazol-4-ylamino)-4-methyl-5-oxo-4,5-dihydropyrazin-2-yl)-2-(hydroxymethyl)phenyl)-3,4,5,6,7,8-hexahydrobenzothieno[2,3-c]pyridin-1(2H)-one | 528.3 | |
| 120 | 13c | 5-tert-butyl-2-(3-(5-(5-(3-hydroxyazetidin-1-yl)pyridin-2-ylamino)-1-methyl-6-oxo-1,6-dihydropyridin-3-yl)-2-(hydroxymethyl)phenyl)isoindolin-1-one | 566.3 | |
| 121 | 14e | 5-tert-butyl-2-(2-(hydroxymethyl)-3-(1-methyl-6-oxo-5-(5-(2-oxopiperazin-1-yl)pyridin-2-ylamino)-1,6-dihydropyridin-3-yl)phenyl)isoindolin-1-one | 593.3 | |

TABLE 1-continued

| No. | Structure | Name | M + H m/z | Btk IC50 (μMol) |
|---|---|---|---|---|
| 122 | 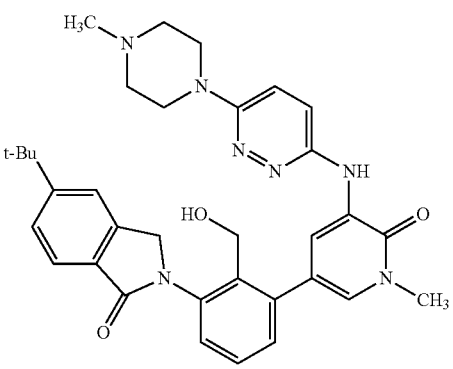<br>15f | 5-tert-butyl-2-(2-(hydroxymethyl)-3-(1-methyl-5-(6-(4-methylpiperazin-1-yl)pyridazin-3-ylamino)-6-oxo-1,6-dihydropyridin-3-yl)phenyl)isoindolin-1-one | 594.3 | |
| 123 | 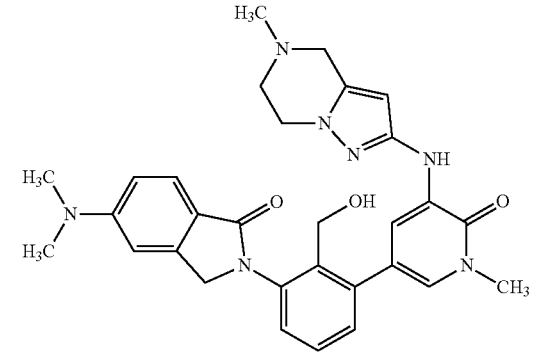<br>16g | 5-(dimethylamino)-2-(2-(hydroxymethyl)-3-(1-methyl-5-(5-methyl-4,5,6,7-tetrahydropyrazolo[1,5-a]pyrazin-2-ylamino)-6-oxo-1,6-dihydropyridin-3-yl)phenyl)isoindolin-1-one | 540.3 | |
| 124 | 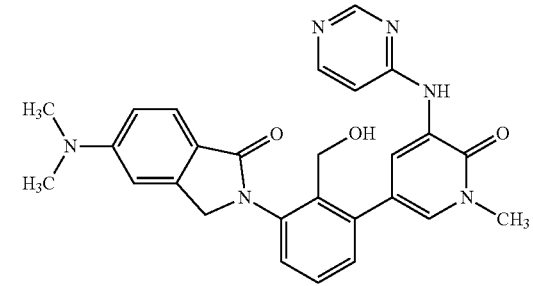<br>17b | 5-(dimethylamino)-2-(2-(hydroxymethyl)-3-(1-methyl-6-oxo-5-(pyrimidin-4-ylamino)-1,6-dihydropyridin-3-yl)phenyl)isoindolin-1-one | 483.2 | |
| 125 | 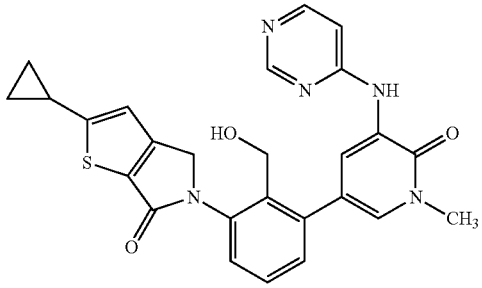<br>2n | 2-tert-butyl-5-(2-(hydroxymethyl)-3-(1-methyl-6-oxo-5-(pyrimidin-4-ylamino)-1,6-dihydropyridin-3-yl)phenyl)-4,5-dihydropyrrolo[3,4-d]thiazol-6-one | 503 | |

TABLE 1-continued

| No. | Structure | Name | M + H m/z | Btk IC$_{50}$ (µMol) |
|---|---|---|---|---|
| 126 | 4m | 2-tert-butyl-5-(3-(5-(5-cyclopropyl-1H-pyrazol-3-ylamino)-1-methyl-6-oxo-1,6-dihydropyridin-3-yl)-2-(hydroxymethyl)-phenyl)-4H-pyrrolo-[3,4-d]thiazol-6(5H)-one | 531 | |

The examples in Table 2 were prepared using procedures similar to those for examples 101-126.

TABLE 2

| No | Structure | Name | M + H m/z | Btk IC$_{50}$ (µMol) |
|---|---|---|---|---|
| 127 | 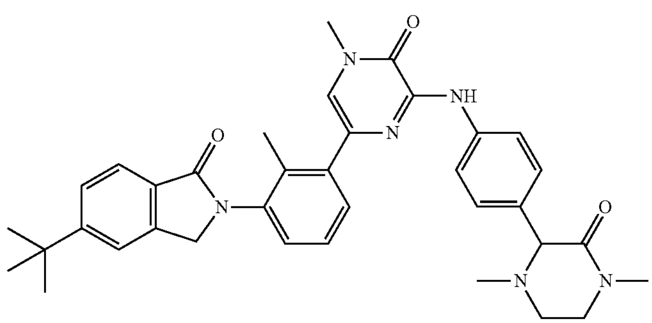 [SMILES: Cc1c(-c2cn(C)c(=O)c(Nc3ccc(C4C(=O)N(C)CCN4C)cc3)n2)cccc1N1Cc2cc(C(C)(C)C)ccc2C1=O] | 5-tert-butyl-2-[3-(6-{[4-(1,4-dimethyl-3-oxopiperazin-2-yl)phenyl]amino}-4-methyl-5-oxo-4,5-dihydropyrazin-2-yl)-2-methylphenyl]-2,3-dihydro-1H-isoindol-1-one | 604.5 | 0.0294 |
| 128 | 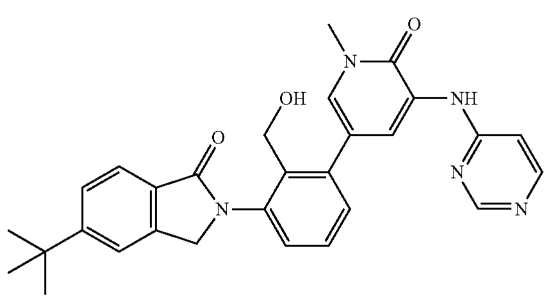 [SMILES: Cn1cc(-c2cccc(N3Cc4cc(C(C)(C)C)ccc4C3=O)c2CO)cc(Nc2ccncn2)c1=O] | 5-tert-butyl-2-[2-(hydroxymethyl)-3-[1-methyl-6-oxo-5-(pyrimidin-4-ylamino)-1,6-dihydropyridin-3-yl]phenyl]-2,3-dihydro-1H-isoindol-1-one | 496.2 | |
| 129 | 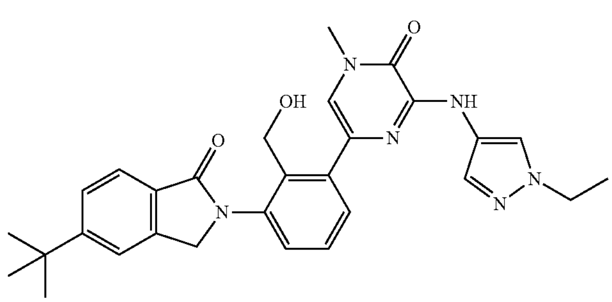 [SMILES: CCn1cc(Nc2nc(-c3cccc(N4Cc5cc(C(C)(C)C)ccc5C4=O)c3CO)cn(C)c2=O)cn1] | 5-tert-butyl-2-(3-{6-[(1-ethyl-1H-pyrazol-4-yl)amino]-4-methyl-5-oxo-4,5-dihydropyrazin-2-yl}-2-(hydroxymethyl)phenyl)-2,3-dihydro-1H-isoindol-1-one | 513.2 | |

TABLE 2-continued

| No | Structure | Name | M + H m/z | Btk IC$_{50}$ (μMol) |
|---|---|---|---|---|
| 130 | 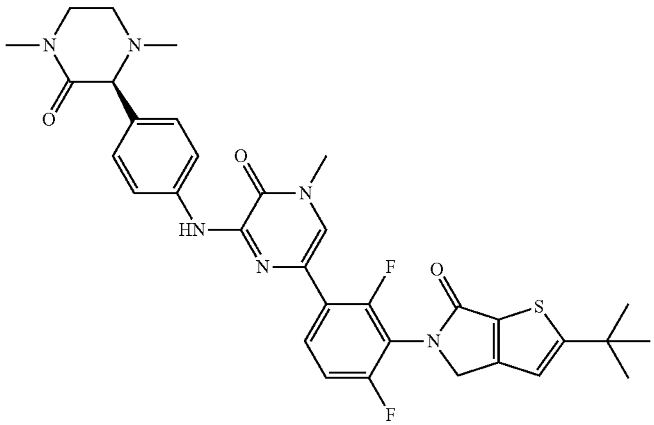 [SMILES: CN1CCN(C)[C@@H](c2ccc(Nc3nc(-c4ccc(F)c(N5Cc6cc(C(C)(C)C)sc6C5=O)c4F)cn(C)c3=O)cc2)C1=O] | 5-(3-{2-tert-butyl-6-oxo-4H,5H,6H-thieno[2,3-c]pyrrol-5-yl}-2,4-difluorophenyl)-3-({4-[(2S)-1,4-dimethyl-3-oxopiperazin-2-yl]phenyl}amino)-1-methyl-1,2-dihydropyrazin-2-one | | 0.0337 |
| 131 | 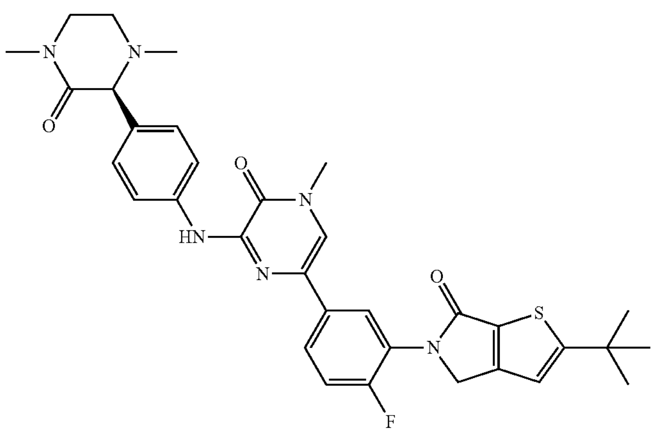 [SMILES: CN1CCN(C)[C@@H](c2ccc(Nc3nc(-c4ccc(F)c(N5Cc6cc(C(C)(C)C)sc6C5=O)c4)cn(C)c3=O)cc2)C1=O] | 5-(3-{2-tert-butyl-6-oxo-4H,5H,6H-thieno[2,3-c]pyrrol-5-yl}-4-fluorophenyl)-3-({4-[(2S)-1,4-dimethyl-3-oxopiperazin-2-yl]phenyl}amino)-1-methyl-1,2-dihydropyrazin-2-one | | 0.0474 |
| 132 | 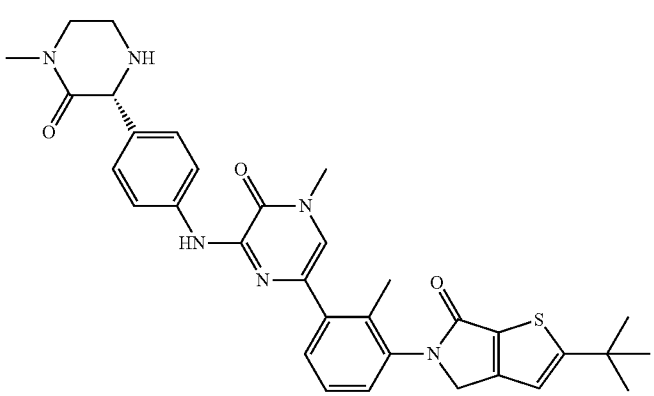 [SMILES: Cc1c(-c2cn(C)c(=O)c(Nc3ccc([C@H]4NCCN(C)C4=O)cc3)n2)cccc1N1Cc2cc(C(C)(C)C)sc2C1=O] | 5-(3-{2-tert-butyl-6-oxo-4H,5H,6H-thieno[2,3-c]pyrrol-5-yl}-2-methylphenyl)-1-methyl-3-({4-[(2R)-4-methyl-3-oxopiperazin-2-yl]phenyl}amino)-1,2-dihydropyrazin-2-one | | |

TABLE 2-continued

| No | Structure | Name | M + H m/z | Btk IC$_{50}$ (μMol) |
|---|---|---|---|---|
| 133 | 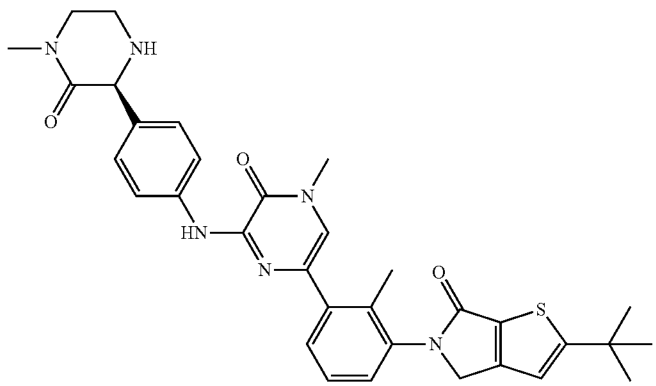 [SMILES: Cc1c(-c2cn(C)c(=O)c(Nc3ccc([C@@H]4NCCN(C)C4=O)cc3)n2)cccc1N1Cc2cc(C(C)(C)C)sc2C1=O] | 5-(3-{2-tert-butyl-6-oxo-4H,5H,6H-thieno[2,3-c]pyrrol-5-yl}-2-methylphenyl)-1-methyl-3-({4-[(2S)-4-methyl-3-oxopiperazin-2-yl]phenyl}amino)-1,2-dihydropyrazin-2-one | | |
| 134 | 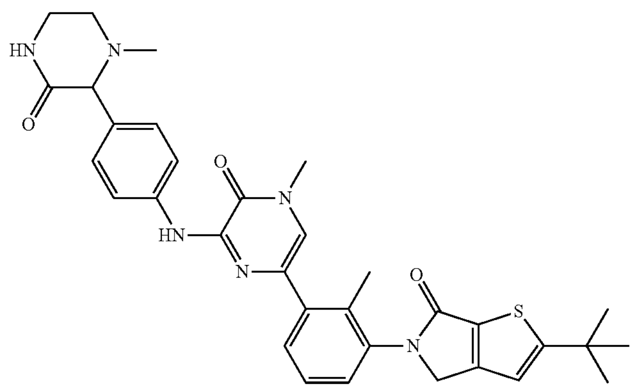 [SMILES: Cc1c(-c2cn(C)c(=O)c(Nc3ccc(C4C(=O)NCCN4C)cc3)n2)cccc1N1Cc2cc(C(C)(C)C)sc2C1=O] | 5-(3-{2-tert-butyl-6-oxo-4H,5H,6H-thieno[2,3-c]pyrrol-5-yl}-2-methylphenyl)-1-methyl-3-{[4-(1-methyl-3-oxopiperazin-2-yl)phenyl]amino}-1,2-dihydropyrazin-2-one | 597.7 | 0.0247 |
| 135 | 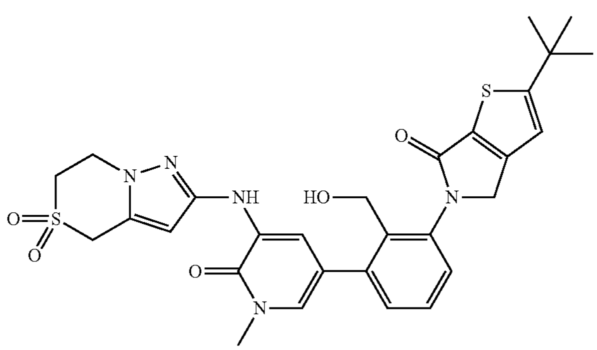 [SMILES: Cn1cc(-c2cccc(N3Cc4cc(C(C)(C)C)sc4C3=O)c2CO)cc(Nc2cc3n(n2)CCS(=O)(=O)C3)c1=O] | 2-{[5-(3-{2-tert-butyl-6-oxo-4H,5H,6H-thieno[2,3-c]pyrrol-5-yl}-2-(hydroxymethyl)phenyl)-1-methyl-2-oxo-1,2-dihydropyridin-3-yl]amino}-4H,6H,7H-pyrazolo[3,2-c][1,4]thiazine-5,5-dione | 594 | |
| 136 | 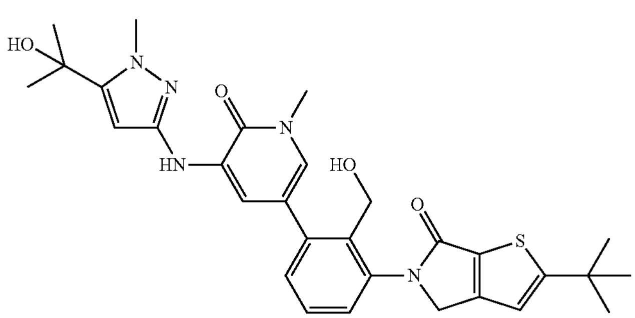 [SMILES: Cn1nc(Nc2cc(-c3cccc(N4Cc5cc(C(C)(C)C)sc5C4=O)c3CO)cn(C)c2=O)cc1C(C)(C)O] | 5-(3-{2-tert-butyl-6-oxo-4H,5H,6H-thieno[2,3-c]pyrrol-5-yl}-2-(hydroxymethyl)phenyl)-3-{[5-(2-hydroxypropan-2-yl)-1-methyl-1H-pyrazol-3-yl]amino}-1-methyl-1,2-dihydropyridin-2-one | 562.1 | |

TABLE 2-continued

| No | Structure | Name | M + H m/z | Btk IC$_{50}$ (μMol) |
|---|---|---|---|---|
| 137 | 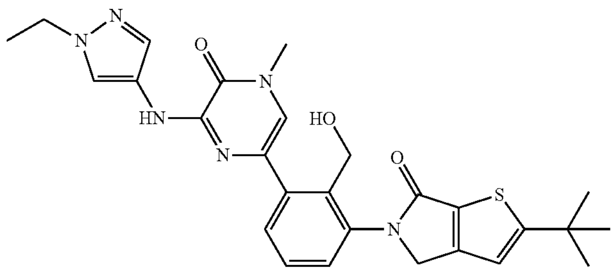 [SMILES: CCn1cc(Nc2nc(-c3cccc(N4Cc5cc(C(C)(C)C)sc5C4=O)c3CO)cn(C)c2=O)cn1] | 5-(3-{2-tert-butyl-6-oxo-4H,5H,6H-thieno[2,3-c]pyrrol-5-yl}-2-(hydroxymethyl)phenyl)-3-[(1-ethyl-1H-pyrazol-4-yl)amino]-1-methyl-1,2-dihydropyrazin-2-one | 519.2 | |
| 138 | 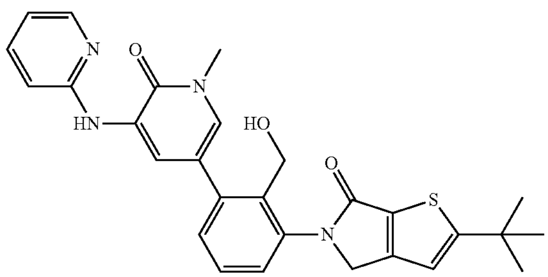 [SMILES: Cn1cc(-c2cccc(N3Cc4cc(C(C)(C)C)sc4C3=O)c2CO)cc(Nc2ccccn2)c1=O] | 5-(3-{2-tert-butyl-6-oxo-4H,5H,6H-thieno[2,3-c]pyrrol-5-yl}-2-(hydroxymethyl)phenyl)-1-methyl-3-(pyridin-2-ylamino)-1,2-dihydropyridin-2-one | 501.2 | |
| 139 | 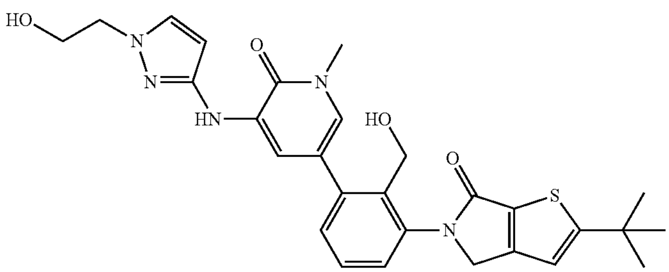 [SMILES: Cn1cc(-c2cccc(N3Cc4cc(C(C)(C)C)sc4C3=O)c2CO)cc(Nc2ccn(CCO)n2)c1=O] | 5-(3-{2-tert-butyl-6-oxo-4H,5H,6H-thieno[2,3-c]pyrrol-5-yl}-2-(hydroxymethyl)phenyl)-3-{[1-(2-hydroxyethyl)-1H-pyrazol-3-yl]amino}-1-methyl-1,2-dihydropyridin-2-one | 534.2 | |
| 140 | 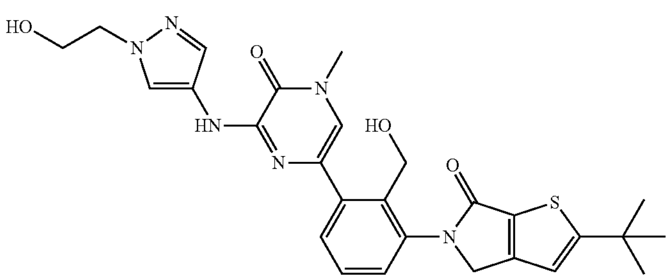 [SMILES: Cn1cc(-c2cccc(N3Cc4cc(C(C)(C)C)sc4C3=O)c2CO)nc(Nc2cnn(CCO)c2)c1=O] | 5-(3-{2-tert-butyl-6-oxo-4H,5H,6H-thieno[2,3-c]pyrrol-5-yl}-2-(hydroxymethyl)phenyl)-3-{[1-(2-hydroxyethyl)-1H-pyrazol-4-yl]amino}-1-methyl-1,2-dihydropyrazin-2-one | 535.1 | |
| 141 | 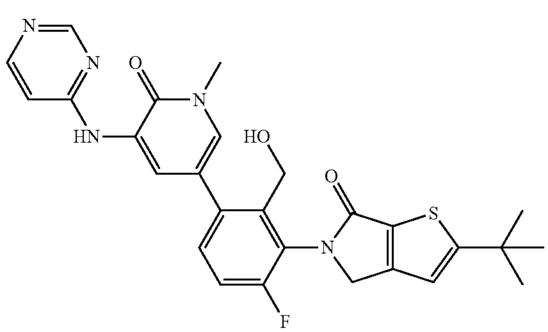 [SMILES: Cn1cc(-c2ccc(F)c(N3Cc4cc(C(C)(C)C)sc4C3=O)c2CO)cc(Nc2ccncn2)c1=O] | 5-(3-{2-tert-butyl-6-oxo-4H,5H,6H-thieno[2,3-c]pyrrol-5-yl}-4-fluoro-2-(hydroxymethyl)phenyl)-1-methyl-3-(pyrimidin-4-ylamino)-1,2-dihydropyridin-2-one | 520.1 | |

TABLE 2-continued

| No | Structure | Name | M + H m/z | Btk IC$_{50}$ (μMol) |
|---|---|---|---|---|
| 142 | 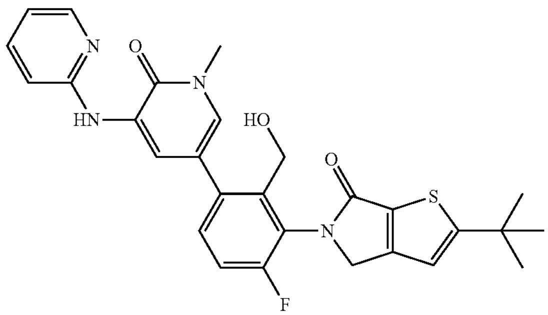 [SMILES: Cn1cc(-c2ccc(F)c(N3Cc4cc(C(C)(C)C)sc4C3=O)c2CO)cc(Nc2ccccn2)c1=O] | 5-(3-{2-tert-butyl-6-oxo-4H,5H,6H-thieno[2,3-c]pyrrol-5-yl}-4-fluoro-2-(hydroxymethyl)phenyl)-1-methyl-3-(pyridin-2-ylamino)-1,2-dihydropyridin-2-one | 519.1 | |
| 143 | 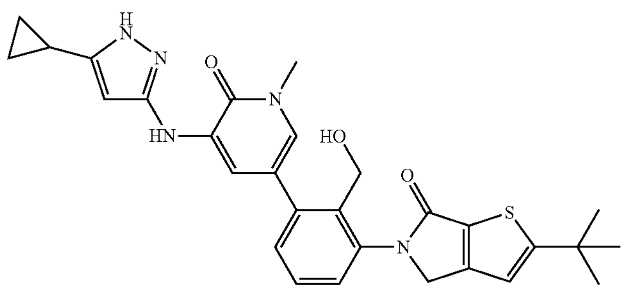 [SMILES: Cn1cc(-c2cccc(N3Cc4cc(C(C)(C)C)sc4C3=O)c2CO)cc(Nc2cc(C3CC3)[nH]n2)c1=O] | 5-(3-{2-tert-butyl-6-oxo-4H,5H,6H-thieno[2,3-c]pyrrol-5-yl}-2-(hydroxymethyl)phenyl)-3-[(5-cyclopropyl-1H-pyrazol-3-yl)amino]-1-methyl-1,2-dihydropyridin-2-one | 530.1 | |
| 144 | 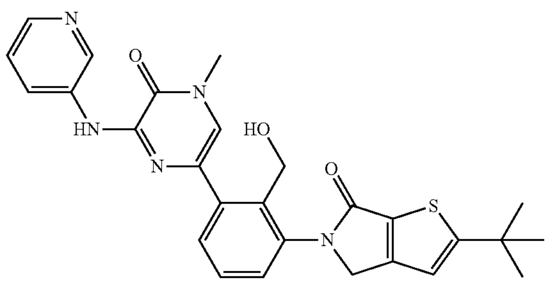 [SMILES: Cn1cc(-c2cccc(N3Cc4cc(C(C)(C)C)sc4C3=O)c2CO)nc(Nc2cccnc2)c1=O] | 5(3-{2-tert-butyl-6-oxo-4H,5H,6H-thieno[2,3-c]pyrrol-5-yl}-2-(hydroxymethyl)phenyl)-1-methyl-3-(pyridin-3-ylamino)-1,2-dihydropyrazin-2-one | 502.1 | |
| 145 | 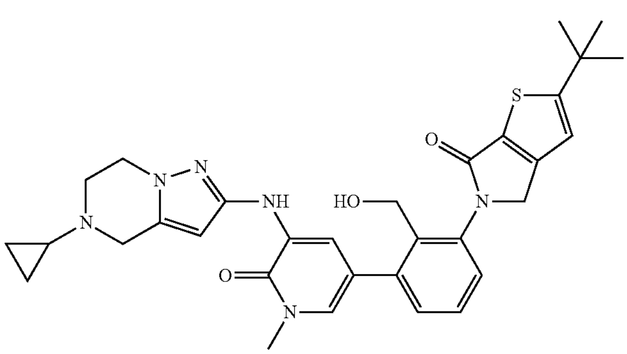 [SMILES: Cn1cc(-c2cccc(N3Cc4cc(C(C)(C)C)sc4C3=O)c2CO)cc(Nc2cc3n(n2)CCN(C2CC2)C3)c1=O] | 5-(3-{2-tert-butyl-6-oxo-4H,5H,6H-thieno[2,3-c]pyrrol-5-yl}-2-(hydroxymethyl)phenyl)-3-({5-cyclopropyl-4H,5H,6H,7H-pyrazolo[1,5-a]pyrazin-2-yl}amino)-1-methyl-1,2-dihydropyridin-2-one | 585.2 | |

TABLE 2-continued

| No | Structure | Name | M + H m/z | Btk IC$_{50}$ (μMol) |
|---|---|---|---|---|
| 146 | 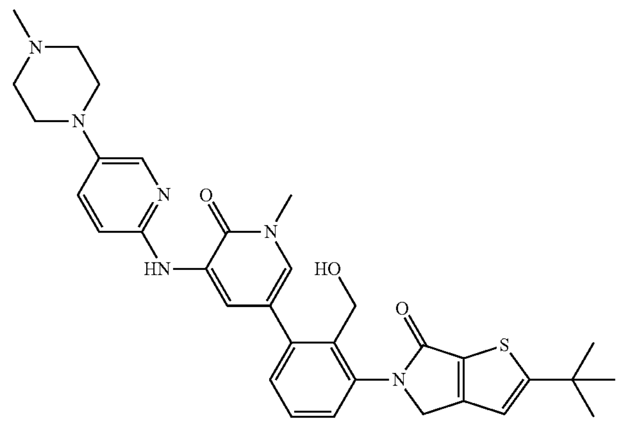 [SMILES: CN1CCN(c2ccc(Nc3cc(-c4cccc(N5Cc6cc(C(C)(C)C)sc6C5=O)c4CO)cn(C)c3=O)nc2)CC1] | 5-(3-{2-tert-butyl-6-oxo-4H,5H,6H-thieno[2,3-c]pyrrol-5-yl}-2-(hydroxymethyl)phenyl)-1-methyl-3-{[5-(4-methylpiperazin-1-yl)pyridin-2-yl]amino}-1,2-dihydropyridin-2-one | 599.3 | |
| 147 | 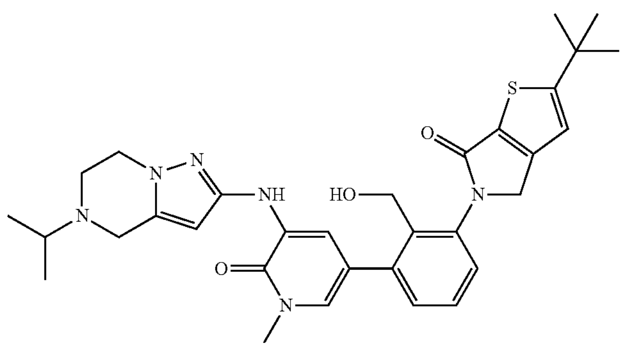 [SMILES: CC(C)N1CCn2nc(Nc3cc(-c4cccc(N5Cc6cc(C(C)(C)C)sc6C5=O)c4CO)cn(C)c3=O)cc2C1] | 5-(3-{2-tert-butyl-6-oxo-4H,5H,6H-thieno[2,3-c]pyrrol-5-yl}-2-(hydroxymethyl)phenyl)-1-methyl-3-{[5-(propan-2-yl)-4H,5H,6H,7H-pyrazolo[1,5-a]pyrazin-2-yl]amino}-1,2-dihydropyridin-2-one | 587.3 | |
| 148 | 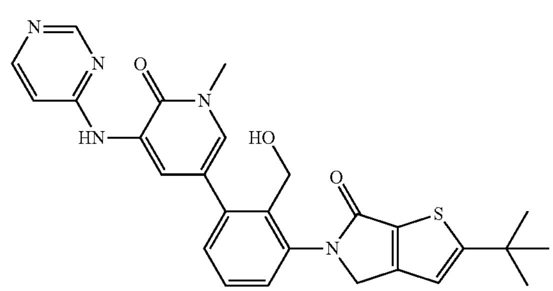 [SMILES: Cn1cc(-c2cccc(N3Cc4cc(C(C)(C)C)sc4C3=O)c2CO)cc(Nc2ccncn2)c1=O] | 5-(3-{2-tert-butyl-6-oxo-4H,5H,6H-thieno[2,3-c]pyrrol-5-yl}-2-(hydroxymethyl)phenyl)-1-methyl-3-(pyrimidin-4-ylamino)-1,2-dihydropyridin-2-one | 502.1 | |
| 149 | 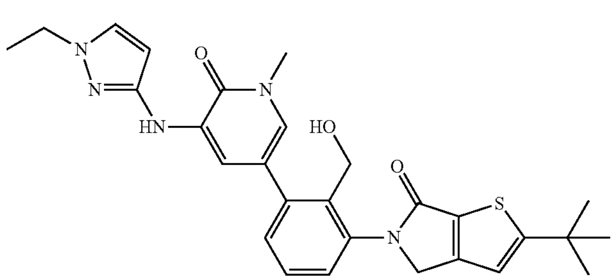 [SMILES: CCn1ccc(Nc2cc(-c3cccc(N4Cc5cc(C(C)(C)C)sc5C4=O)c3CO)cn(C)c2=O)n1] | 5-(3-{2-tert-butyl-6-oxo-4H,5H,6H-thieno[2,3-c]pyrrol-5-yl}-2-(hydroxymethyl)phenyl)-3-[(1-ethyl-1H-pyrazol-3-yl)amino]-1-methyl-1,2-dihydropyridin-2-one | 518.2 | |

TABLE 2-continued

| No | Structure | Name | M + H m/z | Btk IC50 (μMol) |
|---|---|---|---|---|
| 150 | 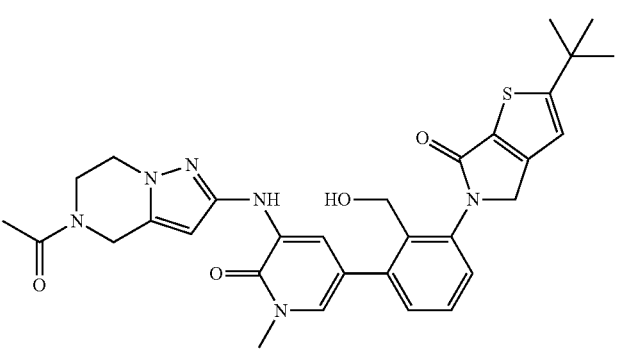 [SMILES: CC(=O)N1CCn2nc(Nc3cc(-c4cccc(N5Cc6cc(C(C)(C)C)sc6C5=O)c4CO)cn(C)c3=O)cc2C1] | 5-(3-{2-tert-butyl-6-oxo-4H,5H,6H-thieno[2,3-c]pyrrol-5-yl}-2-(hydroxymethyl)phenyl)-3-({5-acetyl-4H,5H,6H,7H-pyrazolo[1,5-a]pyrazin-2-yl}amino)-1-methyl-1,2-dihydropyridin-2-one | 587.2 | |
| 151 | 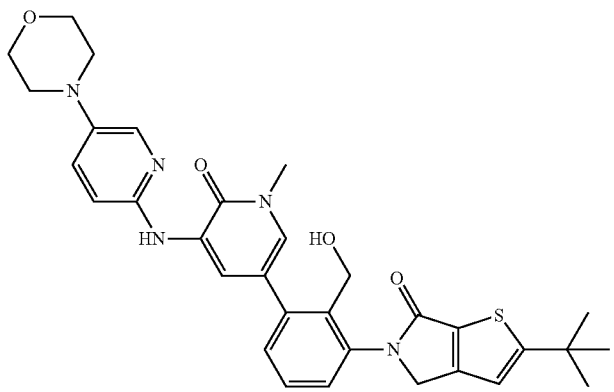 [SMILES: Cn1cc(-c2cccc(N3Cc4cc(C(C)(C)C)sc4C3=O)c2CO)cc(Nc2ccc(N3CCOCC3)cn2)c1=O] | 5-(3-{2-tert-butyl-6-oxo-4H,5H,6H-thieno[2,3-c]pyrrol-5-yl}-2-(hydroxymethyl)phenyl)-1-methyl-3-{[5-(morpholin-4-yl)pyridin-2-yl]amino}-1,2-dihydropyridin-2-one | 586.2 | |
| 152 | 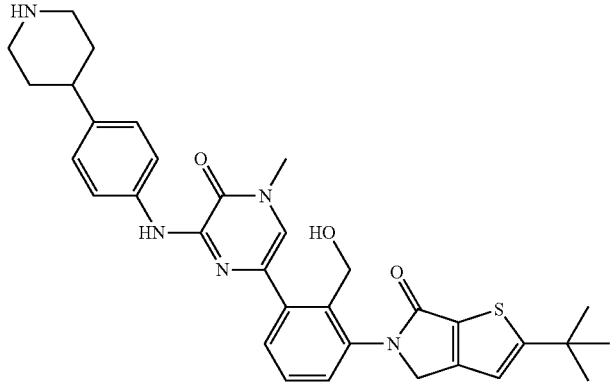 | 5-(3-{2-tert-butyl-6-oxo-4H,5H,6H-thieno[2,3-c]pyrrol-5-yl}-2-(hydroxymethyl)phenyl)-1-methyl-3-{[4-(piperidin-4-yl)phenyl]amino}-1,2-dihydropyrazin-2-one | 584.3 | |
| 153 | 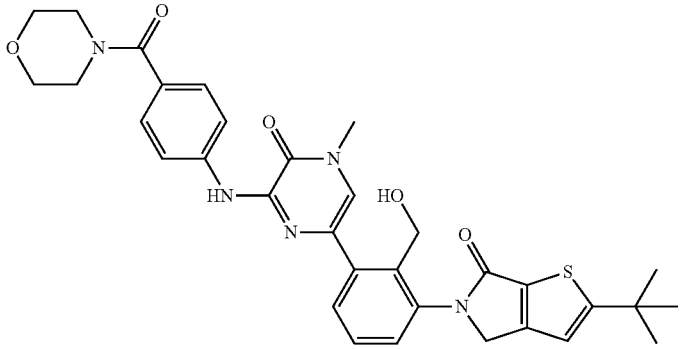 [SMILES: Cn1cc(-c2cccc(N3Cc4cc(C(C)(C)C)sc4C3=O)c2CO)nc(Nc2ccc(C(=O)N3CCOCC3)cc2)c1=O] | 5-(3-{2-tert-butyl-6-oxo-4H,5H,6H-thieno[2,3-c]pyrrol-5-yl}-2-(hydroxymethyl)phenyl)-1-methyl-3-{[4-(morpholin-4-ylcarbonyl)phenyl]amino}-1,2-dihydropyrazin-2-one | 614.2 | |

TABLE 2-continued

| No | Structure | Name | M + H m/z | Btk IC$_{50}$ (μMol) |
|---|---|---|---|---|
| 154 | 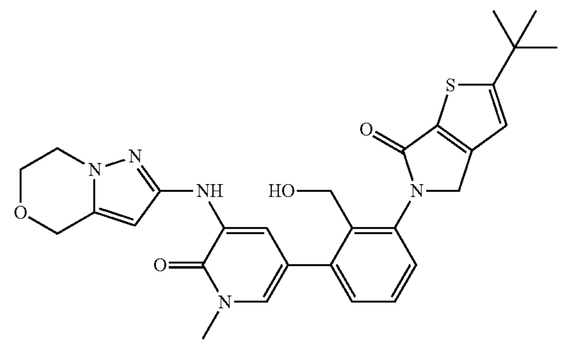 [SMILES: Cn1cc(-c2cccc(N3Cc4cc(C(C)(C)C)sc4C3=O)c2CO)cc(Nc2cc3n(n2)CCOC3)c1=O] | 5-(3-{2-tert-butyl-6-oxo-4H,5H,6H-thieno[2,3-c]pyrrol-5-yl}-2-(hydroxymethyl)phenyl)-1-methyl-3-{4H,6H,7H-pyrazolo[3,2-c][1,4]oxazin-2-ylamino}-1,2-dihydropyridin-2-one | 581.3 | |
| 155 | 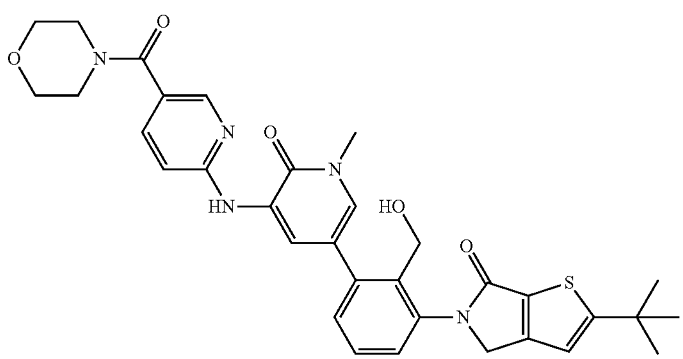 [SMILES: Cn1cc(-c2cccc(N3Cc4cc(C(C)(C)C)sc4C3=O)c2CO)cc(Nc2ccc(C(=O)N3CCOCC3)cn2)c1=O] | 5-(3-{2-tert-butyl-6-oxo-4H,5H,6H-thieno[2,3-c]pyrrol-5-yl}-2-(hydroxymethyl)phenyl)-1-methyl-3-{[5-(morpholin-4-ylcarbonyl)pyridin-2-yl]amino}-1,2-dihydropyridin-2-one | 614.3 | |
| 156 | 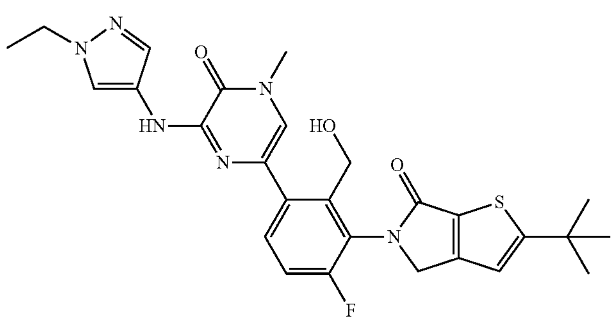 [SMILES: CCn1cc(Nc2nc(-c3ccc(F)c(N4Cc5cc(C(C)(C)C)sc5C4=O)c3CO)cn(C)c2=O)cn1] | 5-(3-{2-tert-butyl-6-oxo-4H,5H,6H-thieno[2,3-c]pyrrol-5-yl}-4-fluoro-2-(hydroxymethyl)phenyl)-3-[(1-ethyl-1H-pyrazol-4-yl)amino]-1-methyl-1,2-dihydropyrazin-2-one | 537.2 | |
| 157 | 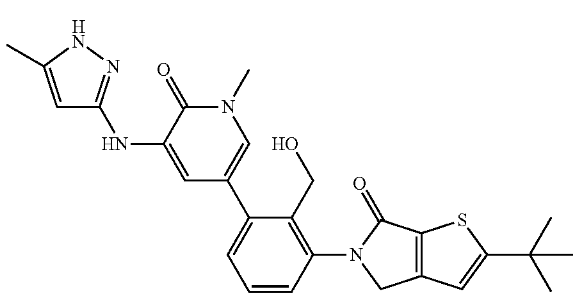 [SMILES: Cc1cc(Nc2cc(-c3cccc(N4Cc5cc(C(C)(C)C)sc5C4=O)c3CO)cn(C)c2=O)n[nH]1] | 5-(3-{2-tert-butyl-6-oxo-4H,5H,6H-thieno[2,3-c]pyrrol-5-yl}-2-(hydroxymethyl)phenyl)-1-methyl-3-[(5-methyl-1H-pyrazol-3-yl)amino]-1,2-dihydropyridin-2-one | 504.1 | |

TABLE 2-continued

| No | Structure | Name | M + H m/z | Btk IC$_{50}$ (μMol) |
|---|---|---|---|---|
| 158 | 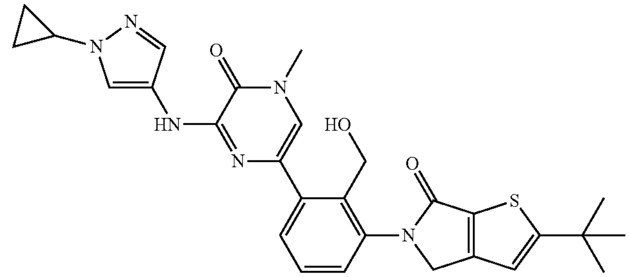 [SMILES: Cn1cc(-c2cccc(N3Cc4cc(C(C)(C)C)sc4C3=O)c2CO)nc(Nc2cnn(C3CC3)c2)c1=O] | 5-(3-{2-tert-butyl-6-oxo-4H,5H,6H-thieno[2,3-c]pyrrol-5-yl}-2-(hydroxymethyl)phenyl)-3-[(1-cyclopropyl-1H-pyrazol-4-yl)amino]-1-methyl-1,2-dihydropyrazin-2-one | 531.2 | |
| 159 | 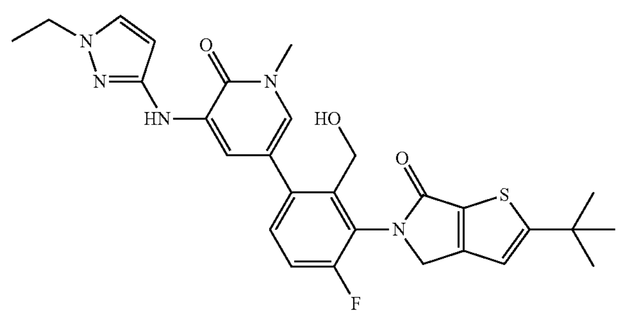 [SMILES: CCn1ccc(Nc2cc(-c3ccc(F)c(N4Cc5cc(C(C)(C)C)sc5C4=O)c3CO)cn(C)c2=O)n1] | 5(3-{2-tert-butyl-6-oxo-4H,5H,6H-thieno[2,3-c]pyrrol-5-yl}-4-fluoro-2-(hydroxymethyl)phenyl)-3-[(1-ethyl-1H-pyrazol-3-yl)amino]-1-methyl-1,2-dihydropyridin-2-one | 536.2 | |
| 160 | 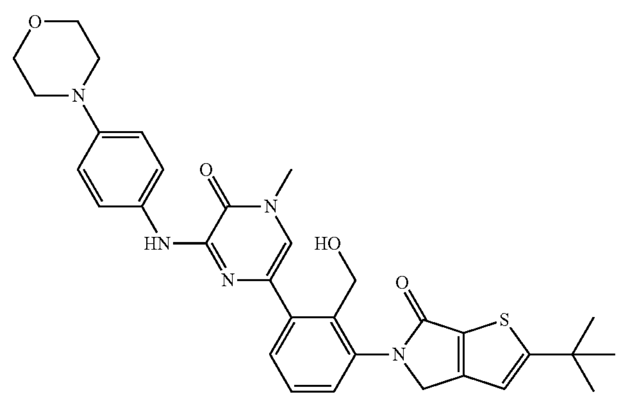 [SMILES: Cn1cc(-c2cccc(N3Cc4cc(C(C)(C)C)sc4C3=O)c2CO)nc(Nc2ccc(N3CCOCC3)cc2)c1=O] | 5-(3-{2-tert-butyl-6-oxo-4H,5H,6H-thieno[2,3-c]pyrrol-5-yl}-2-(hydroxymethyl)phenyl)-1-methyl-3-{[4-(morpholin-4-yl)phenyl]amino}-1,2-dihydropyrazin-2-one | 586.2 | |
| 161 | 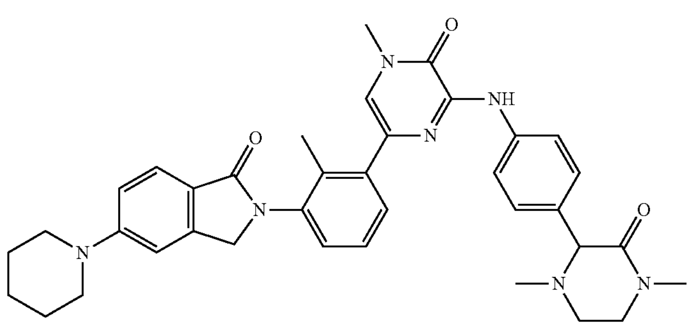 [SMILES: Cc1c(-c2cn(C)c(=O)c(Nc3ccc(C4C(=O)N(C)CCN4C)cc3)n2)cccc1N1Cc2cc(N3CCCCC3)ccc2C1=O] | 2-[3-(6-{[4-(1,4-dimethyl-3-oxopiperazin-2-yl)phenyl]amino}-4-methyl-5-oxo-4,5-dihydropyrazin-2-yl)-2-methylphenyl]-5-(piperidin-1-yl)-2,3-dihydro-1H-isoindol-1-one | 631.58 | 0.245 |
| 162 | 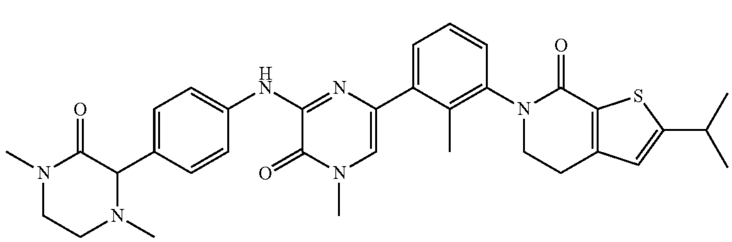 [SMILES: Cc1c(-c2cn(C)c(=O)c(Nc3ccc(C4C(=O)N(C)CCN4C)cc3)n2)cccc1N1CCc2cc(C(C)C)sc2C1=O] | 3-{[4-(1,4-dimethyl-3-oxopiperazin-2-yl)phenyl]amino}-1-methyl-5-{2-methyl-3-[7-oxo-2-(propan-2-yl)-4H,5H,6H,7H-thieno[2,3-c]pyridin-6-yl]phenyl}-1,2-dihydropyrazin-2-one | 611.08 | |

TABLE 2-continued

| No | Structure | Name | M + H m/z | Btk IC$_{50}$ (μMol) |
|---|---|---|---|---|
| 163 | 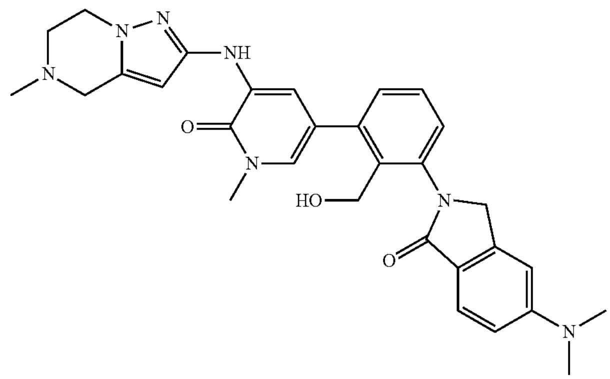 | 5-(dimethylamino)-2-[2-(hydroxymethyl)-3-[1-methyl-5-({5-methyl-4H,5H,6H,7H-pyrazolo[1,5-a]pyrazin-2-yl}amino)-6-oxo-1,6-dihydropyridin-3-yl]phenyl]-2,3-dihydro-1H-isoindol-1-one | 540.3 | |
| 164 | 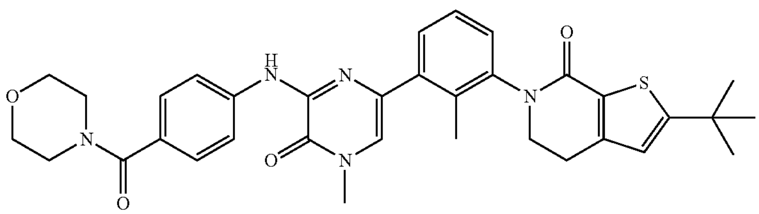 [SMILES: Cc1c(-c2cn(C)c(=O)c(Nc3ccc(C(=O)N4CCOCC4)cc3)n2)cccc1N1CCc2cc(C(C)(C)C)sc2C1=O] | 5-(3-{2-tert-butyl-7-oxo-4H,5H,6H,7H-thieno[2,3-c]pyridin-6-yl}-2-methylphenyl)-1-methyl-3-{[4-(morpholin-4-ylcarbonyl)phenyl]amino}-1,2-dihydropyrazin-2-one | 612.4 | |

Administration of Formula I Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with Btk kinase such as an immune disorder, cardiovascular disease, viral infection, inflammation, cancer, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Formula I compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Methods of the invention also include treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjogren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, myeloid leukemia, oral cavity and pharynx, non-Hodgkin lymphoma, melanoma, and villous colon adenoma.

The methods of the invention can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of Btk activity may result in reduced amounts of reperfusion injury in such situations.

Pharmaceutical Formulations

In order to use a compound of this invention for the therapeutic treatment of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with a second therapeutic compound that has anti-inflammatory or anti-hyperproliferative properties or that is useful for treating an inflammation, immune-response disorder, or hyperproliferative disorder (e.g., cancer). The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, solvate, metabolite, or pharmaceutically acceptable salt or prodrug thereof, and the use of at least one other cancer treatment method. The amounts of the compound(s) of Formula I and the other pharmaceutically active therapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The Figures and Examples provide exemplary methods for preparing Formula I compounds. Those skilled in the art will appreciate that other synthetic routes may be used to synthesize the Formula I compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

General Procedure A

Suzuki Coupling

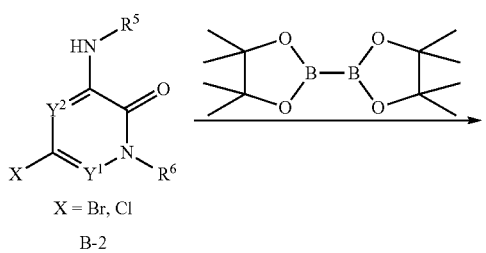

X = Br, Cl

B-2

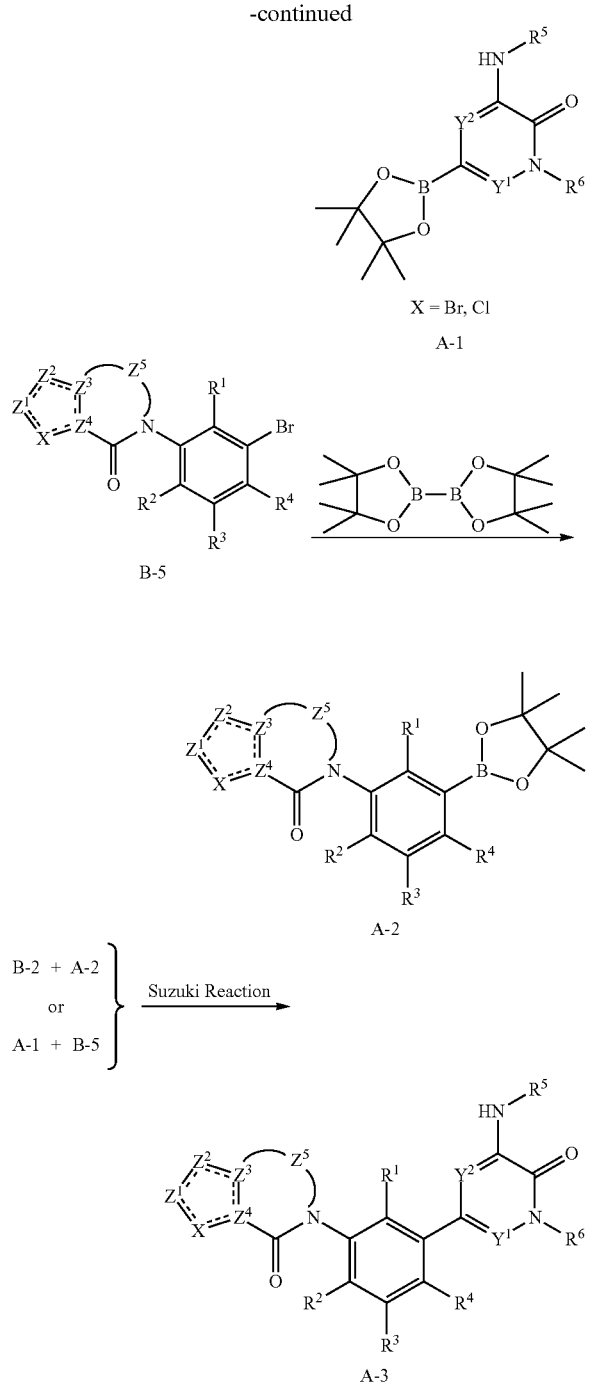

such as bis(triphenylphosphine)palladium(II) dichloride, is added. In some cases potassium acetate is used in place of sodium carbonate to adjust the pH of the aqueous layer. The reaction is then heated to about 140-150° C. under pressure in a microwave reactor such as the Biotage Optimizer (Biotage, Inc.) for 10 to 30 minutes. The contents are extracted with ethyl acetate, or another organic solvent. After evaporation of the organic layer the boron ester A-1 may be purified on silica or by reverse phase HPLC. Substituents $Y^1$, $Y^2$, $R^5$ and $R^6$ are as defined, or protected forms or precursors thereof. Likewise, bromide intermediate B-5 can be boronylated to give A-2. Substituents $Y^1$, $Y^2$, $R^1$, $R^2$, $R^3$, $R^4$, $Z^1$, $A^2$, $Z^3$, $Z^4$, and X are as defined, or protected forms or precursors thereof.

Suzuki coupling of B-2 and A-2, or of A-1 and B-5, gives Formula I compound or intermediate A-3. Boronic ester (or acid) (1.5 eq) A-1 or A-2, and a palladium catalyst such as bis(triphenylphosphine)palladium(II) chloride (0.05 eq) is added to a mixture of halo intermediate (1 eq) B-2 or B-5 in acetonitrile and 1 M of sodium carbonate aqueous solution (equal volume as acetonitrile). The reaction mixture is heated to about 150° C. in a microwave for about 15 min. LC/MS indicates when the reaction is complete. Water is added to the mixture, and the precipitated product is filtered and purified by HPLC to yield the product A-3. Substituents $R^{1'}$, $R^{2'}$, $R^{4'}$ may be $R^1$, $R^2$, $R^4$ as defined, or protected forms or precursors thereof.

A variety of palladium catalysts can be used during the Suzuki coupling step. Various low valent, Pd(II) and Pd(0) catalysts may be used in the Suzuki coupling reaction, including PdCl2(PPh$_3$)$_2$, Pd(t-Bu)$_3$, PdCl$_2$ dppf CH$_2$Cl$_2$, Pd(PPh$_3$)$_4$, Pd(OAc)/PPh$_3$, Cl$_2$Pd[(Pet$_3$)]$_2$, Pd(DIPHOS)$_2$, Cl$_2$Pd(Bipy), [PdCl(Ph$_2$PCH$_2$PPh$_2$)]$_2$, Cl$_2$Pd[P(o-tol)$_3$]$_2$, Pd$_2$(dba)$_3$/P(o-tol)$_3$, Pd$_2$(dba)/P(furyl)$_3$, Cl$_2$Pd[P(furyl)$_3$]$_2$, Cl$_2$Pd(PMePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, Cl$_2$Pd[P(4-COOH-Ph)(Ph)$_2$]$_2$, and encapsulated catalysts Pd EnCat™ 30, Pd EnCat™ TPP30, and Pd(II)EnCat™ BINAP30 (US 2004/0254066).

General Procedure B

Buchwald reaction

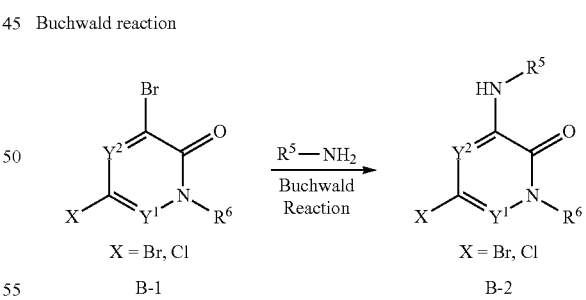

The Suzuki-type coupling reaction is useful to form carbon-carbon bonds to attach the rings of Formula I compounds and intermediates such as A-3 (Suzuki (1991) Pure Appl. Chem. 63:419-422; Miyaura and Suzuki (1979) Chem. Reviews 95(7):2457-2483; Suzuki (1999) J. Organometal. Chem. 576:147-168). Suzuki coupling is a palladium mediated cross coupling reaction of an arylhalide, such as B-2 or B-5, with a boronic acid such as A-1 or A-2. For example, B-2 may be combined with about 1.5 equivalents of 4,4,4',4',5,5,5',5'-octamethyl-2,2'-bi(1,3,2-dioxaborolane), and dissolved in about 3 equivalents of sodium carbonate as a 1 molar solution in water and an equal volume of acetonitrile. A catalytic amount, or more, of a low valent palladium reagent, The Buchwald reaction is useful to aminate 6-bromo intermediates B-1 (Wolf and Buchwald (2004) Org. Synth Coll. Vol. 10:423; Paul et al (1994) Jour. Amer. Chem. Soc. 116: 5969-5970). To a solution of halo intermediate B-1 in DMF is added the appropriate amine $R^5$—NH$_2$ (200 mol %), Cs$_2$CO$_3$ (50 mol %), Pd$_2$(dba)$_3$ (5 mol %), and XANTPHOS (10 mol %). The reaction is heated to about 110° C. under pressure in a Biotage optimizer microwave reactor for about 30 min. The resulting solution is concentrated in vacuo to give B-2. Other palladium catalysts and phosphine ligands may be useful.

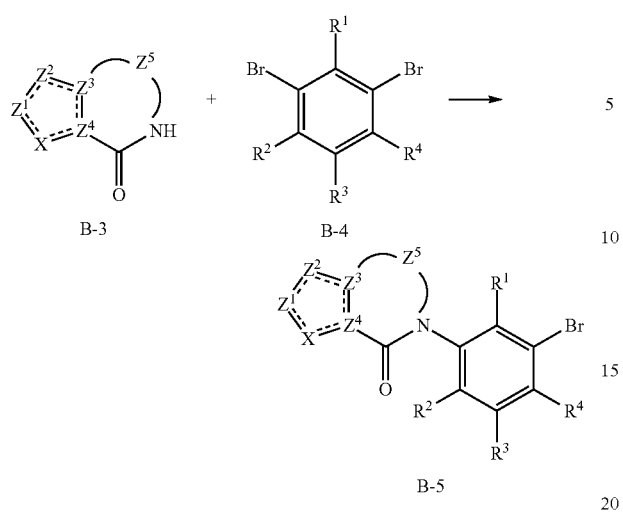

N-Aryl amide intermediates B-5 can also be prepared under Buchwald conditions with cyclic amide intermediates B-3 and aryl bromides B-4.

FIG. 1 shows an exemplary synthetic route to make Formula I compounds 8 which involves a Buchwald reaction to couple a bicyclic pyrolone 4 with a methyl or hydroxymethyl benzene 5 to yield intermediate 6, followed by either successive Suzuki reactions to prepare a boronate 7 and couple it with a bromo-pyridone or -pyrazinone 2, or a single Suzuki reaction to couple 6 with a pyridone- or pyrazinone-boronate 3. Bromo-pyridone or -pyrazinone 2 can be prepared by a Buchwald reaction of a dibromo-pyridone or -pyrazinone with a heterocyclic amine or an aniline. Pyridone- or pyrazinone-boronates 3 can be prepared by a Suzuki reactions of 2 with a diboronate.

Figure 2:
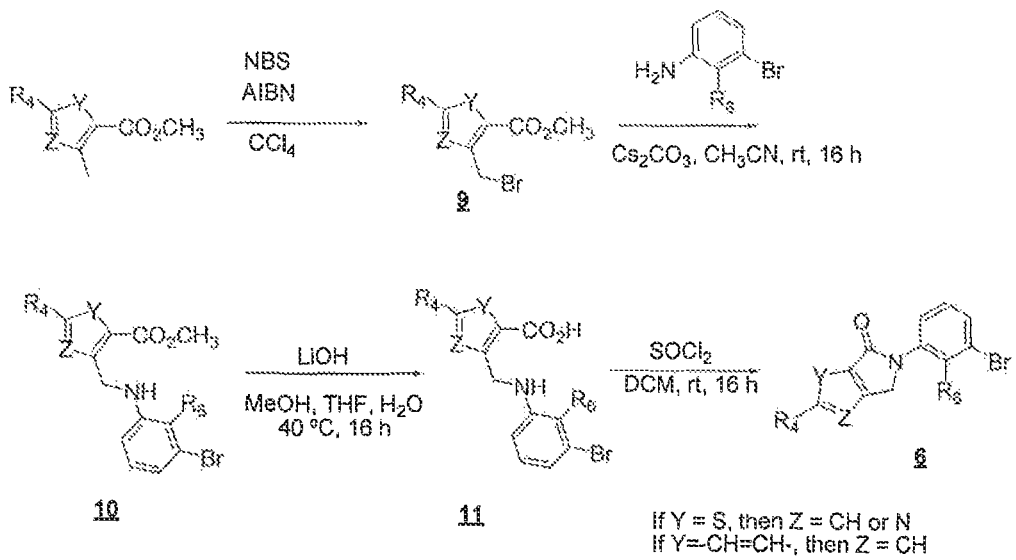
FIG. 2 shows an exemplary synthetic route to make Formula I compounds 8 involving assembling the bicyclic pyrolone on a bromoaniline derivative to afford a bromide which can be used in the roles dileneated in FIG. 1.

FIG. 2 shows an exemplary synthetic route to make Formula I compounds 8 involving assembling the bicyclic pyrolone on a bromoaniline derivative to afford a bromide which can be used in the roles dileneated in FIG. 1.

Figure 3:
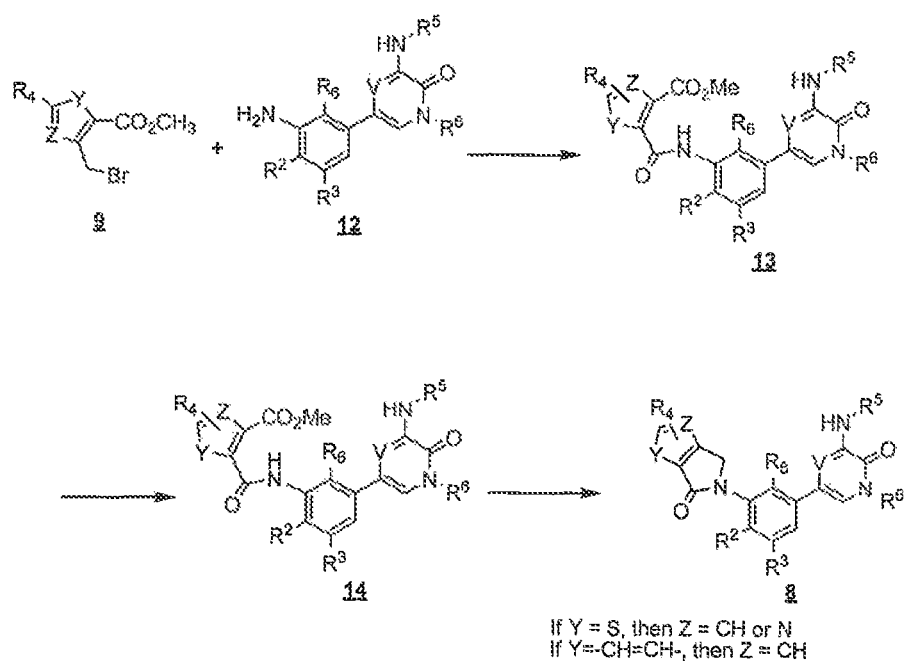
FIG. 3 shows an exemplary synthetic route to make Formula I compounds 8 involving assembling the bicyclic pyrolone on the amino derivative of the rest of the molecule 12.

FIG. 3 shows an exemplary synthetic route to make Formula I compounds 8 involving assembling the bicyclic pyrolone on the amino derivative of the rest of the molecule 12.

EXAMPLES

Example 101

Example 101a 4-tert-Butyl-2-methylbenzoic Acid 101a

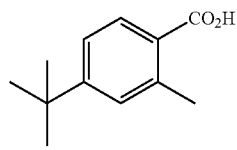

A 250 mL round bottom flask was charged with tetramethylethylene diamine (5.6 mL, 37 mmol) in THF (34 mL). After the mixture was cooled to −92° C. (N$_{2(liq)}$/CH$_2$Cl$_2$ bath), sec-BuLi (26.5 mL, 37 mmol, 1.4M solution in cyclohexane) was added, followed by the dropwise addition of a solution of 4-tert-butylbenzoic acid (3 g, 16.8 mmol) dissolved in THF (22 mL). After stirring for 1 h, methyliodide (4.5 mL, 72.4 mmol) was added to mixture at −80° C. After stirring for 10 min at −80° C., the reaction mixture was quenched H$_2$O (20 mL). Upon warming to room temperature, the aqueous phase adjusted to pH=2 with aqueous HCl (1M). The aqueous phase was extracted with EtOAc (2×15 mL), and the combined organic extracts were dried with Na$_2$SO$_4$ and concentrated. The residue was chromatographed with (gradient, 10%-60% EtOAc/hexanes) to afford 630 mg (20%) 101a.

Example 101b

Ethyl 4-tert-Butyl-2-methylbenzoate 101b

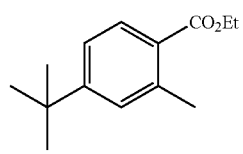

To a 100 mL round bottom flask was charged with acid 101a (630 mg, 3.3 mmol) in CH$_2$Cl$_2$ (20 mL) was added oxalyl chloride (4.9 mL, 9.8 mmol, 2.0M solution in CH$_2$Cl$_2$) followed by DMF (1 drop). After the reaction was stirred at room temperature for 8 h, it was concentrated. To the residue was added Et$_2$O (25 mL) and the mixture was concentrated. This repeated to removed any excess oxalyl chloride. The residue was dissolved in CH$_2$Cl$_2$ (15 mL) and EtOH (15 mL). After the reaction was stirred at room temperature for 30 min, it was concentrated. The residue was dissolved in EtOAc (15 mL) and this organic phase was washed with aqueous HCl (15 mL, 1M), H$_2$O (15 mL), brine (15 mL), dried with Na$_2$SO$_4$ and concentrated. The crude 101b (660 mg, 91%) was used without further purification.

Example 101c

Ethyl 2-(Bromomethyl)-4-tert-butylbenzoate 101c

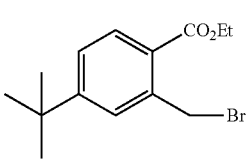

To 100 mL round bottom flask charged with ester 101b (230 mg, 1.04 mmol), N-bromosuccinimide (214 mg, 1.2 mmol), benzoyl peroxide (25 mg, 0.1 mmol) in benzene (5 mL). After the mixture was stirred at reflux for 4 h, H$_2$O (10 mL) was added. The aqueous phase was extracted with CH$_2$Cl$_2$ (2×10 mL), and the combined organic extracts were washed with brine (10 mL), dried with Na₂SO₄ and concentrated. The crude 101c (287 mg, 92%) was used without further purification.

Example 101d

5-Bromo-1-methyl-3-[4-(morpholine-4-carbonyl)phenylamino]-1H-pyrazin-2-one 101d

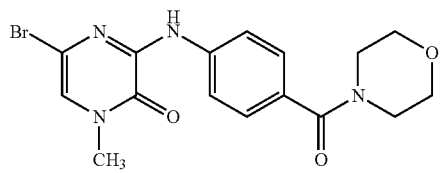

101d

A 250-mL single-neck round-bottomed flask equipped with a magnetic stirrer and reflux condenser was charged with 3,5-dibromo-1-methylpyrazin-2(1H)-one (*J. Heterocycl. Chem.* 1983, 20, 919) (21.8 g, 81.4 mmol), 4-aminobenzmorpholide (23.6 g, 114 mmol) and dimethyl-acetamide (130 mL). The reaction mixture was then heated under nitrogen at 105° C. for 14 h (Note: A spatula was used to break up the solids formed after 4 h of heating). After this time the suspension was cooled to room temperature, poured into stirring water (1.5 L) and filtered. The resulting precipitate was washed with water (2×250 mL) and allowed to partially dry on the filter paper for 10-15 minutes. After this time the filter cake was washed with hot ethyl acetate (2×250 mL), followed by hot ethanol (250 mL) and dried under reduced pressure to afford a 63% yield (24.3 g) of 101d as a light orange solid: mp 276-277° C.; $^1$H NMR (500 MHz, CDCl₃) δ 8.39 (bs, 1H), 7.81 (dd, 2H, J=9.0, 2.0 Hz), 7.45 (dd, 2H, J=9.0, 2.0 Hz), 6.81 (s, 1H), 3.71 (m, 8H), 3.55 (s, 3H); MS (ESI+) m/z 393 (M+H).

Example 101e 4,4,5,5-Tetramethyl-2-(2-methyl-3-nitro-phenyl)-[1,3,2]dioxaborolane 101e

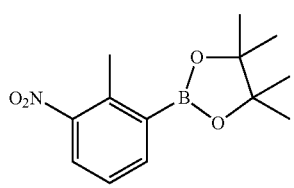

101e

A 1-L three-neck round-bottomed flask equipped with a mechanical stirrer and thermoregulator was purged with nitrogen and charged with 2-bromo-6-nitrotoluene (60.2 g; 278 mmol), 4,4,4',4',5,5,5',5'-octamethyl-2,2'-bi(1,3,2-dioxaborolane) (85.2 g; 336 mmol), potassium acetate (82.4 g; 840 mmol) and DMSO (320 mL). A stream of nitrogen was passed through the resulting suspension for 30 min, [1,1'-bis(diphenyl-phosphino)-ferrocene]dichloropalladium (II), complex with dichloromethane (1:1) (7.60 g; 9.30 mmol) was then added and the reaction heated at 85° C. for 20 h. After this time the mixture was cooled to ambient temperature, poured into a mixture of water (1300 mL) and methyl t-butyl ether (500 mL) and treated with Cellpure P65 (150 cc). The resulting suspension was filtered through a pad of Cellpure P65 (200 cc) packed onto a fritted funnel (ID 185 mm). The filter cake was washed with MtBE (3×180 mL) and the organic layer of the filtrate separated, washed with water (3×1 L) and dried over sodium sulfate. After filtering off sodium sulfate, the filtrate was concentrated and purified by flash chromatography to afford 4,4,5,5-tetramethyl-2-(2-methyl-3-nitro-phenyl)-[1,3,2]dioxaborolane 101e as a light yellow solid: mp 52-53° C.; MS (APCI+) m/z 264 (M+H).

Example 101f

2-Methyl-3-(4,4,5,5-tetramethyl-[1,3,2]dioxaborolan-2-yl)-phenyl-amine 101f

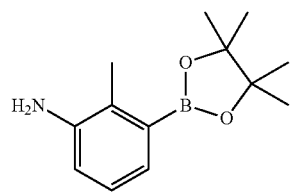

101f

A 500-mL round-bottomed flask equipped with a magnetic stirrer was charged with 4,4,5,5-Tetramethyl-2-(2-methyl-3-nitro-phenyl)-[1,3,2]dioxaborolane 101e (8.44 g; 32.1 mmol) and methanol (150 mL). The reaction flask was twice evacuated and back-filled with argon. 10% Palladium on charcoal (50% wet, 425 mg dry weight) was then added to the solution, and the reaction flask evacuated and back-filled with hydrogen three times. The reaction was then stirred under balloon pressure of hydrogen at room temperature for 13 h. After this time, the flask was twice evacuated and back-filled with argon, then filtered through a pad of Celite 521 and the filtrate concentrated in vacuo. The resulting residue was dried under high vacuum for 1 d to afford a quantitative yield (8.16 g) of 2-methyl-3-(4,4,5,5-tetramethyl-[1,3,2]dioxaborolan-2-yl)-phenylamine 101f as a white solid: mp 110-112° C.; MS (ESI+) m/z 234 (M+H).

Example 101g 5-(3-Amino-2-methylphenyl)-1-methyl-3-[4-(morpholine-4-carbonyl)-phenylamino]-1H-pyrazin-2-one 101g

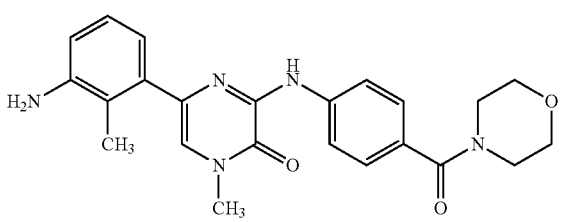

101g

A 250-mL single-neck round-bottomed flask equipped with a magnetic stirrer and reflux condenser was charged with 101d (9.23 g, 23.5 mmol), 1,4-dioxane (250 mL) and aqueous 0.71 M sodium carbonate (50 mL, 35.5 mmol). After bubbling argon through the resulting solution for 15 minutes, 101f (6.58 g, 28.2 mmol) and tetrakis(triphenylphosphine)palladium (4.06 g, 3.51 mmol) were added and the reaction mixture then heated at 100° C. for 38 h. After this time the reaction was cooled to room temperature and partitioned between water (1 L) and methylene chloride (300 mL). The aqueous phase was separated and re-extracted with methylene chloride (2×300 mL). A white precipitate of the product present in the combined organic extracts was filtered and retained. The organic phase was extracted with 2N hydrochloric acid (2×200 mL) and then discarded. The acidic aqueous phase was made basic with 2N sodium hydroxide to pH 8-10 and extracted with methylene chloride (3×300 mL). The combined organic extracts were dried over sodium sulfate, filtered, then combined with the white precipitate (vide supra) and concentrated under reduced pressure. The resulting white solid was triturated with hot ethanol (100 mL), filtered, and washed with ethanol (2×40 mL). The filter cake was dissolved in chloroform, the solution was concentrated under reduced pressure and dried to a constant weight under high vacuum at 50° C. to afford an 84% yield of 101g (8.31 g) as an off-white solid: mp 274-275° C.; $^1$H NMR (500 MHz, CDCl$_3$) δ 9.40 (s, 1H), 8.09 (d, 2H, J=8.5 Hz), 7.34 (d, 2H, J=8.5 Hz), 7.14 (s, 1H), 6.93 (t, 1H, J=7.5 Hz), 6.66 (d, 1H, J=7.5 Hz), 6.57 (d, 1H, J=7.5 Hz), 4.92 (bs, 2H), 3.58 (bs, 4H), 3.54 (s, 3H), 3.48 (bs, 4H), 2.09 (s, 3H); MS (ESI+) m/z 420 (M+H).

Example 101h

Ethyl 4-tert-Butyl-2-((2-methyl-3-(4-methyl-6-(4-(morpholine-4-carbonyl)phenyl amino)-5-oxo-4,5-dihydropyrazin-2yl)phenylamino)methyl)benzoate 101h

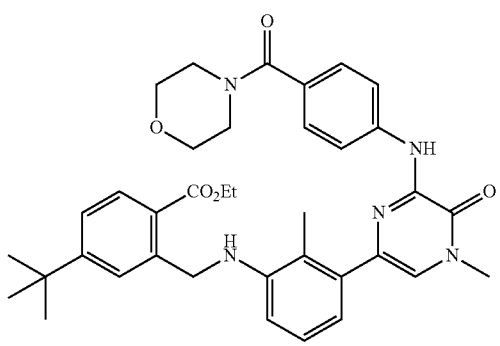

A 48-mL sealed tube equipped with a magnetic stirring bar was charged with bromide 101c (120 mg, 0.4 mmol), aniline 101g (168 mg, 0.4 mmol), diisopropyethylamine (0.08 mL, 0.48 mmol) in EtOH (3 mL). After the mixture was stirred at 100° C. for 16 h, aqueous Na$_2$CO$_3$ (5 mL) was added. The aqueous phase was extracted with EtOAc (2×5 mL), and the combined organic extracts were washed with brine (5 mL), dried with Na$_2$SO$_4$ and concentrated. The residue was chromatographed with (gradient, 50%-100% EtOAc/hexanes) to afford 100 mg (42%) of 101h.

Example 101i 4-tert-Butyl-2-((2-methyl-3-(4-methyl-6-(4-(morpholine-4-carbonyl)-phenylamino)-5-oxo-4,5-dihydropyrazin-2-yl)phenylamino)methyl)benzoic Acid 101i

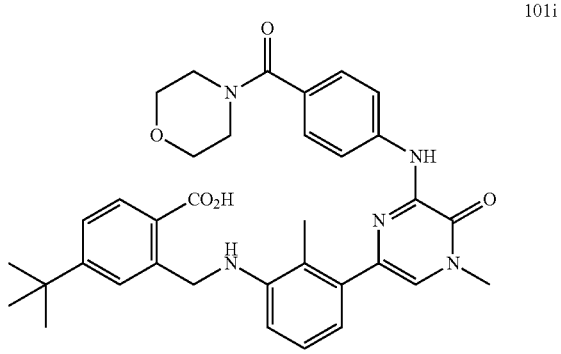 [SMILES: Cc1c(NCc2cc(C(C)(C)C)ccc2C(=O)O)cccc1-c1cn(C)c(=O)c(Nc2ccc(C(=O)N3CCOCC3)cc2)n1]

To 25 mL round bottom flask charged with ester 101h (100 mg, 0.16 mmol) and LiOH (20 mg, 0.47 mmol) in THF (2 mL), EtOH (2 mL) and H$_2$O (2 mL). After the mixture was stirred at 60° C. for 16 h, the pH was adjusted to 7 with aqueous 1M HCl. The aqueous phase was extracted with EtOAc (2×10 mL), and the combined organic extracts were washed with brine (10 mL), dried with Na$_2$SO$_4$ and concentrated. The crude 101i (97 mg, 99%) was used without further purification.

Example 101

5-tert-Butyl-2-(2-methyl-3-(4-methyl-6-(4-(morpholine-4-carbonyl)phenylamino)-5-oxo-4,5-dihydropyrazin-2-yl)phenyl)isoindolin-1-one 101

To 25 mL round bottom flask charged with acid 101i (97 mg, 0.16 mmol), diisopropyethylamine (0.08 mL, 0.48 mmol) in DMF (5 mL) was added (benzotriazol-1-yloxy)tris(dimethylamino)phosphonium hexafluorophosphate (84 mg, 0.19 mmol). After the reaction was stirred at room temperature for 2 h, H$_2$O (5 mL) and EtOAc (10 mL) were added. The organic phase was extracted with aqueous HCl (1M, 2×5 mL), H$_2$O (5 mL), aqueous Na$_2$CO$_3$ (1M, 5 mL), brine (5 mL), dried with Na$_2$SO$_4$ and concentrated. The residue was chromatographed (gradient, 0%-100% 60:35:5 CH$_2$Cl$_2$: Et$_2$O:MeOH/CH$_2$Cl$_2$) to afford 45 mg (48%) of 101. MH+ (m/z): 591.5. $^1$H NMR (300 MHz, CDCl$_3$) 6 m; 8.44 (s, 1 H), 8.39 (m, 1 H), 7.88 (s, 1 H), 7.82 (s, 1 H), 7.39-7.49 (m, 5 H), 7.31-7.35 (, 2 H), 7.07 (d, J=7.5 Hz, 1 H), 6.81 (s, 1 H), 6.58

(d, J=7.5 Hz, 1 H), 3.69 (broad s, 6 H), 3.62 (s, 3 H), 3.07 (m, 1 H), 2.21 (s, 3 H), 1.35 (s, 3 H), 1.33 (s, 3 H); MS (ESI+) m/z (M+H) 590.58.

Example 102

Example 102a

Methyl 3-Methylthiophene-2-carboxylate 102a

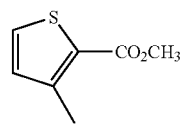

3-Methylthiophene-2-carbonyl chloride (1) (10 mL, 18 mmol) in 30 mL of methanol was heated to boiling under reflux for 18 hours, then concentrated in vaculo. The residue was partitioned between diethyl ether and water. The organic layer was dried with $Na_2SO_4$ and concentrated to afford 102a (12.12 g, 100%) as a clear oil, which was used without further purification.

Example 102b

Methyl 5-tert-Butyl-3-methylthiophene-2-carboxylate 102b

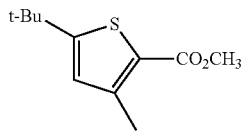

$AlCl_3$ (15.60 g, 117 mMol) was suspended in $CH_2Cl_2$ (18 mL) and the mixture was cooled to −78° C. A solution of 12.28 g (78 mMol) of 102a in $CH_2Cl_2$ (9 mL) was added dropwise over 5 min. The mixture was stirred for 5 min. A solution of 8.9 mL (82 mMol) 2-chloro-2-methylpropane in $CH_2Cl_2$ (9 mL) was then added over 45 min, and the resulting mixture was stirred at −78° C. for 1 h. The reaction mixture was gradually warmed to room temperature and stirred for 24 h. The reaction mixture was then poured onto ice and extracted with $CH_2Cl_2$. The organic layer was dried with $Na_2SO_4$, and concentrated to an oil, which was purified on silica eluting with a gradient of $CH_2Cl_2$ in Hexane (0 to 10%) to afford 9.94 g (60%) of 102b.

Example 102c

Methyl 3-(Bromomethyl)-5-tert-butylthiophene-2-carboxylate 102c

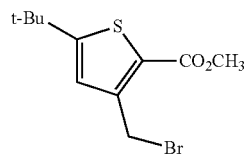

A mixture of 3.15 g (14.8 mMol) of 102b, 3.17 g (17.8 mMol) of N-bromo-succinimide, and 0.122 g (0.742 mmol) of 2,2'-azobisisobutyronitrile in 40 mL of carbon tetrachloride was heated at 85° C. overnight. The reaction mixture was cooled to room temperature, and filtered. The filtrate was concentrated in vacuo, and the resulting residue was purified on silica: ISCO 40 g column, 0 to 20% $CH_2Cl_2$ in hexane. Isolated was 3.0 g (70%) of 102c.

Example 102d

Methyl 3-((3-Bromo-2-methylphenylamino)methyl)-5-tert-butylthiophene-2-carboxylate 102d

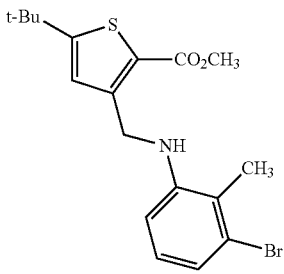 [SMILES: COC(=O)c1sc(C(C)(C)C)cc1CNc1cccc(Br)c1C]

A 250-mL single-necked round-bottomed flask equipped with a magnetic stirrer was purged with nitrogen and charged with 102c (1.09 g, 4.68 mmol), 3-bromo-2-methylaniline (2.61 g, 14.0 mmol) and acetonitrile (25 mL). Cesium carbonate (1.67 g, 5.15 mmol) was added and the mixture was stirred at room temperature for 16 h. The reaction mixture was then concentrated under reduced pressure. Purification of the resulting residue by column chromatography afforded a 70% yield (1.30 g) of 102d as a yellow oil: $^1H$ NMR (300 MHz, CDCl$_3$) δ 6.92 (m, 2H), 6.85 (s, 1H), 6.57 (dd, 1H, J=4.8, 2.1 Hz), 4.60 (s, 2H), 3.86 (s, 3H), 2.29 (s, 3H), 1.37 (s, 9H); MS (ESI+) m/z 396.2 (M+H).

Example 102e 3-((3-Bromo-2-methylphenylamino)methyl)-5-tert-butylthiophene-2-carboxylic Acid 102e

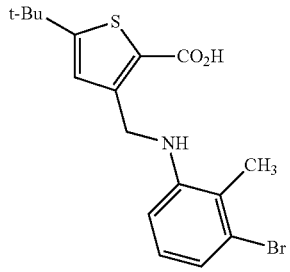 [SMILES: Cc1c(Br)cccc1NCc1cc(C(C)(C)C)sc1C(=O)O]

A 50-mL single-necked round-bottomed flask equipped with a magnetic stirrer was charged with 102d (1.30 g, 3.28 mmol), THF (5.0 mL), methanol (5.0 mL) and water (5.0 mL). Lithium hydroxide (1.38 g, 32.8 mmol) was added and the mixture was placed in a 40° C. oil bath. After 16 h the reaction mixture was cooled to room temperature and the volatiles removed under reduced pressure. The resulting aqueous solution was acidified with 2 N hydrochloric acid to pH of 4. The resulting solid was filtered off and dried in a vacuum oven at 40° C. affording a quantitative yield (1.25 g) of 102e as a white solid: mp 150-152° C.; $^1$H NMR (300 MHz, DMSO-d$_6$) δ 6.85 (t, 1H, J=7.8 Hz), 6.75-6.67 (m, 3H), 4.35 (s, 2H), 2.18 (s, 3H), 1.26 (s, 9H); MS (APCI−) m/z 380.2 (M−H).

Example 102f 5-(3-Bromo-2-methylphenyl)-2-tert-butyl-4H-thieno[3,2-c]pyrrol-6(5H)-one 102f

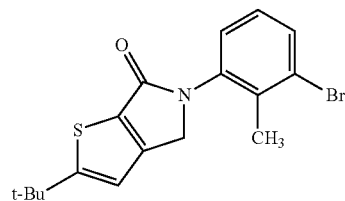 [SMILES: Cc1c(Br)cccc1N1Cc2cc(C(C)(C)C)sc2C1=O]

A 250-mL single-necked round-bottomed flask equipped with a magnetic stirrer was purged with nitrogen and charged with 102e (1.12 g, 2.93 mmol) and anhydrous methylene chloride (50 mL). Thionyl chloride (1.25 g, 10.5 mmol) was added and the reaction was stirred at ambient temperature. After 16 h the reaction was concentrated under reduced pressure. Purification of the resulting residue by column chromatography afforded a 65% yield (757 mg) of 102f as a white solid: mp 185-186° C.; $^1$H NMR (300 MHz, CDCl$_3$) δ 7.56 (dd, 1H, J=6.6, 1.2 Hz), 7.20 (dd, 1H, J=6.3, 1.5 Hz), 7.11 (t, 1H, 7.8 Hz), 6.87 (s, 1H), 4.56 (s, 2H), 2.33 (s, 3H), 1.45 (s, 9H); MS (ESI+) m/z 364.2 (M+H).

Example 102g 2-tert-Butyl-5-(2-methyl-3-(4,4,5,5-tetramethyl-1,3,2-dioxaborolan-2-yl)phenyl)-4H-thieno[3,2-c]pyrrol-6(5H)-one 102g

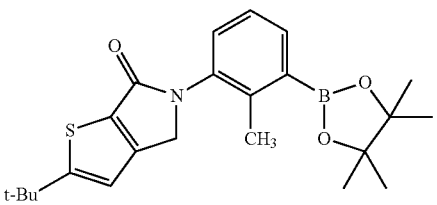 [SMILES: Cc1c(B2OC(C)(C)C(C)(C)O2)cccc1N1Cc2cc(C(C)(C)C)sc2C1=O]

A 100-mL single-necked round-bottomed flask equipped with a magnetic stirrer was charged with 102f (757 mg, 2.08 mmol), bis(pinacolato)diboron (554 mg, 2.18 mmol, bis(dibenzylideneacetone)palladium (191 mg, 0.21 mmol), dicyclohexyl(2',4',6'-triisopropylbiphenyl-2-yl)phosphine (X-Phos) (198 mg, 0.42 mmol), potassium acetate (306 mg, 3.12 mmol) and anhydrous dioxane (10 mL). The flask was then sealed and the mixture degassed by evacuating the flask and re-filling with nitrogen three times. The reaction was then placed in an 80° C. oil bath. After 16 h the reaction was then cooled to room temperature and concentrated under reduced pressure to residue. The resulting residue was then diluted with ethyl acetate (300 mL) and washed with water (120 mL). The organic layer was then separated and dried over sodium sulfate. The drying agent was removed by vacuum filtration; the filtrate was concentrated under reduced pressure, and the resulting residue was purified by column chromatography to afford 102g in 63% yield (541 mg) as a yellow foam: mp 102-104° C.; $^1$H NMR (300 MHz, CDCl$_3$) δ 7.79 (dd, 1H, J=5.4, 1.8 Hz), 7.29 (m, 1H), 7.23 (m, 1H), 6.86 (s, 1H), 4.53 (s, 2H), 2.45 (s, 3H), 1.41 (s, 9H), 1.27 (s, 12H); MS (APCI+) m/z 411.2 (M).

Example 102h

1-Methyl-3-(4-nitrophenyl)-5,6-dihydropyrazin-2(1H)-one 102h

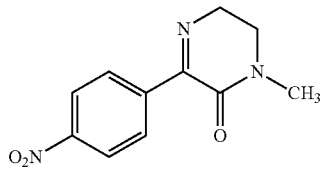 [SMILES: CN1CCN=C(c2ccc([N+](=O)[O-])cc2)C1=O]

A 250-mL single-neck round-bottomed flask equipped with a magnetic stirrer was purged with nitrogen, charged with ethyl 4-nitrophenylpyruvate (5.00 g, 22.4 mmol) and anhydrous methanol (112 mL). The resulting solution was cooled to 0° C. with an ice bath, and N-methylethylenediamine (1.66 g, 22.4 mmol) was added dropwise. After addition was complete, the bath was removed and the reaction was stirred at room temperature for 18 h. After this time the reaction was concentrated under reduced pressure. The residue was purified by column chromatography to afford 1-methyl-3-(4-nitrophenyl)-5,6-dihydropyrazin-2(1H)-one (102h) in 20% yield (1.02 g) as a yellow solid: mp 191-192° C.; $^1$H NMR (300 MHz, DMSO-$d_6$) δ 8.26 (d, 2H, J=6.9 Hz), 8.05 (d, 2H, J=7.2 Hz), 3.94 (t, 2H, J=6.3 Hz), 3.55 (t, 2H, J=6.3 Hz), 3.02 (s, 3H); MS (ESI+) m/z 234.1 (M+H).

Example 102i tert-Butyl 4-Methyl-2-(4-nitrophenyl)-3-oxopiperazine-1-carboxylate 102i

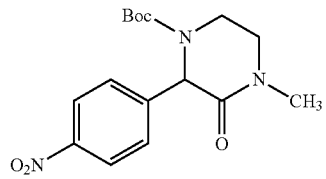 [SMILES: CN1CCN(C(=O)OC(C)(C)C)C(c2ccc([N+](=O)[O-])cc2)C1=O]

A 25-mL single-neck round-bottomed flask equipped with a magnetic stirrer was purged with nitrogen, charged with 1-methyl-3-(4-nitrophenyl)-5,6-dihydropyrazin-2(1H)-one 102h (233 mg, 1.00 mmol) and methanol (7 mL). A suspension of sodium cyanoborohydride (80 mg, 1.30 mmol) and anhydrous zinc chloride (204 mg, 1.50 mmol) in anhydrous methanol (7 mL) was added, and the reaction was stirred at room temperature for 1 h. After this time, di-tert-butyl dicarbonate (436 mg, 2.00 mmol) was added and the reaction was stirred at room temperature for 18 h. After this time the reaction was partitioned between 10% aqueous potassium carbonate (25 mL) and ethyl acetate (75 mL). The aqueous solution was separated and extracted with ethyl acetate (2×25 mL). The organic layers were combined, washed with water (20 mL) followed by brine (50 mL) and dried over magnesium sulfate. The drying agent was removed by filtration and the filtrate concentrated under reduced pressure to afford tert-butyl 4-methyl-2-(4-nitrophenyl)-3-oxopiperazine-1-carboxylate 102i in 96% yield (320 mg) as an amber oil: $^1$H NMR (300 MHz, DMSO-$d_6$) δ 8.24 (d, 2H, J=9.0 Hz), 7.63 (d, 2H, J=8.7 Hz), 5.48 (s, 1H), 3.93 (m, 1H), 3.51 (m, 1H), 3.47 (m, 2H), 2.91 (s, 1H), 1.35 (s, 9H); MS (ESI+) m/z 236.1 (M+H-Boc).

Example 102j tert-Butyl 2-(4-Aminophenyl)-4-methyl-3-oxopiperazine-1-carboxylate 102j

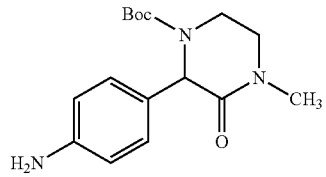

A 250-mL Parr hydrogenation bottle was purged with nitrogen and charged with 10% palladium on carbon (50% wet, 10 mg dry weight) followed by a solution of tert-butyl 4-methyl-2-(4-nitrophenyl)-3-oxopiperazine-1-carboxylate (102i) (1.00 g, 2.99 mmol) in ethanol (40 mL). The bottle was evacuated, then charged with hydrogen gas to a pressure of 50 psi and shaken at 50 psi for 18 h at room temperature on a Parr hydrogenation apparatus. After this time the hydrogen was evacuated and nitrogen charged into the bottle. The resulting suspension was filtered through a pad of Celite 521. The filter cake was washed with ethanol (2×20 mL), and the filtrate was evaporated to dryness under reduced pressure to afford a 99% yield (904 mg) of tert-butyl 2-(4-aminophenyl)-4-methyl-3-oxopiperazine-1-carboxylate 102j as a yellow syrup: $^1$H NMR (300 MHz, DMSO-$d_6$) δ 6.93 (d, 2H, J=8.4 Hz), 6.51 (d, 2H, J=8.4 Hz), 5.27 (bs, 1H), 5.09 (s, 1H), 3.83 (d, 1H, J=10.8 Hz), 3.44 (m, 1H), 3.24 (m, 2H), 2.84 (s, 3H), 1.40 (s, 9H); MS (ESI+) m/z 306.2 (M+H).

Example 102k tert-Butyl 2-(4-(6-Bromo-4-methyl-3-oxo-3,4-dihydropyrazin-2-ylamino)phenyl)-4-methyl-3-oxopiperazine-1-carboxylate 102k

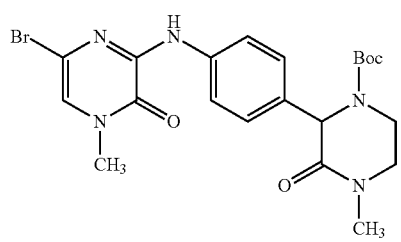

A 50-mL single-neck round-bottomed flask equipped with a magnetic stirrer, nitrogen inlet and reflux condenser was charged with tert-butyl 2-(4-aminophenyl)-4-methyl-3-oxopiperazine-1-carboxylate 102j (880 mg, 2.88 mmol), 3,5-dibromo-1-methylpyrazin-2(1H)-one (770 mg, 2.88 mmol), cesium carbonate (2.06 g, 6.34 mmol) and 1,4-dioxane (20 mL). After bubbling nitrogen through the resulting solution for 30 minutes, Xantphos (166 mg, 0.288 mmol) and tris(dibenzylidene acetone)dipalladium(0) (47 mg, 0.144 mmol) were added and the reaction mixture was heated at reflux for 18 h. After this time the reaction was cooled to room temperature, partitioned between ethyl acetate (50 mL) and water (50 mL), and filtered, and the filter cake was washed with ethyl acetate (2×25 mL). The organic layer was separated, washed with brine (50 mL) and dried over magnesium sulfate. The drying agent was removed by filtration and the filtrate concentrated under reduced pressure. The residue was purified by column chromatography to afford 102k (850 mg, 60%) as an orange foam: $^1$H NMR (300 MHz, CDCl$_3$) δ 7.28 (s, 1H), 7.16 (d, 2H, J=8.4 Hz), 6.65 (d, 2H, J=8.4 Hz), 5.65

(s, 1H), 4.02 (m, 1H), 3.51 (m, 1H), 3.30 (m, 3H), 3.05 (s, 3H), 1.47 (s, 9H), MS (ESI+) m/z 492.1 (M+H).

Example 102l tert-Butyl 2-(4-(6-(3-(2-tert-Butyl-6-oxo-4H-thieno[2,3-c]pyrrol-5(6H)-yl)-2-methylphenyl)-4-methyl-3-oxo-3,4-dihydropyrazin-2-ylamino)phenyl)-4-methyl-3-oxopiperazine-1-carboxylate 102l

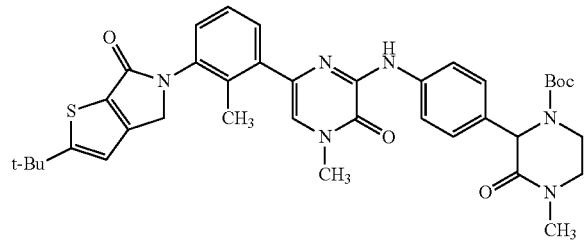 [SMILES: Cc1c(-c2cn(C)c(=O)c(Nc3ccc(C4C(=O)N(C)CCN4C(=O)OC(C)(C)C)cc3)n2)cccc1N1Cc2cc(C(C)(C)C)sc2C1=O]

A 25-mL three-neck round-bottomed flask equipped with a reflux condenser, magnetic stirrer and nitrogen inlet was charged with of 102k (200 mg, 0.486 mmol), 102g (217 mg, 0.442 mmol), sodium carbonate (115 mg, 1.08 mmol), water (1.5 mL), 1,4-dioxane (5 mL), and DMF (2 mL). After bubbling nitrogen through the resulting suspension for 30 min, tetrakis(triphenylphosphine)palladium(0) (83 mg, 0.07 mmol) was added and the reaction mixture was heated at reflux for 16 h. After this time, the mixture was cooled to room temperature and diluted with ethyl acetate (40 mL) and water (5 mL). The organic layer was separated, dried over sodium sulfate, and concentrated under reduced pressure. The residue was purified by column chromatography on silica gave an 88% yield (272 mg) of 102l as a brown foam: mp 120-123° C.; $^1$H NMR (300 MHz, CDCl$_3$) δ 8.33 (s, 1H), 7.79 (d, 2H, J=6.9 Hz), 7.71-7.28 (m, 5H), 6.92 (s, 1H), 6.75 (s, 1H), 5.30 (s, 3H), 4.63 (s, 2H), 4.61 9s, 1H), 3.62 (s, 3H), 3.50 (m, 2H), 3.42-3.22 (m, 2H), 3.04 (m, 4H), 1.46 (s, 18H); MS (APCI+) m/z 697.5 (M+H).

Example 102

2-tert-Butyl-5-(2-methyl-3-(4-methyl-6-(4-(4-methyl-3-oxopiperazin-2-yl)phenylamino)-5-oxo-4,5-dihydropyrazin-2-yl)phenyl)-4H-thieno[2,3-c]pyrrol-6(5H)-one 102

A 10-mL single-neck round bottomed flask equipped with a magnetic stirrer was purged with nitrogen and charged with of 102l (270 mg, 0.39 mmol) methanol (6 mL) and 4 M HCl in dioxane (6 mL) and the mixture stirred for 2 h. After this time, ethyl acetate (60 mL) and water (60 mL) were added. The pH was adjusted to 6.5 with aqueous 10% potassium carbonate. The aqueous layer was separated and extracted with ethyl acetate (2×75 mL). The combined organic layers were washed with brine (60 mL) and dried over sodium sulfate. The drying agent was removed by filtration. The filtrate was concentrated under reduced pressure to a residue which was purified by column chromatography to a 36% yield (83 mg) of 102 as an off-white solid: mp 164-166° C.; $^1$H NMR (500 MHz, DMSO-d$_6$) δ 9.17 (s, 1H), 7.90 (d, 2H, J=5.1 Hz), 7.41 (t, 2H, J=8.0 Hz), 7.33 (t, 1H, J=7.5 Hz), 7.22 (d, 3H, J=9.5 Hz), 7.14 (s, 1H), 4.77 (s, 2H), 4.29 (s, 1H), 3.56 (s, 3H), 3.38 (m, 1H), 3.24 (m, 1H), 2.97-2.86 (m, 3H), 2.84 (s, 3H), 2.23 (s, 3H), 1.42 (9H); MS (ESI+) m/z 597.2 (M+H).

Example 103

Example 103a 4-tert-Butyl-N,N-diethyl-2-formylbenzamide 103a

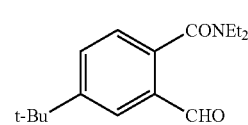

A 1-L, three-neck, round-bottomed flask equipped with a magnetic stirrer and reflux condenser was purged with nitrogen and charged with TMEDA (11.6 g, 100 mmol) and THF (160 mL). The reaction was cooled to −70° C. and s-BuLi (1.4 M in hexanes, 69 mL, 96.7 mmol) was added dropwise and the reaction stirred at −70° C. for 25 min. A separate 100-mL, three-neck, round-bottomed flask equipped with a magnetic stirrer under nitrogen was charged with 4-tert-butyl-N,N-diethyllbenzamide (18.6 g, 79.8 mmol) and THF (50 mL). The solution was cooled to −70° C. and cannulated into the cold (−75° C.) solution of TMEDA/s-BuLi over 8 min maintaining the temperature between −75 to −70° C. After the addition was complete, the reaction was stirred at −70° C. for 20 min. After this time, DMF (17.9 g, 245 mmol) was added dropwise over 2 min maintaining the temperature under −70° C. After stirring at −70° C. for 70 min the cooling bath was removed and the reaction allowed to warm to −30° C. over 20 min. At this time 4 M hydrochloric acid (80 mL, 320 mmol) was added (solution pH 6.5). After stirring for 30 min the organic layer was separated and concentrated under reduced pressure to dryness. The residue was then partitioned between hexanes (200 mL) and water (200 mL). The organic layer was separated, dried over sodium sulfate and filtered. The filtrate was concentrated under reduced pressure and the resulting residue was purified by column chromatography to afford an 88% yield (18.3 g) of 103a as a yellow oil: $^1$H NMR (300 MHz, CDCl$_3$) δ 10.0 (s, 1H), 7.93 (s, 1H), 7.71 (d, 1H, J=6.3 Hz), 7.28 (d, 1H, J=6.4 Hz), 3.62 (m, 2H), 3.18 (m, 2H), 1.36 (s, 9H), 1.31 (t, 3H, J=7.2 Hz), 1.07 (t, 3H, J=7.1 Hz).

Example 103b

Methyl 5-tert-Butyl-2-(diethylcarbamoyl)benzylcarbamate 103b

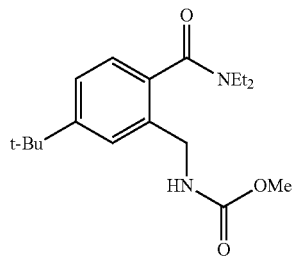

A 25-mL microwave vial equipped with a magnetic stirrer was charged with 103a (1.00 g, 3.83 mmol), methyl carbamate (575 mg, 7.66 mmol), trifluoroacetic acid (871 mg, 7.66 mmol), triethylsilane (888 mg, 7.66 mmol) and acetonitrile (10 mL). The vial was loaded in a Biotage microwave and heated at 130° C. for 1.5 h. After this time, the solution was concentrated in vacuo. The resulting residue was partitioned between methylene chloride (100 mL) and a saturated aqueous sodium bicarbonate (30 mL). The aqueous layer was extracted with methylene chloride (3×20 mL). The combined organic layers were washed with brine (30 mL), dried over sodium sulfate and concentrated under reduced pressure. The residue was purified by column chromatography (silica, 0% to 60% ethyl acetate/hexanes) to afford a 71% yield (858 mg) of 103b as a colorless oil; $^1$H NMR (300 MHz, CDCl$_3$) δ 7.42 (s, 1H), 7.29 (m, 1H), 7.12 (d, 1H, J=7.7 Hz), 5.60 (br s, 1H), 4.27 (br s, 2H), 3.65 (s, 3H), 3.57 (q, 2H, J=6.8 Hz), 3.20 (q, 2H, J=6.7 Hz), 1.31 (s, 9H), 1.26 (t, 3H, J=6.7 Hz), 1.09 (t, 3H, J=6.8 Hz); MS (ESI+) m/z 321.2 (M+H).

Example 103c 5-tert-Butylisoindolin-1-one 103c

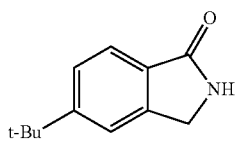

A 25-mL microwave vial equipped with a magnetic stirrer was charged with 103b (858 mg, 2.68 mmol), tetrahydrofuran (5 mL), methanol (5 mL) and 2 M aqueous lithium hydroxide (5 mL). The vial was loaded in a Biotage microwave and heated at 110° C. for 2.5 h. After this time, the solution was neutralized with 2 M hydrochloric acid to pH 7 and concentrated in vacuo. The resulting residue was partitioned between ethyl acetate (150 mL) and water (30 mL). The aqueous layer was extracted with ethyl acetate (3×20 mL). The combined organic layers were washed with brine (30 mL), dried over sodium sulfate and concentrated under reduced pressure. The residue was purified by column chromatography (silica, 50% ethyl acetate to 100% ethyl acetate/hexanes) to afford a 56% yield (285 mg) of 103c as an off-white solid: mp=132-134° C.; $^1$H NMR (300 MHz, CDCl$_3$) δ 7.80 (d, 1H, J=7.8 Hz), 7.52 (m, 2H), 6.71 (br s, 1H), 4.44 (s, 2H), 1.37 (s, 9H), MS (ESI+) m/z 190.1 (M+H).

Example 103d 2,6-Dibromobenzyl Acetate (2d 1,3-Dibromo-2-(bromomethyl)benzene 103d

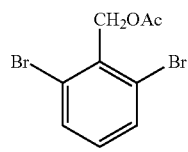

A 250-mL single-neck round-bottomed flask equipped with a magnetic stirrer, reflux condenser and nitrogen inlet was purged with nitrogen and charged with 2,6-dibromotoluene (2.50 g, 10.0 mmol), N-bromosuccinimide (1.78 g, 10.0 mmol) and carbon tetrachloride (40 mL). The solution was heated to 80° C. (oil bath temperature), and 2,2'-azobisisobutyronitrile (164 mg, 1.00 mmol) was added. The resulting mixture was refluxed for 14 h. After that time, the mixture was cooled to room temperature and filtered. The filter cake was washed with carbon tetrachloride (2×20 mL). The filtrate was diluted with ethyl acetate (200 mL) and washed with water (40 mL), saturated aqueous sodium bicarbonate (40 mL) and brine (40 mL). The organic layer was dried over sodium sulfate and concentrated under reduced pressure to afford a quantative yield (3.28 g) of 1,3-dibromo-2-(bromomethyl)benzene as a yellow solid: mp 77-78° C.; $^1$H NMR (300 MHz, CDCl$_3$) δ 7.55 (d, 2H, J=8.1 Hz), 7.07 (t, 1H, J=8.1 Hz), 4.83 (s, 2H). A 250-mL single-neck round-bottomed flask equipped with a magnetic stirrer and nitrogen inlet was purged with nitrogen and charged with this residue (3.28 g, 10.0 mmol), potassium acetate (3.93 g, 40.0 mmol) and DMF (100 mL). The solution was stirred at room temperature for 14 h. After that time, the reaction mixture was diluted with water (900 mL) and extracted with ethyl acetate (3×200 mL). The combined organic layers were washed with brine (100 mL), dried over sodium sulfate and concentrated under reduced pressure. The residue was purified by column chromatography to afford an 88% yield (2.70 g) of 103d as an off-white solid: mp 62-65° C.; $^1$H NMR (300 MHz, CDCl$_3$) δ 7.57 (d, 2H, J=8.0 Hz), 7.07 (t, 1H, J=7.9 Hz), 5.42 (s, 2H), 2.11 (s, 3H); MS (ESI+) m/z 306.9 (M+H).

Example 103e

2-Bromo-6-(5-tert-butyl-1-oxoisoindolin-2-yl)benzyl Acetate 103e

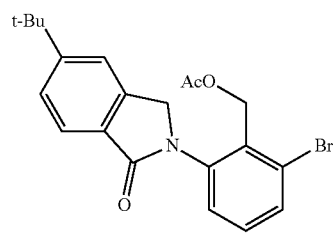

A 100-mL three-neck round-bottomed flask equipped with a reflux condenser, magnetic stirrer was purged with nitrogen and charged with 103c (570 mg, 3.02 mmol), 103d (1.85 g, 6.04 mmol), cesium carbonate (1.96 g, 6.04 mmol), N,N'-dimethyl-ethylenediamine (266 mg, 3.02 mmol), and 1,4-dioxane (27 mL). After bubbling nitrogen through the resulting suspension for 30 min, copper iodide (287 mg, 1.51 mmol) was added, and the reaction mixture was heated at 105° C. (oil bath temperature) for 14 h. After this time, the mixture was cooled to room temperature and filtered. The filtrate was diluted with ethyl acetate (150 mL) and water (30 mL). The organic layer was separated, and the aqueous layer was extracted with ethyl acetate (3×50 mL). The combined organic layers were dried over sodium sulfate and concentrated under reduced pressure. The residue was purified by column chromatography (silica, 0% to 50% ethyl acetate/hexanes) to afford a 41% yield (555 mg) of 103e as an off-white solid: mp 176-178° C.; ¹H NMR (300 MHz, CDCl₃) δ 7.86 (d, 1H, J=8.1 Hz), 7.66 (dd, 1H, J=7.9, 1.5 Hz), 7.59 (dd, 1H, J=8.1, 1.5 Hz), 7.52 (s, 1H), 7.29 (m, 2H), 5.20 (s, 2H), 4.77 (s, 2H), 1.99 (s, 3H), 1.40 (s, 9H); MS (ESI+) m/z 416.1 (M+H).

Example 103f 2-(5-tert-Butyl-1-oxoisoindolin-2-yl)-6-(4,4,5,5-tetramethyl-1,3,2-dioxaborolan-2-yl)benzyl Acetate 103f

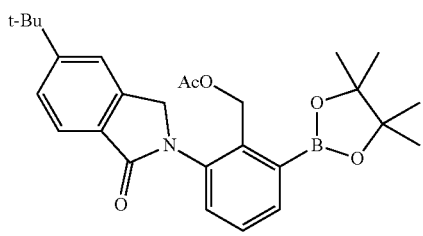

A 100-mL three-neck round-bottomed flask equipped with a reflux condenser, magnetic stirrer and nitrogen inlet was charged with 103e (555 mg, 1.34 mmol), 4,4,4',4',5,5,5',5'-octamethyl-2,2'-bi(1,3,2-dioxaborolane) (1.36 g, 5.35 mmol), potassium acetate (527 mg, 5.35 mmol) and 1,4-dioxane (20 mL). After bubbling nitrogen through the resulting suspension for 30 min, XPhos (128 mg, 0.268 mmol) and tris(dibenzylideneacetone)dipalladium(0) (123 mg, 0.134 mmol) were added, and the reaction mixture was heated at 105° C. (oil bath temperature) for 14 h. After this time, the mixture was cooled to room temperature and filtered. The filter cake was washed with ethyl acetate (3×20 mL). The filtrate was diluted with ethyl acetate (150 mL) and water (40 mL). The organic layer was separated, and the aqueous layer was extracted with ethyl acetate (3×50 mL). The combined organic layers were dried over sodium sulfate and concentrated under reduced pressure to afford a 74% yield (444 mg) of crude 103f as yellow oil. The material was used in the next step without further purification.

Example 103g (3-Nitro-1H-pyrazol-5-yl)methanol 103g

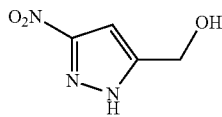

A 3-L three-neck round-bottomed flask equipped with a mechanical stirrer, addition funnel and nitrogen inlet was purged with nitrogen and charged with 3-nitropyrazole-5-carboxylic acid (28.0 g, 178 mmol) and THF (420 mL) and cooled to −5° C. using an ice/acetone bath. Borane-THF complex solution (1.0 M, 535 mL, 535 mmol) was added at a rate that maintained the internal reaction temperature below 5° C. After the addition was complete the cooling bath was removed and the reaction was stirred at room temperature for 18 h. After this time the reaction was cooled to −5° C. using an ice/acetone bath, water (70 mL) and 4N hydrochloric acid (70 mL) was added and the reaction was stirred at reflux for 1 h in order to destroy the borane complex with pyrazole. The reaction was cooled to room temperature and concentrated under reduced pressure to a volume of approximately 30 mL. Ethyl acetate (175 mL) was added and the mixture stirred for 15 min. The aqueous layer was separated and extracted with ethyl acetate (4×200 mL). The combined organic layers were washed with saturated aqueous sodium bicarbonate (2×50 mL), brine (50 mL) and dried over sodium sulfate, the drying agent was removed by filtration, and the filtrate concentrated under reduced pressure to afford (3-nitro-1H-pyrazol-5-yl)methanol 103g in a 94% yield (24.0 g) as a light yellow solid: 1H NMR (300 MHz, DMSO-d₆) δ 13.90 (br s, 1H), 6.87 (s, 1H), 5.58 (t, 1H, J=5.4 Hz), 4.53(d, 2H, J=5.1 Hz); MS (ESI+) m/z 144.0 (M+H).

Example 103h (1-(2-Bromoethyl)-3-nitro-1H-pyrazol-5-yl)methanol 103h

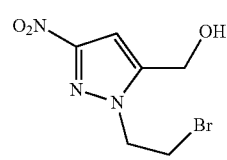

A 1-L three-necked round-bottomed flask equipped with a mechanical stirrer and thermoregulator was purged with nitrogen and charged with (3-nitro-1H-pyrazol-5-yl)methanol 103g (25.0 g, 175 mmol), DMF (250 mL), and cesium carbonate (70.0 g, 215 mmol) was heated at 104° C. for 5 min. The reaction mixture was then cooled to 0° C. using an ice/acetone bath and dibromoethane (329 g, 1.75 mol) was added portionwise (no exotherm). The reaction was stirred at 0° C. for 1 then at room temperature for 4 h. After this time a solution of KH₂PO4 (40 g) in water (400 mL) was added slowly. The reaction mixture stirred at room temperature for 30 min. Ethyl acetate (450 mL) was added and the aqueous layer was separated and extracted with ethyl acetate (2×100 mL). The combined organic layers were washed with water (200 mL), brine (200 mL), dried over sodium sulfate, and the drying agent was removed by filtration. The filtrate was concentrated under reduced pressure to afford an 86% yield (37.5 g) of crude (1-(2-bromoethyl)-3-nitro-1H-pyrazol-5-yl)methanol (103h) as an orange oil: 1H NMR (300 MHz, CDCl$_3$) δ 6.85 (s, 1H), 4.82 (d, 2H, J=5.4 Hz), 4.66 (t, 2H, J=6.3 Hz), 3.83 (t, 2H, J=6.3 Hz); MS (ESI+) m/z 249.9 (M+H).

Example 103i 1-(2-Bromoethyl)-5-(bromomethyl)-3-nitro-1H-pyrazole 103i

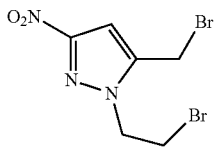

A 500-mL three-necked round-bottomed flask equipped with a magnetic stirrer, nitrogen inlet and reflux condenser was purged with nitrogen and charged with (1-(2-bromoethyl)-3-nitro-1H-pyrazol-5-yl)methanol 103h (37.0 g, 148 mmol) and chloroform (160 mL). The reaction was cooled to −5° C. using an ice/acetone bath and phosphorous tribromide (40.0 g, 148 mmol) was added portionwise. The cooling bath was removed and the reaction stirred at reflux for 2 h. After this time, the reaction was cooled to −5° C. and saturated aqueous sodium bicarbonate (250 mL) was added until a pH of 8.5 was reached. The mixture was extracted with ethyl acetate (3×150 mL) and the combined organic layers were washed with saturated aqueous sodium carbonate (2×50 mL), brine (75 mL), dried over sodium sulfate and the drying agent was removed by filtration. The filtrate was concentrated under reduced pressure to afford a yellow residue that was dissolved with gentle heating in methylene chloride (60 mL). Hexane (approximately 20 mL) was added and the solution became cloudy. The mixture was heated until a solid precipitate formed, methylene chloride (9 mL) was added and the solution became clear. The solution was left to cool to room temperature and after 4 h the resulting crystals were collected by vacuum filtration. The filter cake was washed with a ice cold 1:2 mixture of methylene chloride:hexanes (2×20 mL) to afford 1-(2-bromoethyl)-5-(bromomethyl)-3-nitro-1H-pyrazole 103i (19.7 g). The combined filtrates were evaporated and the procedure was performed again to afford an additional 9.70 g of 1-(2-bromoethyl)-5-(bromomethyl)-3-nitro-1H-pyrazole 103i. The solids were combined and dried under high vacuum for 18 h to afford a 57% yield (26.0 g) of 1-(2-bromoethyl)-5-(bromomethyl)-3-nitro-1H-pyrazole 103i as white crystals: mp 95-97° C.; $^1$H NMR (300 MHz, CDCl$_3$) δ 6.93 (s, 1H), 4.63 (t, 2H, J=6.0 Hz), 4.54 (s, 2H), 3.86 (t, 2H, J=6.0 Hz).

Example 103j

5-Methyl-2-nitro-4,5,6,7-tetrahydropyrazolo[1,5-a]pyrazine 103j

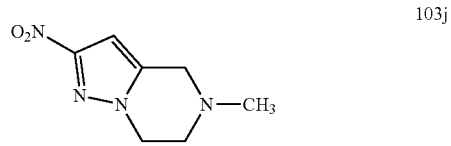

A 1-L single-neck round-bottomed flask equipped with a magnetic stirrer and nitrogen inlet was charged with THF (350 mL), 1-(2-bromoethyl)-5-(bromomethyl)-3-nitro-1H-pyrazole 103i (10.0 g, 32.2 mmol), 2M methylamine solution in THF (113 mL, 225 mmol) and stirred at room temperature for 72 h. After this time the reaction was concentrated to dryness under reduced pressure, and the resulting solid was stirred with a mixture of ethyl acetate (75 mL) and 10% aqueous potassium carbonate (75 mL). The aqueous layer was separated and extracted with ethyl acetate (2×75 mL). The combined organic extracts were washed with 10% aqueous potassium carbonate (75 mL), followed by brine (50 mL) and dried over sodium sulfate. The drying agent was removed by filtration, and the filtrate concentrated under reduced pressure to afford 5-methyl-2-nitro-4,5,6,7-tetrahydropyrazolo[1,5-a]pyrazine 103j in a 97% yield (5.70 g) as a yellow solid: 1H NMR (300 MHz, CDCl$_3$) d 6.62 (s, 1H), 4.28 (t, 2H, J=5.4 Hz), 3.67 (s, 2H), 2.95 (t, 2H, J=5.4 Hz), 2.52 (s, 3H); MS (ESI+) m/z 183.0 (M+H).

Example 103k

5-Methyl-4,5,6,7-tetrahydropyrazolo[1,5-a]pyrazin-2-amine 103k

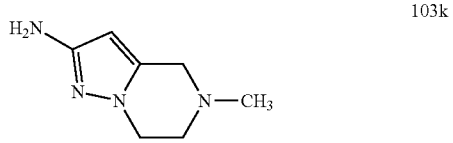

A 500-mL Parr reactor bottle was purged with nitrogen and charged with 10% palladium on carbon (50% wet, 800 mg dry weight) and a solution of 5-methyl-2-nitro-4,5,6,7-tetrahydropyrazolo[1,5-a]pyrazine 103j (4.00 g, 2.20 mmol) in ethanol (160 mL). The bottle was attached to Parr hydrogenator, evacuated, charged with hydrogen gas to a pressure of 45 psi and shaken for 2 h. After this time, the hydrogen was evacuated, and nitrogen was charged into the bottle. Celite 521 (1.0 g) was added, and the mixture was filtered through a pad of Celite 521. The filter cake was washed with ethanol (2×75 mL), and the combined filtrates were concentrated to dryness under reduced pressure to afford a 99% yield of 5-methyl-4,5,6,7-tetrahydropyrazolo[1,5-a]pyrazin-2-amine 103k (3.31 g) as an orange solid: $^1$H NMR (300 MHz, CDCl$_3$) δ 5.34 (s, 1H), 3.98 (t, 2H, J=5.4 Hz), 3.52 (s, 3H), 2.84 (t, 2H, J=5.7 Hz), 2.45 (s, 3H); MS (ESI+) m/z 153.1 (M+H).

Example 1031

5-Bromo-1-methyl-3-(5-methyl-4,5,6,7-tetrahydro-pyrazolo[1,5-c]pyrazin-2-ylamino)pyridin-2(1H)-one 1031

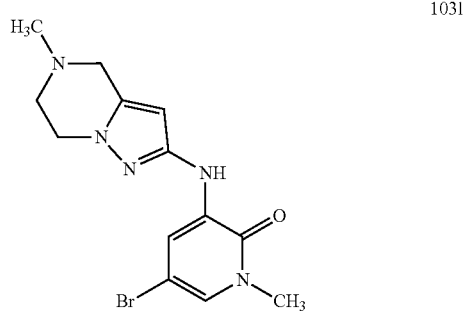 [SMILES: CN1CCn2nc(Nc3cc(Br)cn(C)c3=O)cc2C1]

A 15-mL pressure tube equipped with a magnetic stirrer and screw cap with a septum was charged with 103k (100 mg, 0.657 mmol), 3,5-dibromo-1-methylpyridin-2(1H)-one (351 mg, 1.30 mmol), cesium carbonate (644 mg, 1.98 mmol), and 1,4-dioxane (5 mL). After bubbling nitrogen through the resulting suspension for 30 min, Xantphos (33 mg, 0.057 mmol) and tris(dibenzylideneacetone)dipalladium(0) (31 mg, 0.034 mmol) were added; the tube was sealed, and the reaction mixture was heated for 16 h in a 130° C. bath. After this time, the mixture was cooled to room temperature and concentrated under reduced pressure. The residue was purified by column chromatography on silica to afford a 91% yield (204 mg) of 1031 as an off-white solid: mp 174-176° C.; $^1$H NMR (300 MHz, DMSO-$d_6$) δ 8.42 (s, 1H), 8.00 (d, 1H, J=2.6 Hz), 7.37 (d, 1H, J=2.6 Hz), 5.86 (s, 1H), 3.99 (t, 2H, J=5.0 Hz), 3.49 (m, 5H), 2.81 (t, 2H, J=5.4 Hz), 2.36 (s, 3H); MS (ESI+) m/z 338.1 (M+H).

Example 103

5-tert-Butyl-2-(2-(hydroxymethyl)-3-(1-methyl-5-(5-methyl-4,5,6,7-tetrahydropyrazolo[1,5-a]pyrazin-2-ylamino)-6-oxo-1,6-dihydropyridin-3-yl)phenyl)isoindolin-1-one 103

A 25-mL three-neck round-bottomed flask equipped with a reflux condenser, magnetic stirrer and nitrogen inlet was charged with 103f (444 mg, 0.99 mmol), 1031 (258 mg, 0.76 mmol), sodium carbonate (242 mg, 2.29 mmol), DMF (5 mL), water (2.5 mL) and 1,4-dioxane (8 mL). After bubbling nitrogen through the resulting suspension for 30 min, tetrakis (triphenylphosphine)palladium(0) (89 mg, 0.076 mmol) was added, and the reaction mixture was heated at reflux for 14 h. After this time, the mixture was cooled to room temperature and diluted with ethyl acetate (100 mL) and water (30 mL). The organic layer was separated, and the aqueous layer was extracted with ethyl acetate (3×25 mL). The combined organic layers were dried over sodium sulfate and concentrated. The residue was purified by column chromatography (silica, 0% to 10% methanol/methylene chloride) to afford a 50% yield (210 mg) of 103 as an off-white solid: 146-147° C.; $^1$H NMR (500 MHz, DMSO-$d_6$) δ 8.11 (s, 1H), 7.98 (d, 1H, J=2.3 Hz), 7.72 (m, 2H), 7.61 (m, 1H), 7.48 (m, 1H), 7.41 (m, 1H), 7.35 (m, 1H), 7.23 (d, 1H, J=2.2 Hz), 5.87 (s, 1H), 4.93 (s, 2H), 4.88 (t, 1H, J=5.1 Hz), 4.34 (d, 2H, J=5.0 Hz), 3.91 (t, 2H, J=4.9 Hz), 3.57 (s, 3H), 3.48 (s, 2H), 2.77 (t, 2H, J=5.1 Hz), 2.34 (s, 3H), 1.37 (s, 9H); MS (ESI+) m/z 553.2 (M+H).

Example 104

Example 104a 3-(4-Nitrophenyl)-5,6-dihydropyrazin-2(1H)-one 104a

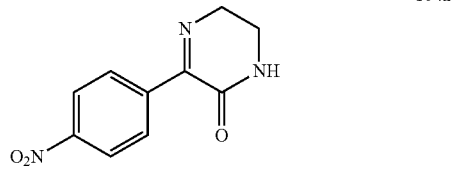

A 50-mL single-neck round-bottomed flask equipped with a magnetic stirrer was purged with nitrogen, charged with ethyl 4-nitrophenylpyruvate (223 mg, 1.00 mmol), 3 pieces of molecular sieves (4-8 mesh, 3A) and anhydrous methanol (10 mL). The resulting solution was cooled to 0° C. with an ice bath and 1b (63 mg, 1.05 mmol) was added dropwise. After addition was complete the reaction was stirred at room temperature for 1 h. After this time the resulting suspension was filtered and the filter cake washed with cold methanol (2×5 mL). The filter cake was dried in an oven at 50° C. overnight under vacuum to afford 104a in 89% yield (196 mg) as a white solid: mp 191-192° C.; $^1$H NMR (500 MHz, DMSO-$d_6$) δ 8.63 (bs, 1H), 8.26 (d, 2H, J=8.0 Hz), 8.09 (d, 2H, J=8.0 Hz), 3.88 (t, 2H, J=6.5 Hz), 3.37 (m, 2H); MS (ESI+) m/z 220 (M+H).

Example 104b

4-Methyl-3-(4-nitrophenyl)piperazine-2-one 104b

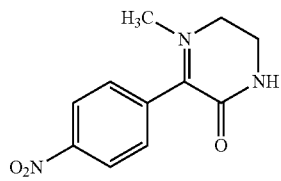

A 10-mL single-neck round-bottomed flask equipped with a magnetic stirrer was purged with nitrogen, charged with 104a (196 mg, 0.89 mmol), 37% solution of formaldehyde in water (35 mg, 1.16 mmol) and anhydrous methanol (3 mL). A solution of sodium cyanoborohydride (169 mg, 2.68 mmol) and anhydrous zinc chloride (183 mg, 1.34 mmol) in anhydrous methanol (3 mL) was added, and the reaction was stirred at room temperature for 1 h. After this time, 1N aqueous sodium hydroxide (2 mL) was added, and the methanol was evaporated under reduced pressure. The remaining aqueous solution was extracted with ethyl acetate (3×25 mL). The organic layers were combined, washed with water (20 mL)

and brine (20 mL) and dried over magnesium sulfate. The drying agent was removed by filtration and the filtrate concentrated under reduced pressure to afford 104b in 100% yield (210 mg) as a yellow solid: mp 185-186° C.; $^1$H NMR (300 MHz, DMSO-$d_6$) δ 8.18 (d, 2H, J=8.1 Hz), 8.05 (d, 1H, J=3.6 Hz), 7.63 (d, 2H, J=7.8 Hz), 3.82 (s, 1H), 3.45 (m, 1H), 3.17 (m, 1H), 2.95 (m, 1H), 2.56 (m, 1H), 2.06 (s, 3H); MS (ESI+) m/z 236 (M+H).

Example 104c 3-(4-Aminophenyl)-4-methylpiperazin-2-one 104c

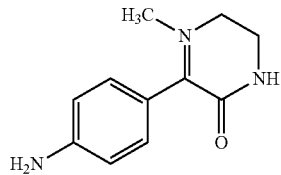

A 25-mL single-neck round-bottomed flask equipped with a reflux condenser and magnetic stirrer was purged with nitrogen and charged with 104b (210 mg, 0.89 mmol), ethanol (6 mL), iron powder (−325 mesh, 491 mg, 8.93 mmol) and 2N hydrochloric acid (0.70 mL, 1.40 mmol), and the mixture was heated at reflux for 30 min. After this time, the reaction was cooled to room temperature, and powdered potassium carbonate (3.03 g, 22.0 mmol) was added. The resulting suspension was filtered and the filter cake washed with ethanol (4×10 mL). The filtrate was concentrated under reduced pressure to afford 104c in 100% yield (185 mg) as a white solid: mp 153-154° C.; $^1$H NMR (300 MHz, DMSO-$d_6$) δ 7.74 (d, 1H, J=2.7 Hz), 6.90 (d, 2H, J=8.4 Hz), 6.47 (d, 2H, J=8.4 Hz), 4.95 (bs, 2H), 3.45 (m, 1H), 3.42 (s, 1H), 3.14 (m, 1H), 2.89 (m, 1H), 2.44 (m, 1H), 2.02 (s, 3H); MS (ESI+) m/z 206 (M+H).

Example 104d 2-(4-(6-Bromo-4-methyl-3-oxo-3,4-dihydropyrazin-2-ylamino)phenyl)-1-methyl-3-oxopiperazine 104d

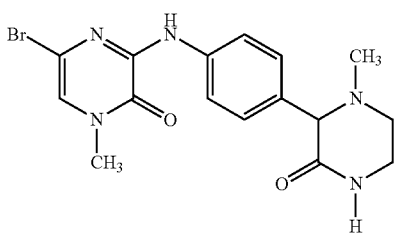

A 50-mL single-neck round-bottomed flask equipped with a magnetic stirrer, nitrogen inlet and reflux condenser was charged with 3-(4-aminophenyl)-4-methyl-piperazin-2-one 104c (590 mg, 2.88 mmol), 3,5-dibromo-1-methylpyrazin-2(1H)-one (770 mg, 2.88 mmol), cesium carbonate (2.06 g, 6.34 mmol) and 1,4-dioxane (20 mL). After bubbling nitrogen through the resulting solution for 30 minutes, Xantphos (166 mg, 0.288 mmol) and tris(dibenzylidene acetone)dipalladium(0) (47 mg, 0.144 mmol) were added and the reaction mixture was heated at reflux for 18 h. After this time the reaction was cooled to room temperature, partitioned between ethyl acetate (50 mL) and water (50 mL), and filtered, and the filter cake was washed with ethyl acetate (2×25 mL). The organic layer was separated, washed with brine (50 mL) and dried over magnesium sulfate. The drying agent was removed by filtration and the filtrate concentrated under reduced pressure. The residue was purified by column chromatography to afford 104d (850 mg, 60%) as an orange foam: MS (ESI+) m/z 492.1 (M+H).

Example 104

N-(2-Methyl-3-(4-methyl-6-(4-(1-methyl-3-oxopiperazin-2-yl)phenylamino)-5-oxo-4,5-dihydropyrazin-2-yl)phenyl)-4,5,6,7-tetrahydro-benzo[b]thiophene-2-carboxamide 104

Example 104

2-tert-Butyl-5-(2-methyl-3-(4-methyl-6-(4-(1-methyl-3-oxopiperazin-2-yl)phenylamino)-5-oxo-4,5-dihydropyrazin-2-yl)phenyl)-4H-thieno[2,3-c]pyrrol-6(5H)-one 104

A 5-mL reaction tube equipped with a magnetic stirrer was charged with 104d (65 mg, 0.166 mmol), 102g (68 mg, 0.166 mmol), sodium carbonate (53 mg, 0.498 mmol) dioxane (1.0 mL) and water (0.2 mL). This mixture was degassed with nitrogen for 30 min. Tetrakis(triphenylphosphine)palladium (19 mg, 0.017 mmol) was added, and the tube was sealed. After heating at 110° C. (bath temperature) for 16 h, the reaction mixture was cooled to room temperature and concentrated to a residue. The resulting residue was purified by flash chromatography on silica gel. This material was further purified using a preparative HPLC to afford a 13% yield (12.5 mg) of 104 as a yellow solid: mp 174-176° C. dec; $^1$H NMR (500 MHz, DMSO-$d_6$) δ 9.19 (s, 1H), 7.91 (d, 2H, J=8.5 Hz), 7.82 (d, 1H, J=4.5 Hz), 7.43 (t, 2H, J=8.0 Hz), 7.34 (t, 1H, J=7.8 Hz), 7.22 (s, 1H), 7.19 (d, 2H, J=8.5 Hz), 7.14 (s, 1H), 4.78 (s, 2H), 3.55 (s, 3H), 3.52 (s, 1H), 3.40 (td, 1H, J=11.0, 3.5 Hz), 3.13 (m, 1H), 2.90 (dd, 1H, J=6.0, 3.0 Hz), 2.47 (m, 1H), 2.24 (s, 3H), 2.05 (s, 3H), 1.42 (s, 9H); MS (ESI+) m/z 597.7 (M+H).

Example 105

Example 105a

5-Bromo-3-(1,5-dimethyl-1H-pyrazol-3-ylamino)-1-methylpyridin-2(1H)-one 105a

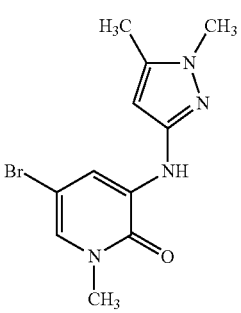

A 250-mL single-necked round-bottomed flask equipped with a magnetic stirrer and reflux condenser was charged with 3,5-dibromo-1-methylpyridin-2(1H)-one (1.50 g, 5.62 mmol), 1,5-dimethyl-3-amino-1H-pyrazole (625 mg, 5.62 mmol), cesium carbonate (5.48 g, 16.8 mmol) and 1,4-dioxane (36 mL). After bubbling nitrogen through the resulting solution for 30 min, Xantphos (553 mg, 0.955 mmol) and tris(dibenzylideneacetone)dipalladium(0) (625 mg, 0.562 mmol) were added and the reaction mixture was heated at reflux for 16 h. The reaction mixture was cooled to room temperature and the resulting precipitate was filtered off. The filter cake was washed with methylene chloride (approximately 20 mL). The resulting filtrate was then concentrated under reduced pressure and purified by column chromatography to afford 105a (935 mg, 56%) as a yellow solid: $^1$H NMR (300 MHz, CDCl$_3$) δ 7.84 (s, 1H), 7.31 (s, 1H), 6.86 (s, 1H), 5.65 (s, 1H), 3.71 (s, 3H), 3.57 (s, 3H), 2.23 (s, 3H); MS (ESI+) m/z 297.0 (M+H).

Example 105

5-tert-Butyl-2-(3-(5-(1,5-dimethyl-1H-pyrazol-3-ylamino)-1-methyl-6-oxo-1,6-dihydropyridin-3-yl)-2-(hydroxymethyl)phenyl)isoindolin-1-one 105

A 100-mL three-neck round-bottomed flask equipped with a magnetic stirrer and reflux condenser was charged with 103f (556 mg, 1.20 mmol), 105a (300 mg, 1.00 mmol), sodium carbonate (424 mg, 4.00 mmol), water (4 mL) and 1,4-dioxane (20 mL). After bubbling nitrogen through the resulting suspension for 20 min, tetrakis(triphenylphosphine)-palladium(0) (115 mg, 0.100 mmol) was added, and the reaction mixture was heated at 100° C. for 4 h. After this time, the reaction mixture was cooled to room temperature and filtered, and the filter cake was washed with a 1:10 mixture of methanol and methylene chloride (30 mL). The filtrate was concentrated under reduced pressure to afford a brown residue. Another 100-mL single-neck round-bottomed flask equipped with a magnetic stirrer and reflux condenser was charged with residue obtained above, THF (5 mL), ethanol (5 mL), water (5 mL) and lithium hydroxide (86.4 mg, 3.60 mmol). The mixture was stirred at 50° C. for 2 h. After this time, the reaction mixture was concentrated under reduced pressure. The resulting residue was purified by flash chromatography to afford a 35% (190 mg) yield of 105 as a white solid: mp 225-227° C.; $^1$H NMR (500 MHz, DMSO-d$_6$) δ 7.94 (s, 2H), 7.72 (d, 1H, J=7.5 Hz), 7.71 (s, 1H), 7.61 (d, 1H, J=7.5 Hz), 7.48 (t, 1H, J=7.5 Hz), 7.42 (d, 1H, J=7.5 Hz), 7.36 (d, 1H, J=7.5 Hz), 7.22 (s, 1H), 5.88 (s, 1H), 4.89 (s, 2H), 4.88 (t, 1H, J=4.5 Hz), 4.35 (d, 2H, J=4.5 Hz), 3.57 (s, 3H), 3.56 (s, 3H), 2.17 (s, 3H), 1.36 (s, 9H); MS (ESI+) m/z 512.3 (M+H).

Example 106

Example 106a

5-Bromo-3-(1-ethyl-1H-pyrazol-3-ylamino)-1-methylpyridin-2(1H)-one 106a

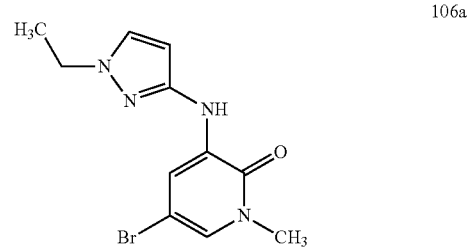 [SMILES: CCn1ccc(Nc2cc(Br)cn(C)c2=O)n1]

Following the same general procedure as described for 102k, reaction of 3,5-dibromo-1-methylpyridin-2(1H)-one (1.20 g, 4.50 mmol) with 1-ethyl-3-amino-1H-pyrazole 111b (500 mg, 4.50 mmol) gave a 23% (300 mg) yield of 106a as a white solid: mp 165-167° C.; $^1$H NMR (300 MHz, DMSO-d$_6$) δ 8.39 (s, 1H), 8.00 (d, 1H, J=2.7 Hz), 7.54 (d, 1H, J=2.4 Hz), 7.37 (d, 1H, J=2.4 Hz), 6.05 (d, 1H, J=2.4 Hz), 4.03 (t, 2H, J=7.2 Hz), 3.49 (s, 3H), 1.36 (t, 3H, J=7.2 Hz); MS (ESI+) m/z 298.1 (M+H).

Example 106

5-tert-Butyl-2-(3-(5-(1-ethyl-1H-pyrazol-3-ylamino)-1-methyl-6-oxo-1,6-dihydropyridin-3-yl)-2-(hydroxymethyl)phenyl)isoindolin-1-one 106

Following the same general procedure as described for 105, reaction of 103f (556 mg, 1.20 mmol) with 106a (300 mg, 1.00 mmol) gave a 20% (101 mg) yield of 106 as a white solid: mp 175-177° C.; $^1$H NMR (500 MHz, DMSO-d$_6$) δ 8.07 (s, 1H), 8.01 (d, 1H, J=2.0 Hz), 7.73 (d, 1H, J=7.5 Hz), 7.71 (s, 1H), 7.62 (dd, 1H, J=8.0, 1.0 Hz), 7.52 (d, 1H, J=2.5 Hz), 7.49 (t, 1H, J=7.5 Hz), 7.42 (dd, 1H, J=7.5, 1.0 Hz), 7.36 (dd, 1H, J=7.5, 1.0 Hz), 7.25 (d, 1H, J=2.0 Hz), 6.06 (d, 1H, J=2.0 Hz), 4.94 (s, 2H), 4.89 (t, 1H, J=5.0 Hz), 4.35 (d, 2H, J=5.0 Hz), 3.98 (q, 2H, J=7.5 Hz), 3.58 (s, 3H), 1.37 (s, 9H), 1.31 (t, 3H, J=7.5 Hz); MS (ESI+) m/z 512.3 (M+H).

Example 107

Example 107a

5-Bromo-1-methyl-3-(pyrimidin-4-ylamino)pyridin-2(1H)-one 107a

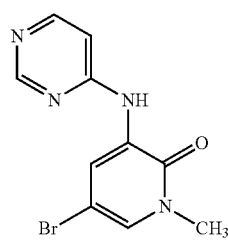

A 100-mL single-neck round-bottomed flask equipped with a magnetic stirrer and nitrogen inlet was charged with 3,5-dibromo-1-methylpyridin-2(1H)-one (2.00 g, 21.0 mmol), 2-aminopyrimidine (5.61 g, 21.0 mmol), cesium carbonate (13.7 g, 42.1 mmol), DMF (5 mL) and 1,4-dioxane (70 mL). After bubbling nitrogen through the resulting suspension for 30 min, Xantphos (1.10 g, 1.89 mmol) and tris(dibenzyl-ideneacetone)dipalladium(0) (963 mg, 1.05 mmol) were added. A reflux condenser was attached to the flask, and the reaction mixture was heated at 100° C. for 4 h. After this time, the mixture was cooled to room temperature and diluted with 90:10 methylene chloride/methanol (150 mL) and water (100 mL), and the layers were separated. The aqueous layer was extracted with 90:10 methylene chloride/methanol (50 mL), and the combined organic layers were washed with brine and dried over sodium sulfate. The drying agent was removed by filtration. The filtrate was concentrated under reduced pressure, and the resulting residue was purified by flash column chromatography (silica, 90:10 methylene chloride/methanol) to afford 107a in 58% yield (3.42 g) as an amorphous light green solid: mp 217-219° C.; $^1$H NMR (500 MHz, CDCl$_3$) δ 9.29 (s, 1H), 8.77 (s, 1H), 8.72 (d, J=2.5 Hz, 1H), 8.36 (d, J=6.0 Hz, 1H), 7.69 (d, J=2.5 Hz, 1H), 7.37 (dd, J=5.5, 1.0 Hz, 1H), 3.53 (s, 3H); MS (ESI+) m/z 281.0 (M+H).

Example 107

5-tert-Butyl-2-(2-(hydroxymethyl)-3-(1-methyl-6-oxo-5-(pyrimidin-4-ylamino)-1,6-dihydropyridin-3-yl)phenyl)isoindolin-1-one 107

Using the same general procedure as in Example 105, reaction of 107a (250 mg, 0.889 mmol) with 103f (495 mg, 1.07 mmol) afforded 107 in 38% yield (166 mg) as an amorphous off-white solid: mp 216-218° C.; $^1$H NMR (500 MHz, DMSO-d$_6$) δ 9.18 (s, 1H), 8.72 (d, J=2.0 Hz, 1H), 8.65 (s, 1H), 8.30 (d, J=5.5 Hz, 1H), 7.73 (d, J=8.5 Hz, 2H), 7.62 (dd, J=8.0, 1.5 Hz, 1H), 7.54 (d, J=2.0 Hz, 1H), 7.51 (t, J=7.5 Hz, 1H), 7.46 (dd, J=7.5, 1.0 Hz, 1H), 7.40 (dd, J=7.5, 1.5 Hz, 1H), 7.32 (dd, J=6.0, 1.0 Hz, 1H), 4.95 (s, 2H), 4.92 (t, J=4.5 Hz, 1H), 4.34 (d, J=5.0 Hz, 2H), 3.61 (s, 3H), 1.37 (s, 9H); MS (ESI+) m/z 496.2 (M+H).

Example 108

Example 108a

5-Bromo-1-methyl-3-(4-morpholinophenylamino)pyrazin-2(1H)-one 108a

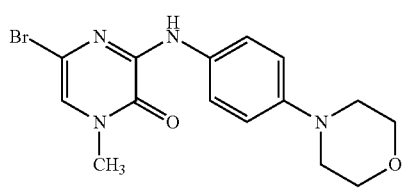

3,5-Dibromo-1-methylpyrazin-2(1H)-one (2.21 g) was reacted with 4-morpholinoaniline (1.48 g) using the same general procedure as Example 107a, whereby 108a was obtained as a grey solid in 115% crude yield (3.46 g): $^1$H NMR (500 MHz, DMSO-d$_6$) δ 9.49 (s, 1H), 7.87 (d, 2H, J=8.0 Hz), 7.31 (s, 1H), 7.21 (m, 2H), 3.83 (m, 4H), 3.43 (s, 3H), 3.27 (m, 4H); MS (ESI+) m/z 365 (M+H). This material contained 18 wt % of DL-10-camphorsulfonic acid. Corrected yield 2.83 g (94%).

Example 108

5-tert-Butyl-2-(2-(hydroxymethyl)-3-(4-methyl-6-(4-morpholinophenylamino)-5-oxo-4,5-dihydropyrazin-2-yl)phenyl)isoindolin-1-one 108

Using the same general procedure as Example 105, reaction of 108a (296 mg, 0.810 mmol) with 103f (413 mg, 0.891 mmol) afforded 108 in 47% yield (205 mg) as an amorphous yellow solid: mp 225-227° C.; $^1$H NMR (500 MHz, DMSO-d$_6$) δ 9.08 (s, 1H), 7.83 (d, J=9.0 Hz, 2H), 7.73 (d, J=8.5 Hz, 2H), 7.62 (dd, J=8.0, 1.5 Hz, 1H), 7.58 (dd, J=8.0, 1.5 Hz, 1H), 7.50 (t, J=7.5 Hz, 1H), 7.42 (dd, J=8.0, 1.0 Hz, 1H), 7.34 (s, 1H), 6.89 (d, J=9.0 Hz, 2H), 4.92 (s, 2H), 4.83 (t, J=5.0 Hz, 1H), 4.43 (d, J=5.0 Hz, 2H), 3.72 (t, J=5.5 Hz, 4H), 3.54 (s, 3H), 3.03 (t, J=5.5 Hz, 4H), 1.37 (s, 9H); MS (ESI+) m/z 580.3 (M+H).

Example 109

Example 109a

1-Cyclopropyl-4-nitro-1H-pyrazole 109a

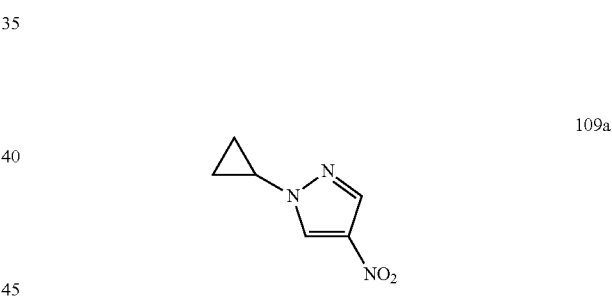

A 100-mL three-neck round-bottomed flask equipped with a reflux condenser and magnetic stirrer was purged with nitrogen and charged with 4-nitropyrazole (500 mg, 4.42 mmol), cyclopropylboronic acid (760 mg, 8.84 mmol), sodium carbonate (937 mg, 8.84 mmol), 2,2'-bipryidyl (690 mg, 4.42 mmol), and dichloroethane (45 mL). After bubbling nitrogen through the resulting suspension for 30 min, copper (II) acetate (802 mg, 4.42 mmol) was added, and the reaction mixture was heated at 70° C. (oil bath temperature) for 6 h. After this time, the mixture was cooled to room temperature and filtered. The filtrate was diluted with ethyl acetate (150 mL) and water (30 mL). The organic layer was separated, and the aqueous layer was extracted with ethyl acetate (3×50 mL). The combined organic layers were dried over sodium sulfate and concentrated under reduced pressure. The residue was purified by column chromatography (silica, 0% to 50% ethyl acetate/hexanes) to afford a 37% yield (185 mg) of 109a as an off-white solid: mp 44-45° C.; ¹H NMR (500 MHz, CDCl₃) δ 8.18 (s, 1H), 8.03 (s, 1H), 3.67 (s, 1H), 1.16 (m, 4H); MS (APCI+) m/z 154.1 (M+H).

Example 109b

1-Cyclopropyl-1H-pyrazol-4-amine 109b

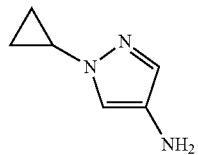

109b

A 250-mL Parr reactor bottle was purged with nitrogen and charged with 10% palladium on carbon (50% wet, 117 mg dry weight) and a solution of 109a (500 mg, 6.73 mmol) in ethanol (36 mL). The bottle was attached to a Parr hydrogenator, evacuated, charged with hydrogen gas to a pressure of 50 psi and shaken for 2 h. After this time, the hydrogen was evacuated, and nitrogen was charged into the bottle. Celite 521 (1.00 g) was added, and the mixture was filtered through a pad of Celite 521. The filter cake was washed with ethanol (2×25 mL), and the combined filtrates were concentrated to dryness under reduced pressure to afford a 94% yield of 109b (378 mg) as a purple oil: ¹H NMR (300 MHz, CDCl₃) δ 7.13 (s, 1H), 7.07 (s, 1H), 3.47 (m, 1H), 2.87 (br s, 2H), 0.96 (m, 4H); MS (ESI+) m/z 124.1 (M+H).

Example 109c

5-Bromo-3-(1-cyclopropyl-1H-pyrazol-4-ylamino)-1-methylpyrazin-2(1H)-one 109c

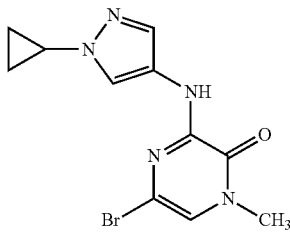

109c

A 100-mL three-neck round-bottomed flask equipped with a reflux condenser, magnetic stirrer and nitrogen inlet was charged with 109b (378 mg, 3.07 mmol), 3,5-dibromo-1-methylpyrazin-2(1H)-one (906 mg, 3.38 mmol), cesium carbonate (3.00 g, 9.21 mmol), and 1,4-dioxane (45 mL). After bubbling nitrogen through the resulting suspension for 30 min, Xantphos (151 mg, 0.261 mmol) and tris(dibenzylideneacetone)dipalladium(0) (141 mg, 0.154 mmol) were added, and the reaction mixture was heated at reflux for 3 h. After this time, the mixture was cooled to room temperature and diluted with ethyl acetate (150 mL) and water (30 mL). The organic layer was separated, and the aqueous layer was extracted with ethyl acetate (3×45 mL). The combined organic layers were dried over sodium sulfate and concentrated under reduced pressure. The residue was purified by column chromatography (silica, 0% to 10% methanol/methylene chloride) to afford a 28% yield (266 mg) of 109c as an off-white solid: mp 228-230° C.; ¹H NMR (300 MHz, DMSO-d₆) δ 9.90 (s, 1H), 8.06 (s, 1H), 7.69 (s, 1H), 7.21 (s, 1H), 3.70 (m, 1H), 3.41 (s, 3H), 0.96 (m, 4H); MS (ESI+) m/z 310.0 (M+H).

Example 109

5-tert-Butyl-2-(3-(6-(1-cyclopropyl-1H-pyrazol-4-ylamino)-4-methyl-5-oxo-4,5-dihydropyrazin-2-yl)-2-(hydroxymethyl)phenyl)isoindolin-1-one 109

Using the same general procedure as Example 105, reaction of 109c (310 mg, 1.00 mmol) and 103f (536 mg, 1.20 mmol) afforded a 35% yield (184 mg) of 109 as an off-white solid: mp 218-219° C.; ¹H NMR (500 MHz, DMSO-d₆) δ 9.58 (s, 1H), 8.20 (s, 1H), 7.73 (m, 3H), 7.61 (m, 2H), 7.51 (t, 1H, J=7.9 Hz), 7.43 (m, 1H), 7.31 (s, 1H), 4.95 (s, 2H), 4.90 (t, 1H, J=5.0 Hz), 4.48 (d, 2H, J=5.0 Hz), 3.64 (m, 1H), 3.52 (s, 3H), 1.37 (s, 9H), 0.93 (m, 4H); MS (ESI+) m/z 525.2 (M+H).

Example 110

Example 110a

5-Bromo-3-(3-cyclopropyl-1H-pyrazol-5-ylamino)-1-methylpyridin-2(1H)-one 110a

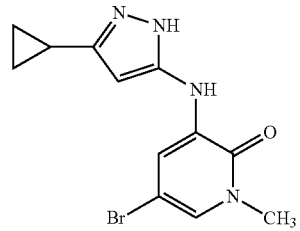

110a

Using the same general procedure as Example 109c, reaction of 3-cyclopropyl-5-amino-1H-pyrazole (500 mg, 4.06 mmol) and 3,5-dibromo-1-methylpyridin-2(1H)-one (1.08 g, 4.06 mmol) afforded a 21% yield (260 mg) of 110a as an off-white solid: mp 203-204° C.; ¹H NMR (500 MHz, DMSO-d₆) δ 8.20 (s, 1H), 8.02 (d, 1H, J=2.5 Hz), 7.34 (d, 1H, J=2.5 Hz), 5.77 (d, 1H, J=2.1 Hz), 3.48 (s, 3H), 1.84 (m, 1H), 0.90 (m, 4H), 0.63 (m, 4H); MS (ESI+) m/z 309.0 (M+H).

Example 110

5-tert-Butyl-2-(3-(5-(3-cyclopropyl-1H-pyrazol-5-ylamino)-1-methyl-6-oxo-1,6-dihydropyridin-3-yl)-2-(hydroxymethyl)phenyl)isoindolin-1-one 110

Using the same general procedure as Example 105, reaction of 110a (260 mg, 0.841 mmol) and 103f (429 mg, 0.926 mmol) afforded a 33% yield (144 mg) of 110 as an off-white solid: mp 178-180° C.; ¹H NMR (500 MHz, DMSO-d₆) δ 11.76 (d, 1H, J=2.0 Hz), 7.98 (d, 1H, J=2.0 Hz), 7.92 (s, 1H), 7.71 (m, 2H), 7.61 (dd, 1H, J=7.9, 1.6 Hz), 7.48 (m, 1H), 7.42 (dd, 1H, J=7.6, 1.1 Hz), 7.35 (dd, 1H, J=7.6, 1.1 Hz), 7.23 (d, 1H, J=2.1 Hz), 5.79 (d, 1H, J=2.2 Hz), 4.93 (s, 2H), 4.90 (t, 1H, J=4.9 Hz), 4.35 (d, 2H, J=4.6 Hz), 3.57 (s, 3H), 1.81 (m, 1H), 1.37 (s, 9H), 0.89 (m, 2H), 0.64 (m, 2H); MS (ESI+) m/z 524.2 (M+H).

Example 111

Example 111a

1-Ethyl-4-nitro-1H-pyrazole 111a

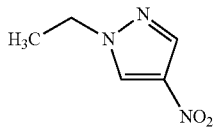

111a

A 250-mL single-neck round-bottomed flask equipped with a magnetic stirrer was purged with nitrogen inlet and charged with 4-nitropyrazole (3.00 g, 26.5 mmol) and DMF (50 mL). The mixture was cooled to 0° C. using an ice bath. Sodium hydride (60% dispersion in mineral oil, 1.17 g, 29.2 mmol) was added portionwise. After the addition was complete, the mixture was stirred at 0° C. for 30 min. After that time, iodoethane (6.21 g, 39.8 mmol) was added over 15 min. After the addition was complete, the mixture was stirred at 0° C. for 30 min and then at room temperature for 3 h. After this time, the mixture was concentrated in vacuo. The residue was diluted with water (200 mL). The resulting precipitate was filtered, and the filter cake was dried in the oven to afford a 51% (1.90 g) of 111a as an off-white solid. The aqueous layer was extracted with ethyl acetate (3×150 mL). The combined organic layers were dried over sodium sulfate and concentrated under reduced pressure. The residue was purified by column chromatography (silica, 0% to 50% hexanes/ethyl acetate) to afford another 49% yield (1.84 g, in total quantitative yield (3.74 g)) of 111a as an off-white solid: mp 54-55° C.; $^1$H NMR (300 MHz, CDCl$_3$) δ 8.14 (s, 1H), 8.07 (s, 1H), 4.22 (q, 2H, J=7.2 Hz), 3.41 (s, 3H), 1.56 (s, 3H, J=7.2 Hz); MS (ESI+) m/z 142.0 (M+H).

Example 111b

1-Ethyl-1H-pyrazol-4-amine 111b

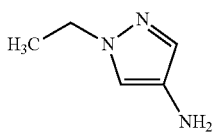

111b

A 250-mL Parr reactor bottle was purged with nitrogen and charged with 10% palladium on carbon (50% wet, 468 mg dry weight) and a solution of 111a (1.90 g, 13.5 mmol) in ethanol (100 mL). The bottle was attached to a Parr hydrogenator, evacuated, charged with hydrogen gas to a pressure of 50 psi and shaken for 3 h. After this time, the hydrogen was evacuated, and nitrogen was charged into the bottle. Celite 521 (1.00 g) was added, and the mixture was filtered through a pad of Celite 521. The filter cake was washed with ethanol (2×25 mL), and the combined filtrates were concentrated to dryness under reduced pressure to afford a quantitative yield of 111b (1.50 g) as a purple oil: $^1$H NMR (300 MHz, CDCl$_3$) δ 7.15 (s, 1H), 7.02 (s, 1H), 4.05 (q, 2H, J=7.2 Hz), 2.88 (br s, 2H), 1.43 (t, 3H, J=7.2 Hz); MS (ESI+) m/z 112.1 (M+H).

Example 111c

5-Bromo-3-(1-ethyl-1H-pyrazol-4-ylamino)-1-methylpyrazin-2(1H)-one 111c

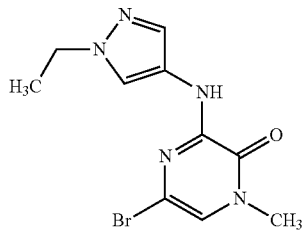

111c

Using the same general procedure as Example 102k, reaction of 111b (500 mg, 4.50 mmol) and 3,5-dibromo-1-methylpyrazin-2(1H)-one (1.33 g, 4.95 mmol) afforded a 75% yield (1.01 g) of 111c as an off-white solid: mp 237-239° C.; $^1$H NMR (300 MHz, DMSO-d$_6$) δ 9.90 (s, 1H), 8.02 (s, 1H), 7.73 (s, 1H), 7.20 (s, 1H), 4.11 (q, 2H, J=7.5 Hz), 3.41 (s, 3H), 1.34 (t, 3H, J=7.3 Hz); MS (ESI+) m/z 298.0 (M+H).

Example 111

5-tert-Butyl-2-(3-(6-(1-ethyl-1H-pyrazol-4-ylamino)-4-methyl-5-oxo-4,5-dihydropyrazin-2-yl)-2-(hydroxymethyl)phenyl)isoindolin-1-one 111

Using the same general procedure as Example 105, reaction of 111c (253 mg, 0.85 mmol) and 103f (473 mg, 1.02 mmol) afforded a 48% yield (210 mg) of 111 as an off-white solid: mp 138-140° C.; $^1$H NMR (500 MHz, DMSO-d$_6$) δ 9.57 (s, 1H), 8.17 (s, 1H), 7.72 (m, 3H), 7.61 (m, 2H), 7.51 (t, 1H, J=7.6 Hz), 7.43 (m, 1H), 7.31 (s, 1H), 4.94 (s, 2H), 4.88 (t, 1H, J=5.0 Hz), 4.49 (d, 2H, J=5.0 Hz), 4.06 (q, 2H, J=7.1 Hz), 3.52 (s, 3H), 1.37 (s, 9H), 1.33 (t, 3H, J=7.2 Hz); MS (ESI+) m/z 513.2 (M+H).

Example 112

Example 112a

5-Bromo-1-methyl-3-(pyridin-3-ylamino)pyrazin-2(1H)-one 112a

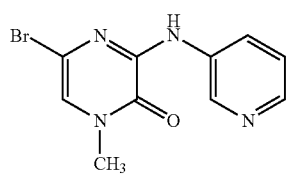

112a

A 100-mL single-neck round-bottomed flask equipped with a magnetic stirrer, reflux condenser and nitrogen inlet was charged with THF (15 mL), 3,5-dibromo-1-methylpyrazin-2(1H)-one (1.00 g, 3.73 mmol), 3-aminopyridine (351 mg, 3.73 mmol) and sodium tert-butoxide (789 mg, 8.21 mmol). After bubbling nitrogen through the resulting solution for 30 min, Pd2Br2(t-Bu3P)2 (29 mg, 0.037 mmol) was added, and the reaction mixture was stirred at room temperature for 2.5 h. After this time the reaction was partitioned between ethyl acetate (50 mL) and water (50 mL) and filtered. The aqueous layer was separated and extracted with ethyl acetate (2×25 mL). The organic layers were combined, washed with brine (50 mL) and dried over sodium sulfate. The drying agent was removed by filtration and the filtrate concentrated under reduced pressure. The resulting residue was purified by column chromatography to afford a 35% yield (370 mg) of 112a as a brown solid: mp>250° C.; $^1$H NMR (500 MHz, DMSO-$d_6$) δ 9.75 (s, 1H), 9.08 (d, 1H, J=2.5 Hz), 8.32 (m, 1H), 8.24 (dd, 1H, J=5.0, 1.5 Hz), 7.40 (s, 1H), 7.36 (dd, 1H, J=8.5, 4.5 Hz), 3.45 (s, 3H); MS (APCI+) m/z 281.0 (M+H).

Example 112

5-tert-Butyl-2-(2-(hydroxymethyl)-3-(4-methyl-5-oxo-6-(pyridin-3-ylamino)-4,5-dihydropyrazin-2-yl)phenyl)isoindolin-1-one 112

A 100-mL single-neck round-bottomed flask equipped with a magnetic stirrer and reflux condenser was purged with nitrogen and charged with 103f (298 mg, 0.643 mmol), 112a (150 mg, 0.536 mmol), sodium carbonate (170 mg, 1.61 mmol), 1,4-dioxane (5 mL) and water (1 mL). This mixture was degassed with nitrogen for 30 min. Tetrakis(triphenylphosphine)palladium (62 mg, 0.054 mmol) was added. After heating at 100° C. for 3 h, the reaction mixture was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was dissolved in a mixture of methanol (5 mL), and potassium carbonate (500 mg, 3.62 mmol) was added. After stirring at room temperature for 2 h, the reaction mixture was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was purified by flash chromatography to afford 112 in 27% yield (70 mg) as an off-white solid: mp 149-150° C.; $^1$H NMR (500 MHz, DMSO-$d_6$) δ 9.54 (s, 1H), 9.14 (d, 1H, J=2.0 Hz), 8.44 (m, 1H), 8.18 (dd, 1H, J=5.0, 1.5 Hz), 7.73-7.71 (m, 2H), 7.63-7.59 (m, 2H), 7.52 (t, 1H, J=8.0 Hz), 7.48 (s, 1H), 7.44 (dd, 1H, J=8.0, 1.5 Hz), 7.30 (dd, 1H, J=7.5, 4.5 Hz), 4.93 (s, 2H), 4.88 (t, 1H, J=5.0 Hz), 4.44 (d, 2H, J=5.0 Hz), 3.56 (s, 3H), 1.37 (s, 9H); MS (ESI+) m/z 496.2 (M+H).

Example 113

Example 113a

5-Bromo-1-methyl-3-(pyridin-2-ylamino)pyridin-2(1H)-one 113a

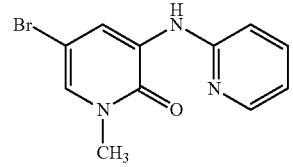

A 100-mL single-neck round-bottomed flask equipped with a magnetic stirrer, nitrogen inlet and reflux condenser was charged with 3,5-dibromo-1-methylpyridin-2(1H)-one (936 mg, 3.51 mmol), 2-aminopyridine (300 mg, 3.19 mmol), cesium carbonate (3.11 g, 9.57 mmol) and 1,4-dioxane (20 mL). After bubbling nitrogen through the resulting solution for 20 minutes, Xantphos (184 mg, 0.319 mmol) and tris(dibenzylideneacetone)dipalladium(0) (146 mg, 0.160 mmol) were added, and the reaction mixture was heated at 100° C. for 3 h. After this time, the reaction was cooled to room temperature, filtered and concentrated under reduced pressure. The resulting residue was purified by flash chromatography to afford a 42% yield (376 mg) of 1113a as an off-white solid: mp 153-154° C.; $^1$H NMR (300 MHz, DMSO-$d_6$) δ 8.75 (s, 1H), 8.69 (d, 1H, J=2.4 Hz), 8.26 (dd, 1H, J=5.4, 1.5 Hz), 7.61 (m, 1H), 7.54 (d, 1H, J=2.4 Hz), 7.33 (d, 1H, J=5.4 Hz), 6.86 (m, 1H), 3.45 (s, 3H).

Example 113

5-tert-Butyl-2-(2-(hydroxymethyl)-3-(1-methyl-6-oxo-5-(pyridin-2-ylamino)-1,6-dihydropyridin-3-yl)phenyl)isoindolin-1-one 113

Using the same general procedure as described for the preparation of 105, reaction 103f (298 mg, 0.643 mmol) with 113a (150 mg, 0.536 mmol) gave a 34% yield (90 mg) of 113 as a white solid: mp 138-139° C.; $^1$H NMR (500 MHz, DMSO-$d_6$) δ 8.68 (d, 1H, J=2.0 Hz), 8.58 (d, 1H), 8.17 (m, 1H), 7.73-7.71 (m, 2H), 7.62-7.56 (m, 2H), 7.50 (t, 1H, J=7.5 Hz), 7.44 (d, 1H, J=7.5 Hz), 7.39-7.37 (m, 2H), 7.28 (d, 1H, J=7.5 Hz), 6.78 (dd, 1H, J=6.5, 5.0 Hz), 4.94 (s, 2H), 4.89 (t, 1H, J=4.5 Hz), 4.34 (d, 2H, J=4.5 Hz), 3.60 (s, 3H), 1.65 (s, 9H); MS (ESI+) m/z 495.2 (M+H).

Example 114

Example 114a

1-Bromo-2-(bromomethyl)-3-nitrobenzene 114a

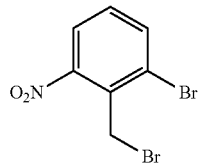

A 250-mL single-neck round-bottomed flask equipped with a magnetic stirrer and reflux condenser was charged with 1-bromo-2-methyl-3-nitrobenzene (6.86 g, 31.8 mmol) and carbon tetrachloride (40 mL) and heated to 80° C. N-bromosuccinimide (6.96 g, 39.1 mmol) and 2,2'-azobis(2-methylpropionitrile) (522 mg, 3.18 mmol) were added, and the reaction mixture was stirred at 80° C. for 16 h. After this time, the reaction mixture was cooled to room temperature and filtered, and the filter cake was washed with methylene chloride (20 mL). The filtrate was concentrated under reduced pressure to afford crude 114a (9.64 g, 103% crude yield) as a yellow oil, which was used directly in the next step: $^1$H NMR (500 MHz, CDCl$_3$) δ 7.89-7.86 (m, 2H), 7.35 (t, 1H, J=8.0 Hz), 4.89 (s, 2H).

Example 114b

2-Bromo-6-nitrobenzyl Acetate 114b

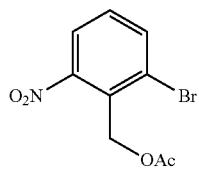

A 250-mL single-neck round-bottomed flask equipped with a magnetic stirrer was purged with nitrogen and charged with crude 114a prepared above (9.64 g, 31.8 mmol, presuming quantitative yield), potassium acetate (12.9 g, 131 mmol) and DMF (75 mL). After heating at 70° C. for 30 min, the reaction mixture was cooled to room temperature and partitioned between water (200 mL) and ethyl acetate (400 mL). The layers were separated, and the aqueous phase was extracted with ethyl acetate (2×100 mL). The organic extracts were combined, dried over sodium sulfate, filtered and concentrated under reduced pressure. The resulting residue was purified by flash chromatography to afford 114b in 62% yield (5.54 g) as a yellow solid: mp 36-37° C.; $^1$H NMR (500 MHz, CDCl$_3$) δ 7.85 (dd, 1H, J=8.0, 1.0 Hz), 7.77 (dd, 1H, J=8.0, 1.0 Hz), 7.38 (t, 1H, J=8.0 Hz), 5.46 (s, 2H), 2.06 (s, 3H).

Example 114c (2-Bromo-6-nitrobenzyloxy)(tert-butyl)dimethylsilane 114c

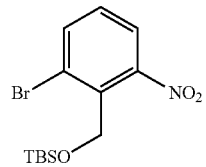

A 150-mL single-neck round-bottomed flask equipped with a magnetic stirrer and nitrogen inlet was charged with a solution of 114b (11.6 g, 42.3 mmol) in a mixture of THF (20 mL), ethanol (20 mL) and water (20 mL). Lithium hydroxide monohydrate (7.00 g, 167.0 mmol) was added and the reaction was stirred at room temperature for 1 h. After this time, the reaction mixture was partitioned between water (200 mL) and ethyl acetate (400 mL). The layers were separated, and the aqueous phase was extracted with ethyl acetate (2×200 mL). The organic extracts were combined, dried over sodium sulfate, filtered and concentrated under reduced pressure. The resulting residue was dissolved in anhydrous methylene chloride (50 mL). Imidazole (14.4 g, 68.0 mmol) was added, followed by dropwise addition of tert-butyldimethylchlorosilane (16.0 g, 106 mmol). The mixture was stirred at room temperature for 14 h. After this time, water (200 mL) was added and the layers separated. The aqueous layer was extracted with methylene chloride (2×200 mL) and the combined organic layers were washed with brine, and dried over sodium sulfate. The drying agent was removed by filtration and the filtrate was concentrated under reduced pressure. The resulting residue was purified by flash chromatography to afford an 89% yield (13.1 g) of 114c as a white semi-solid: $^1$H NMR (500 MHz, CDCl$_3$) δ 7.67 (d, 1H, J=8.5 Hz), 7.54 (d, 1H, J=8.5 Hz), 7.18 (t, 1H, J=8.0 Hz), 4.96 (s, 2H), 0.80 (s, 9H), 0.007 (s, 6H).

Example 114d

3-Bromo-2-((tert-butyldimethylsilyloxy)methyl)aniline 114d

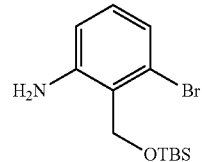

A 100-mL three-neck round-bottomed flask equipped with a magnetic stirrer and reflux condenser was charged with 114c (1.00 g, 2.89 mmol), ethanol (20 mL), iron powder (−325 mesh, 1.62 g, 28.9 mmol), ammonium chloride (3.09 g, 57.8 mmol) and water (4 mL), and the reaction mixture was heated at 80° C. for 1 h. After this time, the reaction mixture was cooled to room temperature and filtered through a pad of Celite 521. The filter cake was washed with ethanol (3×50 mL), and the combined filtrates were concentrated under reduced pressure. The resulting residue was triturated with water (10 mL) and then dried to a constant weight at 45° C. under vacuum to afford 114d in quantitative yield (949 mg) as a yellow solid: $^1$H NMR (500 MHz, CDCl$_3$) δ 6.82 (m, 2H), 6.53 (m, 1H), 4.86 (s, 2H), 4.68 (br s, 2H), 0.79 (s, 9H), 0.00 (s, 6H).

Example 114e

Methyl 3-((3-Bromo-2-((tert-butyldimethylsilyloxy) methyl)-phenylamino)methyl)-5-tert-butylthiophene-2-carboxylate 114e

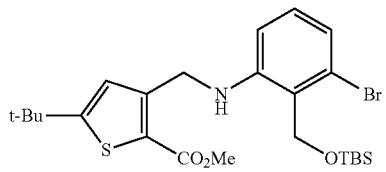

114e

A 100-mL single-necked round-bottomed flask equipped with a magnetic stirrer was purged with nitrogen and charged with 114d (875 mg, 3.00 mmol), methyl 2-bromomethyl-5-t-butyl-thiophene-1-carboxylate (949 mg, 3.00 mmol) and acetonitrile (10 mL). Cesium carbonate (1.95 g, 6.00 mmol) was added and the mixture was stirred at 40° C. for 16 h. The reaction mixture was then concentrated under reduced pressure. Purification of the resulting residue by column chromatography afforded a 70% yield (1.10 g) of 114e as a colorless oil: $^1$H NMR (500 MHz, CDCl$_3$) δ 6.86 (t, 1H, J=8.0 Hz), 6.82-6.78 (m, 2H), 6.48 (d, 1H, J=8.0 Hz), 4.90 (s, 2H), 4.58 (s, 2H), 3.77 (s, 3H), 1.24 (s, 9H), 0.76 (s, 9H), 0.09 (s, 6H).

Example 114f 3-((3-Bromo-2-(hydroxymethyl)phenylamino)methyl)-5-tert-butylthiophene-2-carboxylic Acid 114f

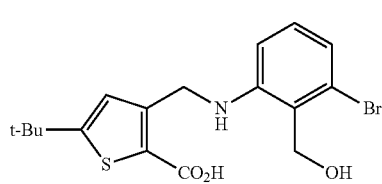

114f

A 50-mL single-necked round-bottomed flask equipped with a magnetic stirrer was charged with 114e (1.10 g, 2.09 mmol), lithium hydroxide (201 mg, 8.36 mmol), THF (10 mL), ethanol (10 mL) and water (10 mL). After stirring at room temperature for 2 h, the solvent was removed under reduced pressure and the resulting residue was acidified with 2N hydrochloric acid to pH of 4. The resulting aqueous solution was extracted with ethyl acetate (3×30 mL), and the organic extracts were combined and dried over sodium sulfate, filtered and concentrated under reduced pressure. The resulting residue was purified by flash chromatography to afford 114f in 65% yield (540 mg) as a white solid: mp 68-69° C.; $^1$H NMR (500 MHz, CDCl$_3$) δ 7.03-6.97 (m, 2H), 6.86 (s, 1H), 6.71 (d, 1H, J=8.0 Hz), 4.94 (s, 2H), 4.60 (s, 2H), 1.35 (s, 9H); MS (ESI+) m/z 398.0 (M+H).

Example 114g 5-(3-Bromo-2-(hydroxymethyl)phenyl)-2-tert-butyl-4H-thieno[3,2-c]pyrrol-6(5H)-one 114g

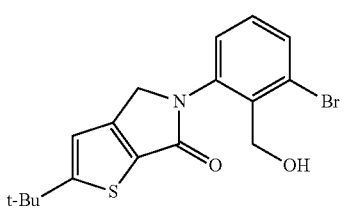

114g

A 50-mL single-neck round-bottomed flask equipped with a magnetic stirrer was purged with nitrogen and charged with 114f (540 mg, 1.36 mmol), triethylamine (275 mg, 2.72 mmol) and anhydrous DMF (10 mL). Benzotriazol-1-yl-oxy-tris(dimethylamino)phosphonium hexafluorophosphate (BOP, 782 mg, 1.77 mmol) was added, and the reaction was stirred at room temperature for 16 h. After this time, the reaction was diluted with water (20 mL), and the resulting suspension was filtered. The filter cake was dissolved in methylene chloride (40 mL), and the solution was washed with saturated aqueous sodium bicarbonate (10 mL), and water (10 mL), and dried over sodium sulfate. The drying agent was removed by filtration, and the solvent was evaporated under reduced pressure. The resulting residue was purified by flash chromatography to afford a 60% yield of 114g (305 mg) as a white solid: mp 55-56° C.; $^1$H NMR (500 MHz, CDCl$_3$) δ 7.65 (d, 1H, J=8.0 Hz), 7.25 (m, 1H), 7.20 (d, 1H, J=8.0 Hz), 6.89 (s, 1H), 4.68 (s, 2H), 4.66 (s, 2H), 1.46 (s, 9H).

Example 114h

2-Bromo-6-(2-tert-butyl-6-oxo-4H-thieno[3,2-c]pyrrol-5(6H)-yl)benzyl Acetate 114h

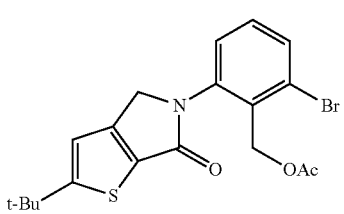

114h

A 100-mL single-neck round-bottomed flask equipped with a magnetic stirrer was purged with nitrogen and charged with 114g (240 mg, 0.633 mmol), pyridine (150 mg, 1.90 mmol) and methylene chloride (10 mL). The solution was cooled to 0° C., and acetyl chloride (75 mg, 0.950 mmol) was added. The cooling bath was then removed, and the reaction mixture was stirred at room temperature for 1 h. After this time, the reaction mixture was partitioned between water (5 mL) and methylene chloride (5 mL), and the layers were separated. The aqueous phase was extracted with methylene chloride (2×10 mL), and the combined organic extracts were washed with saturated aqueous sodium bicarbonate (10 mL), water (10 mL) and brine (10 mL). The organic extracts were dried over sodium sulfate, filtered and concentrated under reduced pressure. The resulting residue was purified by flash chromatography to afford 114h in 86% yield (231 mg) as a white solid: mp 172-173° C.; $^1$H NMR (500 MHz, CDCl$_3$) δ 7.63 (d, 1H, J=8.0 Hz), 7.34-7.21 (m, 2H), 6.87 (s, 1H), 5.21 (s, 2H), 4.64 (s, 2H), 2.05 (s, 3H), 1.42 (s, 9H).

Example 114i 2-(2-tert-Butyl-6-oxo-4H-thieno[3,2-c]pyrrol-5(6H)-yl)-6-(4,4,5,5-tetramethyl-1,3,2-dioxaborolan-2-yl) benzyl Acetate 114i

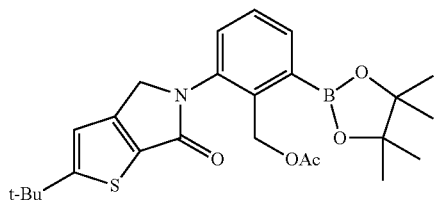

A 100-mL single-neck round-bottomed flask equipped with a magnetic stirrer and thermoregulator was purged with nitrogen and charged with 114h (310 mg, 0.735 mmol), 4,4,4',4',5,5,5',5'-octamethyl-2,2'-bi(1,3,2-dioxaborolane) (551 mg, 2.20 mmol), potassium acetate (216 mg, 2.21 mmol) and 1,4-dioxane (5 mL). A stream of nitrogen was passed through the resulting suspension for 30 min. PddppfCl2.CH$_2$Cl$_2$ (54 mg, 0.074 mmol) was then added and the reaction stirred at reflux for 5 h. After this time, the mixture was cooled to ambient temperature, partitioned between water (25 mL) and tert-butyl methyl ether (50 mL) and filtered through a plug of Celite 521. The organic phase was separated, dried over sodium sulfate, filtered and concentrated under reduced pressure, the resulting residue was purified by flash chromatography to afford 77% yield (265 mg) of 114i as a yellow solid: mp 62-63° C.; $^1$H NMR (500 MHz, CDCl$_3$) δ 7.85 (d, 1H, J=8.0 Hz), 7.44 (t, 1H, J=8.0 Hz), 7.37 (d, 1H, J=8.0 Hz), 6.86 (s, 1H), 5.33 (s, 2H), 4.62 (s, 2H), 1.96 (s, 3H), 1.45 (s, 9H), 1.33 (s, 12H).

Example 114

2-tert-Butyl-5-(2-(hydroxymethyl)-3-(1-methyl-5-(5-methyl-4,5,6,7-tetrahydropyrazolo[1,5-a]pyrazin-2-ylamino)-6-oxo-1,6-dihydropyridin-3-yl)phenyl)-4H-thieno[3,2-c]pyrrol-6(5H)-one 114

A 100-mL single-neck round-bottomed flask equipped with a magnetic stirrer and reflux condenser was purged with nitrogen and charged with 114i (264 mg, 0.563 mmol), 103l (190 mg, 0.563 mmol), sodium carbonate (179 mg, 1.69 mmol), 1,4-dioxane (5 mL) and water (1 mL). This mixture was degassed with nitrogen for 30 min. Tetrakis(triphenylphosphine)palladium (65 mg, 0.056 mmol) was added. After heating at reflux for 3 h, the reaction mixture was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was dissolved in a mixture of methanol (5 mL), and potassium carbonate (500 mg, 3.62 mmol) was added. After stirring at room temperature for 2 h, the reaction mixture was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was purified by flash chromatography to afford 114 in 18% yield (57 mg) as an off-white solid: mp 164-165° C.; $^1$H NMR (500 MHz, DMSO-d$_6$) δ 8.10 (s, 1H), 7.97 (d, 1H, J=2.5 Hz), 7.46 (t, 1H, J=8.0 Hz), 7.39 (dd, 1H, J=8.0, 1.5 Hz), 7.34 (dd, 1H, J=8.0, 1.5 Hz), 7.22 (d, 1H, J=2.5 Hz), 7.15 (s, 1H), 5.87 (s, 1H), 4.89 (t, 1H, J=4.5 Hz), 4.84 (s, 2H), 4.34 (d, 2H, J=4.5 Hz), 3.91 (t, 2H, J=5.0 Hz), 3.57 (s, 3H), 3.48 (s, 2H), 2.77 (t, 2H, J=5.0 Hz), 2.36 (s, 3H), 1.42 (s, 9H); MS (APCI+) m/z 559.4 (M+H).

Example 115

Example 115a

5-Bromo-3-(1-cyclopropyl-1H-pyrazol-3-ylamino)-1-methylpyridin-2(1H)-one 115a

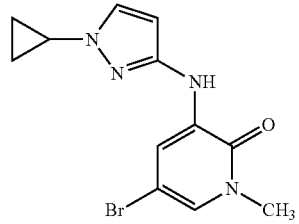

A 250-mL three-neck round-bottomed flask equipped with a reflux condenser, magnetic stirrer and nitrogen inlet was charged with 109b (444 mg, 3.61 mmol), 3,5-dibromo-1-methylpyridin-2(1H)-one (1.06 g, 3.97 mmol), cesium carbonate (3.52 g, 10.8 mmol), and 1,4-dioxane (45 mL). After bubbling nitrogen through the resulting suspension for 30 min, Xantphos (177 mg, 0.306 mmol) and tris(dibenzylidenea-cetone)dipalladium(0) (165 mg, 0.180 mmol) were added, and the reaction mixture was heated at reflux for 3 h. After this time, the mixture was cooled to room temperature and diluted with ethyl acetate (150 mL) and water (30 mL). The organic layer was separated, and the aqueous layer was extracted with ethyl acetate (3×150 mL). The combined organic layers were dried over sodium sulfate and concentrated under reduced pressure. The residue was triturated with methanol (20 mL) to afford a 63% yield (700 mg) of 115a as an off-white solid: mp 161-163° C.; $^1$H NMR (300 MHz, DMSO-d$_6$) δ 8.42 (s, 1H), 8.00 (d, 1H, J=2.5 Hz), 7.57 (d, 1H, J=2.4 Hz), 7.38 (d, 1H, J=2.5 Hz), 6.05 (d, 1H, J=2.4 Hz), 3.61 (m, 1H), 3.49 (s, 1H), 0.95 (m, 4H); MS (ESI+) m/z 309.0 (M+H).

Example 115

5-tert-Butyl-2-(3-(5-(1-cyclopropyl-1H-pyrazol-3-ylamino)-1-methyl-6-oxo-1,6-dihydropyridin-3-yl)-2-(hydroxymethyl)phenyl)isoindolin-1-one 115

A 50-mL three-neck round-bottomed flask equipped with a reflux condenser, magnetic stirrer and nitrogen inlet was charged with 115a (263 mg, 0.850 mmol), 103f (473 mg, 1.02 mmol), sodium carbonate (270 mg, 2.55 mmol), DMF (5 mL), water (2.5 mL) and 1,4-dioxane (8 mL). After bubbling nitrogen through the resulting suspension for 30 min, tetrakis(triphenylphosphine)palladium(0) (98 mg, 0.085 mmol) was added, and the reaction mixture was heated at reflux for 14 h. After this time, the mixture was cooled to room temperature and diluted with ethyl acetate (150 mL) and water (30 mL). The organic layer was separated, and the aqueous layer was extracted with ethyl acetate (3×150 mL). The combined organic layers were dried over sodium sulfate and concentrated under reduced pressure. The residue was dissolved in a mixture of THF (8 mL), methanol (4 mL) and water (4 mL). To the resulting solution was added lithium hydroxide monohydrate (420 mg, 10.0 mmol). The mixture was stirred for 4 h at room temperature and then concentrated in vacuo. The residue was partitioned between ethyl acetate (150 mL) and water (30 mL). The organic layer was separated, and the aqueous layer was extracted with a 20% (v/v) solution of methanol in methylene chloride (3×150 mL). The combined organic layers were dried over sodium sulfate and concentrated under reduced pressure. The residue was purified by column chromatography (silica, 0% to 10% methanol/methylene chloride) to afford a 39% yield (175 mg) of 115 as an off-white solid: mp 173-175° C.; $^1$H NMR (500 MHz, DMSO-$d_6$) δ 8.10 (s, 1H), 8.08 (d, 1H, J=2.5 Hz), 7.71 (m, 2H), 7.61 (dd, 1H, J=7.9, 1.5 Hz), 7.55 (d, 1H, J=2.5 Hz), 7.50 (m, 1H), 7.43 (dd, 1H, J=7.9, 1.5 Hz), 7.38 (dd, 1H, J=8.0, 1.5 Hz), 7.25 (d, 1H, J=2.1 Hz), 6.06 (d, 1H, J=2.4 Hz), 4.94 (s, 2H), 4.89 (t, 1H, J=4.5 Hz), 4.35 (d, 2H, J=4.5 Hz), 3.58 (s, 3H), 3.54 (m, 1H), 1.37 (s, 9H), 0.96 (m, 2H), 0.87 (m, 2H); MS (ESI+) m/z 524.2 (M+H).

Example 116

Example 116a

1-Methyl-3-(pyrimidin-4-ylamino)-5-(4,4,5,5-tetramethyl-1,3,2-dioxaborolan-2-yl)pyridin-2(1H)-one 116a

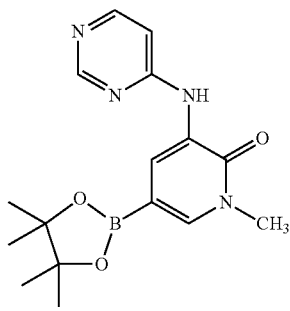

2c

A 100-mL single-neck round-bottomed flask equipped with a reflux condenser, magnetic stirrer and nitrogen inlet was charged with 107a (300 mg, 1.07 mmol), 4,4,4',4',5,5,5',5'-octamethyl-2,2'-bi(1,3,2-dioxaborolane) (543 mg, 2.14 mmol), potassium acetate (315 mg, 3.21 mmol), and 1,4-dioxane (7 mL). After bubbling nitrogen through the resulting suspension for 30 min, [1,1'-bis(diphenyl-phosphino)ferrocene]dichloropalladium(II) (78 mg, 0.107 mmol) was added, and the reaction mixture was heated at reflux for 1 h. After this time, the mixture was cooled to room temperature and diluted with ethyl acetate (150 mL) and water (30 mL). The organic layer was separated, and the aqueous layer was extracted with ethyl acetate (3×150 mL). The combined organic layers were dried over sodium sulfate and concentrated under reduced pressure. The residue was triturated with 80% (v/v) hexanes/ethyl acetate solution (20 mL) to afford a 71% yield (250 mg) of 116a as an off-white solid: mp 161-163° C.; $^1$H NMR (300 MHz, DMSO-$d_6$) δ 9.05 (s, 1H), 8.70 (s, 1H), 8.58 (d, 1H, J=2.4 Hz), 8.28 (d, 1H, J=5.9 Hz), 7.69 (d, 1H, J=1.5 Hz), 7.26 (d, 1H, J=5.9 Hz) 3.57 (s, 3H), 1.29 (s, 12H); MS (ESI+) m/z 329.2 (M+H).

Example 116b

Methyl 3-Methylthiophene-2-carboxylate 116b

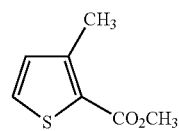

2e

A 500-mL single-neck round-bottomed flask equipped with a magnetic stirrer was purged with nitrogen inlet and charged with 2-methylthioophene-1-carboxylic acid (15.0 g, 105 mmol) and methanol (250 mL). The mixture was cooled to 0° C. using an ice bath. Thionyl chloride (15.5 ml, 25.1 g, 211 mmol) was added portionwise. After the addition was complete, the bath was removed and the reaction mixture was heated at 90° C. (oil bath temperature) for 14 h. After this time, the mixture was cooled to room temperature and concentrated in vacuo. The residue was dissolved in ethyl acetate (250 ml) and washed with 10% aqueous potassium carbonate (200 mL). The organic layer was separated, and the aqueous layer was extracted with ethyl acetate (3×150 mL). The combined organic layers were dried over sodium sulfate and concentrated under reduced pressure. The residue was purified by column chromatography (silica, 0% to 50% hexanes/ethyl acetate) to afford a 91% yield (15.0 g) of 116b as a colorless oil: $^1$H NMR (300 MHz, CDCl$_3$) δ 7.38 (d, 1H, J=5.0 Hz), 6.91 (d, 1H, J=5.1 Hz), 3.86 (s, 3H), 2.56 (s, 3H); MS (ESI+) m/z 156.0 (M+H).

Example 116c

Methyl 3-(Bromomethyl)thiophene-2-carboxylate 116c

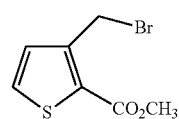

2f

A 1-L single-neck round-bottomed flask equipped with a magnetic stirrer, reflux condenser and nitrogen inlet was purged with nitrogen and charged with 116b (5.00 g, 32.0 mmol), N-bromosuccinimide (5.70 g, 32.0 mmol) and carbon tetra-chloride (300 mL). The solution was heated to 70° C. (oil bath temperature), and 2,2'-azobisisobutyronitrile (526 mg, 3.20 mmol) was added. The resulting mixture was refluxed for 3 h. After that time, the mixture was cooled to room temperature and filtered. The filter cake was washed with carbon tetrachloride (2×50 mL). The filtrate was diluted with ethyl acetate (300 mL) and washed with water (40 mL), saturated aqueous sodium bicarbonate (40 mL) and brine (40 mL). The organic layer was dried over sodium sulfate and concentrated under reduced pressure to afford a quantitative yield (7.50 g) of 116c as a colorless oil: $^1$H NMR (300 MHz, CDCl$_3$) δ 7.39 (d, 1H, J=5.0 Hz), 7.11 (d, 1H, J=5.1 Hz), 4.85 (s, 2H), 3.83 (s, 3H).

Example 116d

Methyl 3-(Aminomethyl)thiophene-2-carboxylate 116d

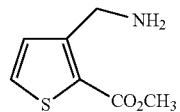

2g

A 2-L single-neck round-bottomed flask equipped with a magnetic stirrer and nitrogen inlet was purged with nitrogen and charged with 116c (7.50 g, 32.0 mmol) and a 7 M solution of ammonia in methanol (915 mL, 6.40 mol). The solution was stirred at room temperature for 14 h. After that time, the reaction mixture was concentrated under reduced pressure. The residue was dissolved in water (150 mL) and extracted with methyl tert-butyl ether (2×25 mL). The aqueous layer was basified with sodium hydroxide (5.00 g) and extracted with methyl tert-butyl ether (3×150 mL). The combined organic layers were dried over sodium sulfate and concentrated under reduced pressure to afford a 57% yield (3.14 g) of 116d as a colorless oil: $^1$H NMR (300 MHz, CDCl$_3$) δ 7.45 (d, 1H, J=5.1 Hz), 7.14 (d, 1H, J=5.1 Hz), 4.11 (s, 2H), 3.88 (s, 3H), 1.72 (br s, 2H); MS (ESI+) m/z 172.0 (M+H). The material was used without further purification.

Example 116e

4H-Thieno[2,3-c]pyrrol-6(5H)-one 116e

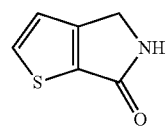

2h

A 250-mL single-neck round-bottomed flask equipped with a magnetic stirrer was purged with nitrogen and charged with 116d (5.00 g, 29.2 mmol) and THF (150 mL). Bis(trimethylaluminum)-1,4-diazabicyclo[2.2.2]octane complex (10.0 g, 39.1 mmol) was added portionwise. The mixture was heated at 60° C. for 14 h. After this time, the mixture was cooled to 0° C. 4 M hydrochloric acid (60 mL) was added dropwise, and the mixture was filtered. The organic layer was separated, and the aqueous layer was extracted with a 20% (v/v) solution of methanol in methylene chloride (3×150 mL). The filter cake was washed with a 20% (v/v) solution of methanol in methylene chloride (3×150 mL). The combined organic layers were dried over sodium sulfate and concentrated under reduced pressure. The residue was purified by column chromatography (silica, 0% to 10% methanol/methylene chloride) to afford a 45% yield (1.87 g) of 116e as an off-white solid: mp 104-105° C.; $^1$H NMR (300 MHz, CDCl$_3$) δ 7.08 (s, 1H), 6.42 (br s, 1H), 4.37 (s, 2H); MS (ESI+) m/z 140.0 (M+H).

Example 116f

2-Bromo-4H-thieno[2,3-c]pyrrol-6(5H)-one 116f

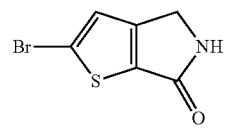

2k

A 250-mL single-neck round-bottomed flask equipped with a magnetic stirrer was purged with nitrogen and charged with 116e (1.87 g, 13.5 mmol), methylene chloride (10 mL), acetic acid (30 mL). The mixture was cooled to 0° C. Bromine (2.30 g, 14.8 mmol) was added dropwise. After the addition was complete, the mixture was stirred for 3 h at 0° C. and then at room temperature for 48 h. After that time, the mixture was partitioned between aqueous saturated sodium bicarbonate (100 mL) and a 20% (v/v) solution of methanol in methylene chloride (100 mL). The layers were separated, and the aqueous layer was extracted with a 20% (v/v) solution of methanol in methylene chloride (3×100 mL). The combined organic layers were dried over sodium sulfate and concentrated under reduced pressure. The residue was purified by column chromatography (silica, 0% to 10% methanol/methylene chloride) to afford a 34% yield (1.01 g) of 116f as an off-white solid: mp 96-97° C.; $^1$H NMR (300 MHz, CDCl$_3$) δ 7.09 (s, 1H), 6.57 (br s, 1H), 4.37 (s, 2H); MS (ESI+) m/z 217.9 (M+H).

Example 116g

2-Cyclopropyl-4H-thieno[2,3-c]pyrrol-6(5H)-one 116g

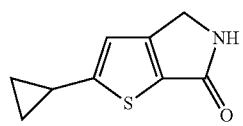

2j

A 100-mL single-neck round-bottomed flask equipped with a reflux condenser, magnetic stirrer and nitrogen inlet was charged with 116f (900 mg, 4.12 mmol), potassium cyclopropyltrifluoroborate (733 mg, 4.95 mmol), cesium carbonate (4.03 g, 12.4 mmol), toluene (18 mL), water (1 mL). After bubbling nitrogen through the resulting suspension for 30 min, palladium(II) acetate (279 mg, 0.412 mmol) and n-butyldi-1-adamantylphosphine (222 mg, 0.618 mmol) were added, and the reaction mixture was heated at 100° C. for 14 h. After this time, the mixture was cooled to room temperature and diluted with ethyl acetate (150 mL) and water (30 mL). The organic layer was separated, and the aqueous layer was extracted with ethyl acetate (3×150 mL). The combined organic layers were dried over sodium sulfate and concentrated under reduced pressure. The residue was purified by column chromatography (silica, 0% to 5% methanol/methylene chloride) to afford a 35% yield (254 mg) of 116g as an off-white solid: mp 109-110° C.; $^1$H NMR (300 MHz, CDCl$_3$) δ 6.72 (s, 1H), 6.08 (br s, 1H), 4.28 (s, 2H), 2.16 (m, 1H), 1.09 (m, 2H), 0.84 (m, 1H); MS (ESI+) m/z 180.1 (M+H).

Example 116h

2-Bromo-6-(2-cyclopropyl-6-oxo-4H-thieno[2,3-c]pyrrol-5(6H)-yl)benzyl Acetate 116h

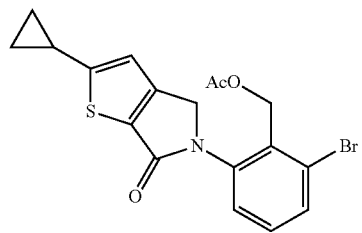

A 100-mL single-neck round-bottomed flask equipped with a reflux condenser, magnetic stirrer and nitrogen inlet was charged with 116h (254 mg, 1.42 mmol), 2l (1.75 g, 2.84 mmol), cesium carbonate (1.16 g, 3.55 mmol), N,N'-dimethylethylenediamine (187 mg, 4.59 mmol) and 1,4-dioxane (10 mL). After bubbling nitrogen through the resulting suspension for 30 min, copper(I) iodide (135 mg, 0.710 mmol) was added, and the reaction mixture was heated at 105° C. (oil bath temperature) for 14 h. After this time, the mixture was cooled to room temperature and filtered. The filtrate was diluted with ethyl acetate (100 mL) and water (20 mL). The organic layer was separated, and the aqueous layer was extracted with ethyl acetate (3×50 mL). The combined organic layers were dried over sodium sulfate and concentrated under reduced pressure. The residue was purified by column chromatography to afford a 22% yield (124 mg) of 116h as a colorless oil: $^1$H NMR (300 MHz, CDCl$_3$) δ 7.62 (m, 1H), 7.27 (m, 2H), 6.77 (s, 1H), 5.21 (s, 2H), 4.62 (s, 2H), 2.18 (m, 1H), 2.00 (s, 3H), 1.12 (m, 2H), 0.85 (m, 2H); MS (ESI+) m/z 406.0 (M+H).

Example 116

2-Cyclopropyl-5-(2-(hydroxymethyl)-3-(1-methyl-6-oxo-5-(pyrimidin-4-ylamino)-1,6-dihydropyridin-3-yl)phenyl)-4H-thieno[3,2-c]pyrrol-6(5H)-one 116

A 50-mL three-neck round-bottomed flask equipped with a reflux condenser, magnetic stirrer and nitrogen inlet was charged with 116h (124 mg, 0.300 mmol), 116a (100 mg, 0.300 mmol), sodium carbonate (95 mg, 0.900 mmol), DMF (2.5 mL), water (1.2 mL) and 1,4-dioxane (4 mL). After bubbling nitrogen through the resulting suspension for 30 min, tetrakis(triphenylphosphine)palladium(0) (35 mg, 0.003 mmol) was added, and the reaction mixture was heated at reflux for 14 h. After this time, the mixture was cooled to room temperature, and methanol (2 mL), water (2 mL) and lithium hydroxide monohydrate (42 mg, 1.00 mmol) were added. The mixture was stirred for 4 h at room temperature and then concentrated in vacuo. The residue was partitioned between ethyl acetate (150 mL) and water (30 mL). The organic layer was separated, and the aqueous layer was extracted with a 20% (v/v) solution of methanol in methylene chloride (3×150 mL). The combined organic layers were dried over sodium sulfate and concentrated under reduced pressure. The residue was purified by column chromatography (silica, 0% to 10% methanol/methylene chloride) to afford a 22% yield (32 mg) of 116 as an off-white solid: mp 140-141° C.; $^1$H NMR (500 MHz, DMSO-d$_6$) δ 9.17 (s, 1H), 8.70 (d, 1H, J=1.1 Hz), 8.64 (s, 1H), 8.29 (d, 1H, J=5.8 Hz), 7.52 (d, 1H, J=2.5 Hz), 7.48 (m, 1H), 7.43 (m, 1H), 7.38 (m, 1H), 7.31 (dd, 1H, J=5.9, 1.1 Hz), 7.04 (s, 1H), 4.91 (t, 1H, J=5.0 Hz), 4.83 (s, 2H), 4.34 (d, 2H, J=5.0 Hz), 3.60 (s, 3H), 2.29 (m, 1H), 1.12 (m, 2H), 0.82 (m, 2H); MS (ESI+) m/z 486.2 (M+H).

Example 117

Example 117a tert-Butyl 3-(6-Chloropyridin-3-yl)azetidine-1-carboxylate 117a

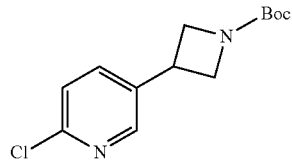

A 250-mL round-bottomed flask equipped with a magnetic stirrer and reflux condenser was charged with zinc (2.54 g, 38.9 mmol), DMF (32 mL), and dibromomethane (736 mg, 4.24 mmol). After stirring at 70° C. for 10 min, the reaction mixture was cooled to room temperature, and chlorotrimethylsilane (423 mg, 3.89 mmol) was added. The resulting mixture was stirred at room temperature for 30 min, and a solution of 1-(tert-butoxycarbonyl)-3-iodoazetidine (9.31 g, 38.9 mmol) in DMF (32 mL) was added. After stirring at 40° C. for 1 h, a solution of 2-chloro-4-iodo-pyridine (10.0 g, 35.3 mmol) in DMF (16 mL) was added, followed by a solution of (dibenzylideneacetone)dipalladium(0) (1.62 g, 1.77 mmol) and tri(2-furyl)-phosphine (820 mg, 3.53 mmol) in DMF (16 mL). After stirring at 70° C. for 16, the reaction mixture was partitioned between saturated aqueous ammonium chloride (200 mL) and diethyl ether (200 mL). The layers were separated, and the aqueous phase was extracted with diethyl ether (200 mL). The organic extracts were combined, dried over sodium sulfate and filtered. The filtrate was concentrated under reduced pressure. The resulting residue was purified by column chromatography to afford a 54% yield (5.42 g) of 117a as a yellow oil: $^1$H NMR (500 MHz, CDCl$_3$) δ 8.29 (d, 1H, J=2.5 Hz), 7.70 (dd, 1H, J=8.5, 2.5 Hz), 7.35 (d, 1H, J=8.5

Hz), 4.37 (t, 2H, J=8.5 Hz), 3.91 (dd, 2H, J=8.5, 4.5 Hz), 3.73 (m, 1H), 1.46 (s, 9H); MS (ESI+) m/z 269.0 (M+H).

Example 117b tert-Butyl 3-(6-(Diphenylmethyleneamino)pyridin-3-yl)azetidine-1-carboxylate 117b

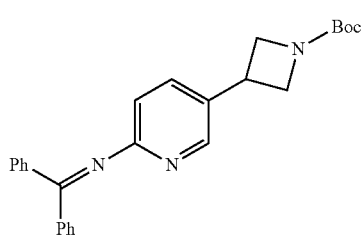

A 500-mL round-bottomed flask equipped with a magnetic stirrer and reflux condenser was charged with 117a (2.00 g, 7.46 mmol), benzophenoneimine (1.62 g, 8.96 mmol), sodium tert-butoxide (1.00 g, 10.4 mmol), (dibenzylideneacetone)-dipalladium(0) (340 mg, 0.373 mmol) and rac-2,2'-bis(diphenylphosphino)-1,1'-binapthyl (700 mg, 1.12 mmol), and the reaction was heated at 100° C. for 3 h. After this time the reaction was cooled to room temperature and concentrated under reduced pressure. The resulting oil was purified by column chromatography to afford a 79% yield (2.44 g) of 117b as a brown solid: mp 104-105° C.; $^1$H NMR (500 MHz, CDCl$_3$) δ 8.20 (d, 1H, J=2.0 Hz), 7.85 (br s, 2H), 7.52 (br s, 1H), 7.44 (br s, 2H), 7.47 (dd, 1H, J=8.5, 2.0 Hz), 7.17 (br s, 5H), 6.61 (d, 1H, J=8.5 Hz), 4.30 (t, 2H, J=8.5 Hz), 3.86 (dd, 2H, J=8.5, 4.5 Hz), 3.62 (m, 1H), 1.45 (s, 9H); MS (ESI+) m/z 413.8 (M+H).

Example 117c tert-Butyl 3-(6-Aminopyridin-3-yl)azetidine-1-carboxylate 117c

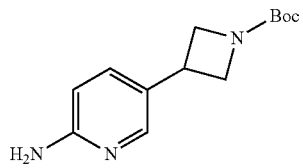

A 250-mL round-bottomed flask equipped with a magnetic stirrer was charged with 117b (2.44 g, 5.91 mmol), methanol (80 mL), 50% hydroxylamine in water (390 mg, 11.8 mmol) and the reaction was stirred at room temperature for 4 h. After this time, the reaction mixture was concentrated, and the resulting residue was purified by column chromatography to afford an 86% yield (1.27 g) of 117c as a yellow solid: mp 103-104° C.; $^1$H NMR (500 MHz, CDCl$_3$) δ 7.94 (d, 1H, J=2.0 Hz), 7.49 (dd, 1H, J=8.5, 2.5 Hz), 6.53 (d, 1H, J=8.5

Hz), 4.48 (br s, 2H), 4.30 (t, 2H, J=8.5 Hz), 3.88 (dd, 2H, J=8.5, 4.5 Hz), 3.62 (m, 1H), 1.44 (s, 9H); MS (ESI+) m/z 249.9 (M+H).

Example 117d tert-Butyl 3-(6-(5-Bromo-1-methyl-2-oxo-1,2-ihydropyridin-3-ylamino)pyridin-3-yl)azetidine-1-carboxylate 117d

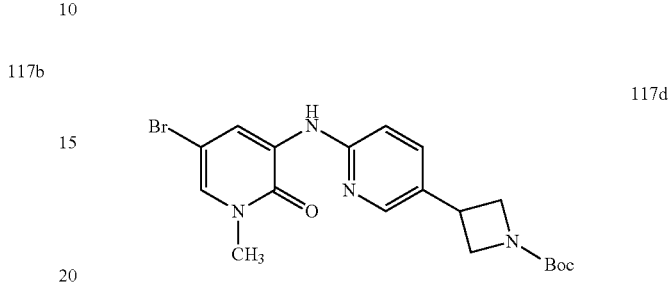

A 250-mL single-neck round-bottomed flask equipped with a magnetic stirrer and reflux condenser was charged with 117c (333 mg, 1.33 mmol), 3,5-dibromo-1-methylpyridin-2(1H)-one (350 mg, 1.33 mmol), cesium carbonate (870 mg, 2.70 mmol) and 1,4-dioxane (10 mL). After bubbling nitrogen through the resulting solution for 30 min, Xantphos (66 mg, 0.114 mmol) and tris(dibenzylidene-acetone)dipalladium(0) (61 mg, 0.066 mmol) were added and the reaction mixture was heated at 105° C. for 3 h. After this time, the mixture was cooled to room temperature and filtered. The filter cake was washed with methylene chloride (2×10 mL), and the combined filtrates were concentrated under reduced pressure. The resulting residue was purified by column chromatography on silica to afford a 79% yield (460 mg) of 117d as a green solid: mp 134-136° C.; $^1$H NMR (500 MHz, DMSO-d$_6$) δ 8.75 (s, 1H), 8.65 (s, 1H), 8.19 (s, 1H), 7.66 (dd, 1H, J=8.5, 2.0 Hz), 7.51 (s, 1H), 7.35 (d, 1H, J=8.5 Hz), 4.21 (t, 2H, J=8.0 Hz), 3.81 (m, 2H), 3.51 (s, 3H), 1.40 (s, 9H); MS (ESI+) m/z 436.1 (M+H).

Example 117e tert-Butyl 3-(6-(5-(3-(5-tert-Butyl-1-oxoisoindolin-2-yl)-2-(hydroxy-methyl)phenyl)-1-methyl-2-oxo-1,2-dihydropyridin-3-ylamino)pyridin-3-yl)azetidine-1-carboxylate 117e

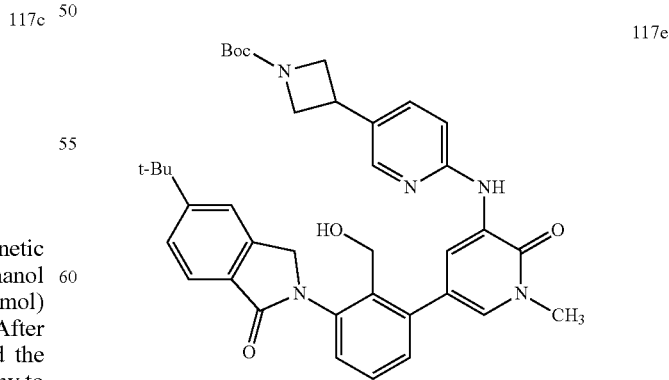

A 100-mL single-neck round-bottomed flask equipped with a magnetic stirrer and nitrogen inlet was charged with 117d (455 mg, 1.04 mmol), 103f (680 mg, 1.50 mmol), sodium carbonate (332 mg, 3.13 mmol), DMF (5 mL), water (2.5 mL) and 1,4-dioxane (8 mL). After bubbling nitrogen through the resulting suspension for 30 min, tetrakis(triphenylphosphine)palladium(0) (121 mg, 0.104 mmol) was added. A reflux condenser was attached to the flask, and the reaction mixture was heated at 120° C. (bath temperature) for 14 h. After this time, the mixture was diluted with 90:10 methylene chloride/methanol (100 mL) and water (75 mL), and the layers were separated. The aqueous layer was extracted with 90:10 methylene chloride/methanol (2×30 mL), and the combined organic layers were washed with brine (100 mL) and dried over sodium sulfate. The drying agent was removed by filtration. The filtrate was concentrated under reduced pressure, and the resulting residue was dissolved in a mixture of THF (5 mL), water (5 mL) and methanol (5 mL). Lithium hydroxide monohydrate (606 mg, 14.4 mmol) was added, and the mixture was stirred at room temperature for 1 h. After this time, the mixture was diluted with 90:10 methylene chloride/methanol (150 mL) and water (100 mL), and the layers were separated. The aqueous layer was extracted with 90:10 methylene chloride/methanol (2×100 mL), and the combined organic layers were washed with brine (100 mL) and dried over sodium sulfate. The drying agent was removed by filtration. The filtrate was concentrated under reduced pressure, and the resulting residue was purified by flash column chromatography to afford 117e in 73% yield (230 mg) as an amorphous yellow solid: mp 151-152° C.; $^1$H NMR (500 MHz, CDCl$_3$) δ 8.69 (s, 1H), 8.12 (s, 1H), 7.92 (s, 1H), 1.90 (d, 1H, J=8.0 Hz), 7.61 (d, 1H, J=8.5 Hz), 7.55-7.46 (m, 5H), 6.86 (d, 1H, J=8.5 Hz), 4.86 (s, 2H), 4.69 (t, 1H, J=6.5 Hz), 4.42 (d, 2H, J=6.5 Hz), 4.30 (t, 2H, J=8.5 Hz), 3.90 (t, 2H, J=8.5 Hz), 3.71 (s, 3H), 3.48 (s, 3H), 1.46 (s, 9H), 1.41 (s, 9H); MS (ESI+) m/z 650.2 (M+H).

Example 117

2-(3-(5-(5-(Azetidin-3-yl)pyridin-2-ylamino)-1-methyl-6-oxo-1,6-dihydropyridin-3-yl)-2-(hydroxymethyl)phenyl)-5-tert-butylisoindolin-1-one 117

A 100-mL single-neck round-bottomed flask equipped with a magnetic stirrer was charged with 117e (495 mg, 0.761 mmol), methylene chloride (3 mL) and trifluoroacetic acid (3 mL), and the mixture was stirred at room temperature for 3 h. After this time, the reaction mixture was concentrated, and the resulting residue was partitioned between 10% aqueous potassium carbonate (10 mL) and methylene chloride (20 mL). The layers were separated, and the aqueous phase was extracted with methylene chloride (20 mL). The organic extracts were combined, dried over sodium sulfate and filtered, and the solvent was removed under reduced pressure. The resulting residue was purified by column chromatography to afford a 25% yield (104 mg) of 117 as a white solid: mp 185-186° C.; $^1$H NMR (500 MHz, DMSO-d$_6$) δ 8.66 (s, 1H), 8.54 (s, 1H), 8.10 (s, 1H), 7.71 (d, 2H, J=8.5 Hz), 7.66 (d, 1H, J=8.5 Hz), 7.61 (d, 1H, J=8.0 Hz), 7.49 (t, 1H, J=8.0 Hz), 7.44 (d, 1H, J=6.5 Hz), 7.37 (m, 2H), 7.28 (d, 1H, J=8.5 Hz), 4.94 (s, 2H), 4.88 (t, 1H, J=4.5 Hz), 4.34 (d, 2H, J=4.5 Hz), 3.71 (m, 3H), 3.59 (s, 3H), 3.54 (m, 2H), 1.33 (s, 9H); MS (ESI+) m/z 550.2 (M+H).

Example 118

Example 118

5-tert-Butyl-2-(2-(hydroxymethyl)-3-(1-methyl-5-(5-(1-methylazetidin-3-yl)pyridin-2-ylamino)-6-oxo-1,6-dihydropyridin-3-yl)phenyl)isoindolin-1-one 118

A 150-mL single-neck round-bottomed flask equipped with a magnetic stirrer was purged with nitrogen, charged with 117 (72 mg, 0.130 mmol), 37% solution of formaldehyde in water (5 mg, 0.170 mmol) and anhydrous methanol (5 mL). A suspension of sodium cyanoborohydride (25 mg, 0.400 mmol) and anhydrous zinc chloride (27 mg, 0.200 mmol) in anhydrous methanol (2.5 mL) was added, and the reaction was stirred at room temperature for 5 h. After this time, the reaction mixture was concentrated, and 10% aqueous potassium carbonate (5 mL) was added. The resulting suspension was filtered, and the filter cake was washed with water (2 mL). The filter cake was purified by column chromatography to afford a 64% yield (56 mg) of 118 as a white solid: mp 201-202° C.; $^1$H NMR (500 MHz, DMSO-d$_6$) δ 8.66 (s, 1H), 8.54 (s, 1H), 8.11 (s, 1H), 7.72 (d, 2H, J=8.5 Hz), 7.64 (m, 2H), 7.49 (t, 1H, J=8.0 Hz), 7.44 (d, 1H, J=6.5 Hz), 7.37 (m, 2H), 7.27 (d, 1H, J=8.5 Hz), 4.94 (s, 2H), 4.88 (t, 1H, J=4.5 Hz), 4.34 (d, 2H, J=4.5 Hz), 3.59 (s, 3H), 3.54 (t, 2H, J=7.0 Hz), 3.45 (m, 1H), 3.01 (t, 2H, J=6.5 Hz), 2.24 (s, 3H), 1.36 (s, 9H); MS (ESI+) m/z 564.3 (M+H).

Example 119

Example 119a 1-(2-(tert-Butyldimethylsilyloxy)ethyl)-3-nitro-1H-pyrazole 119a

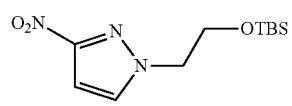

119a

A 100-mL single-neck round-bottomed flask equipped with a reflux condenser and magnetic stirrer was purged with nitrogen and charged with 3-nitro-1H-pyrazole (500 mg, 4.42 mmol), 2-(tert-butyldimethylsilyloxy)-1-bromoethane (2.12 g, 8.85 mmol), cesium carbonate (5.76 g, 17.7 mmol) and anhydrous DMF (5 mL). After heating at 70° C. for 1 h, the mixture was cooled to room temperature and diluted with methylene chloride (50 mL) and water (30 mL). The organic layer was separated, and the aqueous layer was extracted with methylene chloride (2×30 mL). The combined organic layers were dried over sodium sulfate and concentrated under reduced pressure. The residue was purified by column chromatography to afford an 85% yield (1.02 g) of 119a as a white solid: mp 76-77° C.; $^1$H NMR (500 MHz, CDCl$_3$) δ 7.52 (d, 1H, J=2.5 Hz), 6.87 (d, 1H, J=2.5 Hz), 4.29 (t, 2H, J=5.0 Hz), 3.98 (t, 2H, J=5.0 Hz), 0.84 (s, 9H), −0.44 (s, 6H).

Example 119b 1-(2-(tert-Butyldimethylsilyloxy)ethyl)-1H-pyrazol-3-amine 119b

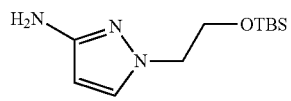

A 250-mL Parr reactor bottle was purged with nitrogen and charged with 10% palladium on carbon (50% wet, 150 mg dry weight) and a solution of 119a (1.02 g, 3.76 mmol) in ethanol (20 mL). The bottle was attached to a Parr hydrogenator, evacuated, charged with hydrogen gas to a pressure of 50 psi and shaken for 3 h. After this time, the hydrogen was evacuated, and nitrogen was charged into the bottle. Celite 521 (1.00 g) was added, and the mixture was filtered through a pad of Celite 521. The filter cake was washed with ethanol (2×25 mL), and the combined filtrates were concentrated to dryness under reduced pressure to afford a 100% yield (928 mg) of 119b as a white solid: mp 54-55° C.; $^1$H NMR (500 MHz, CDCl$_3$) δ 7.25 (d, 1H, J=2.0 Hz), 5.36 (d, 1H, J=2.0 Hz), 4.54 (br s, 2H), 3.90 (t, 2H, J=5.5 Hz), 3.81 (t, 2H, J=5.5 Hz), 0.84 (s, 9H), −0.35 (s, 6H). MS (APCI+) m/z 242.6 (M+H).

Example 119c

5-Bromo-3-(1-(2-(tert-butyldimethylsilyloxy)ethyl)-1H-pyrazol-3-ylamino)-1-methylpyridin-2(1H)-one 119c

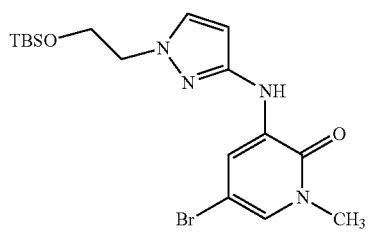

Using the same general procedure as described for the preparation of 103l, reaction of 119b (400 mg, 1.66 mmol) with 3,5-dibromo-1-methylpyridin-2(1H)-one (441 mg, 1.66 mmol) gave a 76% yield (521 mg) of 119c as a yellow solid: mp 96-97° C.; $^1$H NMR (500 MHz, CDCl$_3$) δ 7.85 (d, 1H, J=2.5 Hz), 7.42 (s, 1H), 5.31 (d, 1H, J=2.5 Hz), 6.87 (d, 1H, J=2.5 Hz), 5.84 (d, 1H, J=2.5 Hz), 4.16 (t, 2H, J=5.0 Hz), 3.96 (t, 2H, J=5.5 Hz), 3.58 (s, 3H), 0.85 (s, 9H), −0.04 (s, 6H). MS (APCI+) m/z 427.4 (M+H).

Example 119

2-(3-(6-(1-(2-Hydroxyethyl)-1H-pyrazol-4-ylamino)-4-methyl-5-oxo-4,5-dihydropyrazin-2-yl)-2-(hydroxymethyl)phenyl)-3,4,5,6,7,8-hexahydrobenzothieno[2,3-c]pyridin-1(2H)-one 119

Using the same general procedure as described for the preparation of 114, reaction of 119c (200 mg, 0.469 mmol) with 103f (261 mg, 0.563 mmol) gave a 34% yield (83 mg) of 119 as an off-white solid: mp 198-199° C.; $^1$H NMR (500 MHz, DMSO-d$_6$) δ 8.07 (s, 1H), 8.00 (d, 1H, J=2.5 Hz), 7.73-7.71 (m, 2H), 7.61 (dd, 1H, J=8.0, 1.5 Hz), 7.50-7.47 (m, 2H), 7.42 (dd, 1H, J=8.0, 1.5 Hz), 7.37 (dd, 1H, J=8.0, 1.5 Hz), 7.24 (d, 1H, J=2.5 Hz), 6.06 (d, 1H, J=2.5 Hz), 4.94 (s, 2H), 4.89 (t, 1H, J=5.0 Hz), 4.78 (t, 1H, J=5.0 Hz), 4.35 (d, 2H, J=9.5 Hz), 3.99 (t, 2H, J=5.5 Hz), 3.67 (q, 2H, J=5.5 Hz), 3.58 (s, 3H), 1.37 (s, 9H); MS (ESI+) m/z 528.3 (M+H).

Example 120

Example 120a 1-(6-Nitropyridin-3-yl)azetidin-3-ol 120a

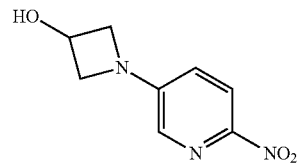

A 500-mL single-neck round-bottomed flask equipped with a magnetic stirrer and reflux condenser was purged with nitrogen and charged with 2-nitro-5-bromopyridine (3.00 g, 14.8 mmol), 3-hydroxyazetidine hrdrochloride (2.91 g, 26.56 mmol), N,N-diisopropylethyl amine (5.67 g, 43.91 mmol) and tetrabutylammonium iodide (8.17 g, 22.1 mmol) and N,N-dimethylacetamide (15 mL). This mixture was heated at 120° C. (bath temperature) for 14 h. After this time, the reaction mixture was cooled to room temperature, diluted with water (100 mL) and extracted with ethyl acetate (4×100 mL). The combined organic layers were washed with brine (250 mL) and dried over sodium sulfate. The drying agent was removed by filtration, and the filtrate was concentrated under reduced pressure. The resulting residue was purified using a silica gel column, eluting the desired product with 80% ethyl acetate in hexanes to afford a 49% yield (1.43 g) of 120a as a yellow semi-solid: $^1$H NMR (500 MHz, DMSO-d$_6$) δ 8.13 (d, 1H, J=9.0 Hz), 7.70 (d, 1H, J=2.5 Hz), 6.91 (m, 1H), 5.83 (d, 1H, J=6.0 Hz), 4.65 (m, 1H), 4.31 (m, 2H), 3.83 (m, 2H); MS (ESI+) m/z 196.2 (M+H).

Example 120b 1-(6-Aminopyridin-3-yl)azetidin-3-ol 120b

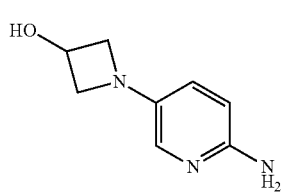

Using the same general procedure for the preparation of 119b, reduction of 120a (1.43 g, 7.32 mmol) gave a 95% yield (1.15 g) of 120b as a yellow semi-solid: $^1$H NMR (500 MHz, DMSO-d$_6$) δ 7.22 (d, 1H, J=2.5 Hz), 6.69 (m, 1H), 6.35 (d, 1H, J=8.0 Hz), 5.16 (s, 1H), 4.48 (m, 1H), 3.96 (m, 2H), 3.34 (m, 2H); MS (ESI+) m/z 166.2 (M+H).

Example 120c

5-Bromo-3-(5-(3-hydroxyazetidin-1-yl)pyridin-2-ylamino)-1-methylpyridin-2(1H)-one 120c

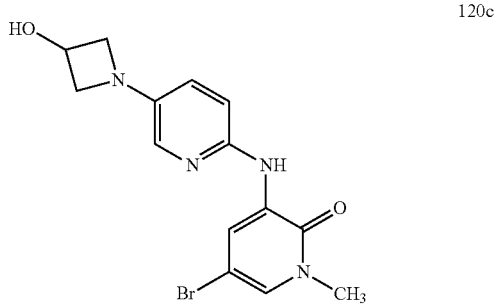 [SMILES: Cn1cc(Br)cc(Nc2ccc(N3CC(O)C3)cn2)c1=O]

120c

A 100-mL three-neck round-bottomed flask equipped with a reflux condenser, magnetic stirrer and nitrogen inlet was charged with 120b (270 mg, 1.64 mmol), 3,5-dibromo-1-methylpyridin-2(1H)-one (435 mg, 1.64 mmol), cesium carbonate (1.18 g, 3.61 mmol), and 1,4-dioxane (20 mL). After bubbling nitrogen through the resulting suspension for 30 min, Xantphos (142 mg, 0.246 mmol) and tris(dibenzylideneacetone)dipalladium(0) (150 mg, 0.164 mmol) were added, and the reaction mixture was heated at reflux for 3 h. After this time, the mixture was cooled to room temperature and filtered, and the filter cake was washed with methylene chloride (2×20 mL). The filtrates were combined and concentrated under reduced pressure, and the resulting residue was purified by column chromatography to afford a 40% yield (217 mg) of 120c as a yellow solid: 210° C. dec; $^1$H NMR (500 MHz, DMSO-d$_6$) δ 8.50 (d, 1H, J=4.0 Hz), 8.44 (s, 1H), 7.54 (d, 1H, J=5.0 Hz), 7.42 (d, 1H, J=5.0 Hz), 7.20 (d, 1H, J=14.5 Hz), 6.89 (dd, 1H, J=14.5, 4.0 Hz), 5.59 (d, 1H, J=11.0 Hz), 4.54 (m, 1H), 4.05 (dd, 2H, J=13.0, 11.0 Hz), 3.50-3.44 (m, 5H); MS (APCI+) m/z 351.6 (M+H).

Example 120

5-tert-Butyl-2-(3-(5-(5-(3-hydroxyazetidin-1-yl)pyridin-2-ylamino)-1-methyl-6-oxo-1,6-dihydropyridin-3-yl)-2-(hydroxymethyl)phenyl)isoindolin-1-one 120

A 100-mL single-neck round-bottomed flask equipped with a magnetic stirrer and reflux condenser was purged with nitrogen and charged with 120c (215 mg, 0.613 mmol), 103f (340 mg, 0.735 mmol), sodium carbonate (195 mg, 1.84 mmol), 1,4-dioxane (8 mL) and water (2 mL). This mixture was degassed with nitrogen for 30 min. Tetrakis(triphenylphosphine)palladium (71 mg, 0.061 mmol) was added. After heating at 100° C. for 3 h, the reaction mixture was cooled to room temperature and partitioned between water (40 mL) and methylene chloride (100 mL). The layers were separated, and the aqueous phase was extracted with methylene chloride (2×50 mL). The organic extracts were combined, dried over sodium sulfate, filtered and concentrated under reduced pressure. The resulting residue was dissolved in methanol (5 mL), and potassium carbonate (500 mg, 3.62 mmol) was added. After stirring at room temperature for 2 h, the reaction mixture was partitioned between water (20 mL) and methylene chloride (20 mL). The layers were separated, and the aqueous phase was extracted with methylene chloride (2×20 mL). The organic extracts were combined, dried over sodium sulfate, filtered and concentrated under reduced pressure. The resulting residue was purified by flash chromatography to afford 120 in 21% yield (72 mg) as an off-white solid: >250° C.; $^1$H NMR (500 MHz, DMSO-d$_6$) δ 8.48 (s, 1H), 8.25 (d, 1H, J=2.0 Hz), 7.73-7.71 (m, 2H), 7.62 (d, 1H, J=8.5 Hz), 7.51-7.42 (m, 3H), 7.36 (d, 1H, J=7.5 Hz), 7.28 (d, 1H, J=2.0 Hz), 7.17 (d, 1H, J=9.0 Hz), 6.87 (dd, 1H, J=9.0, 3.0 Hz), 5.56 (d, 1H, J=6.5 Hz), 4.94 (s, 2H), 4.88 (t, 1H, J=5.0 Hz), 4.54 (m, 1H), 4.33 (d, 2H, J=5.0 Hz), 4.02 (t, 2H, J=7.0 Hz), 3.58 (s, 3H), 3.43 (t, 2H, J=7.0 Hz), 1.36 (s, 9H); MS (ESI+) m/z 566.3 (M+H).

Example 121

Example 121a tert-Butyl 4-(6-Nitropyridin-3-yl)-3-oxopiperazine-1-carboxylate 121a

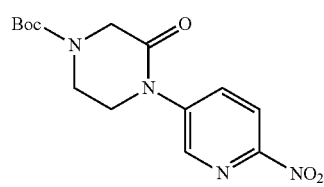

121a

A 250-mL single-neck round-bottomed flask equipped with a magnetic stirrer and reflux condenser was charged with 2-nitro-5-bromopyridine (1.00 g, 5.00 mmol), 2-oxo-4-(tert-butoxycarbonyl)piperazine (1.01 g, 5.00 mmol), cesium carbonate (3.58 g, 11.0 mmol) and 1,4-dioxane (40 mL). After bubbling nitrogen through the resulting solution for 30 min, Xantphos (246 mg, 0.425 mmol) and tris(dibenzylidene-acetone)dipalladium(0) (230 mg, 0.250 mmol) were added, and the reaction mixture was heated at reflux for 6 h. Water (30 mL) and ethyl acetate (150 mL) were added after the reaction mixture was cooled to room temperature. The resulting mixture was filtered through a bed of Celite 521. The organic layer of the filtrate was separated and the aqueous layer was extracted with ethyl acetate (2×50 mL). The combined organic layers were washed with brine (30 mL), dried over sodium sulfate and purified by column chromatography to afford a 96% yield (1.55 g) of 121a as an amber oil: $^1$H NMR (300 MHz, CDCl$_3$) δ 8.67 (d, 1H, J=2.4 Hz), 8.32 (d, 1H, J=8.7 Hz), 8.15 (dd, 1H, J=8.7, 2.4 Hz), 4.33 (s, 1H), 3.89 (m, 4H), 1.48 (s, 9H); MS (ESI+) m/z 323.1 (M+H).

Example 121b tert-Butyl 4-(6-aminopyridin-3-yl)-3-oxopiperazine-1-carboxylate 121b

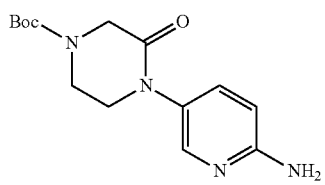

121b

A 250-mL Parr reactor bottle was purged with nitrogen and charged with 10% palladium on carbon (50% wet, 100 mg dry weight) and a solution of 121a (500 mg, 1.55 mmol) in ethanol (20 mL). The bottle was attached to Parr hydrogenator, evacuated, charged with hydrogen gas to a pressure of 45 psi and shaken for 4 h. After this time, the hydrogen was evacuated, and nitrogen was charged into the bottle. Celite 521 (1.0 g) was added, and the mixture was filtered through a pad of Celite 521. The filter cake was washed with ethanol (2×30 mL), and the filtrate was concentrated under reduced pressure to afford a 95% yield of 121b (430 mg) as an amber film: $^1$H NMR (500 MHz, CDCl$_3$) δ 7.98 (d, 1H, J=2.5 Hz), 7.38 (dd, 1H, J=8.5, 2.0 Hz), 6.52 (d, 1H, J=8.5 Hz), 4.54 (s, 1H), 4.26 (s, 2H), 3.78 (t, 2H, J=5.5 Hz), 3.67 (t, 2H, J=5.0 Hz), 1.50 (s, 9H); MS (ESI+) m/z 293.1 (M+H).

Example 121c tert-Butyl 4-(6-(5-Bromo-1-methyl-2-oxo-1,2-dihydropyridin-3-ylamino)pyridin-3-yl)-3-oxopiperazine-1-carboxylate 121c

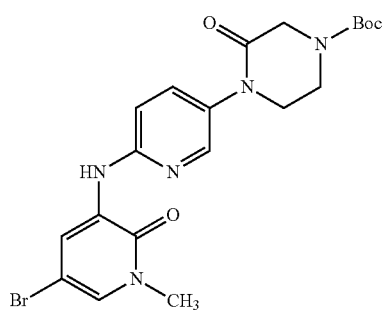

121c

A 100-mL three-neck round-bottomed flask equipped with a magnetic stirrer, nitrogen inlet and reflux condenser was charged with 3,5-dibromo-1-methylpyridin-2(1H)-one (530 mg, 1.99 mmol), 121b (580 mg, 1.99 mmol), cesium carbonate (1.43 g, 4.40 mmol) and 1,4-dioxane (30 mL). After bubbling nitrogen through the resulting mixture for 20 minutes, Xantphos (98.4 mg, 0.170 mmol) and tris(dibenzylideneacetone)dipalladium(0) (91.6 mg, 0.100 mmol) were added, and the reaction mixture was heated at reflux for 4 h. After this time, the reaction was cooled to room temperature, filtered and concentrated under reduced pressure. The resulting residue was purified by flash chromatography to afford an 84% yield (802 mg) of 121c as a yellow solid: mp 130-132° C.; $^1$H NMR (500 MHz, CDCl$_3$) δ 8.68 (d, 1H, J=2.5 Hz), 8.24 (d, 1H, J=2.5 Hz), 7.98 (s, 1H), 7.52 (dd, 1H, J=9.0, 2.5 Hz), 7.00 (d, 1H, J=2.5 Hz), 6.82 (d, 1H, J=8.5 Hz), 4.26 (s, 2H), 3.81 (m, 2H), 3.73 (m, 2H), 3.60 (s, 3H), 1.50 (s, 9H); MS (ESI+) m/z 478.2 (M+H).

Example 121

5-tert-Butyl-2-(2-(hydroxymethyl)-3-(1-methyl-6-oxo-5-(5-(2-oxopiperazin-1-yl)pyridin-2-ylamino)-1,6-dihydropyridin-3-yl)phenyl)isoindolin-1-one 121

A 100-mL three-neck round-bottomed flask equipped with a magnetic stirrer and reflux condenser was charged with 121c (477 mg, 1.00 mmol), 103f (463 mg, 1.00 mmol), sodium carbonate (424 mg, 4.00 mmol), water (4 mL) and 1,4-dioxane (20 mL). After bubbling nitrogen through the resulting suspension for 20 min, tetrakis(triphenylphosphine)-palladium(0) (115 mg, 0.100 mmol) was added, and the reaction mixture was heated at 100° C. for 4 h. After this time, the reaction mixture was cooled to room temperature and filtered, and the filter cake was washed with a 1:10 mixture of methanol and methylene chloride (30 mL). The filtrate was concentrated under reduced pressure to afford a brown residue.

A 50-mL single-neck round-bottomed flask equipped with a magnetic stirrer was purged with nitrogen and charged with the brown residue (prepared above, 1.00 mmol, presuming quantitative yield) and methylene chloride (8 mL). Trifluoroacetic acid (5 mL) was added. The reaction was stirred at room temperature for 2 h. After this time, the reaction mixture was evaporated under reduced pressure. The residue was directly used in the following step.

Another 100-mL single-neck round-bottomed flask equipped with a magnetic stirrer and reflux condenser was charged with residue obtained above, THF (10 mL), ethanol (10 mL), water (10 mL) and lithium hydroxide (96.0 mg, 4.00 mmol). The mixture was stirred at 50° C. for 2 h. After this time, the reaction mixture was concentrated under reduced pressure. The resulting residue was purified by flash chromatography to afford a 15% (80 mg) yield of 121 as a white solid: mp 218-220° C.; $^1$H NMR (500 MHz, DMSO-d$_6$) δ 8.71 (s, 1H), 8.67 (d, 1H, J=2.0 Hz), 8.12 (d, 1H, J=3.0 Hz), 7.71 (m, 2H), 7.60 (dd, 1H, J=8.0, 1.5 Hz), 7.55 (dd, 1H, J=9.0, 2.5 Hz), 7.49 (t, 1H, J=8.0 Hz), 7.43 (dd, 1H, J=8.0, 1.5 Hz), 7.41-7.38 (m, 2H), 7.32 (d, 1H, J=9.0 Hz), 4.94 (s, 2H), 4.89 (t, 1H, J=5.0 Hz), 4.35 (d, 2H, J=5.0 Hz), 3.60 (s, 3H), 3.56 (t, 2H, J=5.5 Hz), 3.37 (s, 2H), 2.99 (t, 2H, J=5.5 Hz), 2.76 (s, 1H), 1.36 (s, 9H); MS (ESI+) m/z 593.3 (M+H).

Example 122

Example 122a

5-Bromo-1-methyl-3-nitropyridin-2(1H)-one 122a

A 1-L round-bottomed flask equipped with a magnetic stirrer was purged with nitrogen and charged with 5-Bromo-3-nitropyridin-2(1H)-one (25.0 g, 114 mmol), anhydrous DMF (500 mL) and potassium carbonate (34.7 g, 251 mmol), and the suspension stirred for 15 min at ambient temperature. After this time, methyl iodide (17.8 g, 126 mmol) was added, and the mixture stirred at room temperature for 16 h. The reaction mixture was then diluted with water (500 mL) and extracted with methylene chloride (3×500 mL). The organic extracts were combined, washed with 10% aqueous lithium chloride (300 mL) and water (300 mL) and dried over sodium sulfate. After removing the drying agent by filtration, the filtrate was evaporated to dryness under reduced pressure. The resulting residue was flash chromatographed eluting with a gradient from 50% to 100% of ethyl acetate in hexanes, and the fractions containing 122a were collected to afford, after concentrating under reduced pressure, an 89% yield (23.6 g) of 122a as a yellow solid: mp 122-123° C.; $^1$H NMR (300 MHz, CDCl$_3$) δ 8.37 (d, 1H, J=2.7 Hz), 7.26 (s, 1H), 3.68 (s, 3H); MS (ESI+) m/z 234 (M+H).

Example 122b

1-Methyl-3-nitro-5-(4,4,5,5-tetramethyl-1,3,2-dioxaborolan-2-yl)pyridin-2(1H)-one 122b

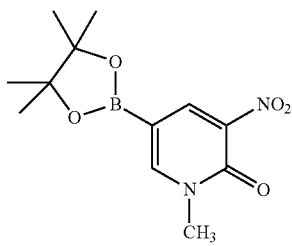

A 3-L three-neck round-bottomed flask equipped with a mechanical stirrer, reflux condenser and thermoregulator was purged with nitrogen and charged with 122a (23.6 g, 102 mmol), 4,4,4',4',5,5,5',5'-octamethyl-2,2'-bi(1,3,2-dioxaborolane) (32.2 g, 127 mmol), potassium acetate (30.0 g, 306 mmol) and 1,4-dioxane (800 mL). A stream of nitrogen was passed through the resulting suspension for 30 min. Pd(dppf)Cl2.CH$_2$Cl$_2$ (4.17 g, 5.10 mmol) was then added, and the reaction was stirred at 80° C. for 2 h. After this time, the mixture was cooled to ambient temperature and evaporated to dryness under reduced pressure at 40° C. The resulting black solid was charged into a 3-L three-neck round-bottomed flask equipped with a mechanical stirrer and reflux condenser. Toluene (640 mL) and magnesium sulfate (20 g) were added, and the resulting suspension was heated under nitrogen to 90° C. over 15 min. The mixture was filtered hot through a pad of Cellpure P65, and the filter cake was washed with hot toluene (3×45 mL). The filtrate was evaporated on a rotary evaporator at 40° C. until a thick suspension formed (weight of the residue was 97 g). This suspension was filtered using the filtrate to transfer the residual material from the walls of the flask. The filter cake was washed with toluene (15 mL) and dried for 2 h under vacuum at 40° C. to afford a 73% yield (20.8 g) of 122b as a yellow solid: $^1$H NMR (300 MHz, DMSO-d$_6$) δ 8.48 (d, 1H, J=2.0 Hz), 8.34 (d, 1H, J=2.0 Hz), 3.60 (s, 3H), 1.30 (s, 12H).

Example 122c 2-(5-tert-Butyl-1-oxoisoindolin-2-yl)-6-(1-methyl-5-nitro-6-oxo-1,6-dihydropyridin-3-yl)benzyl Acetate 122c

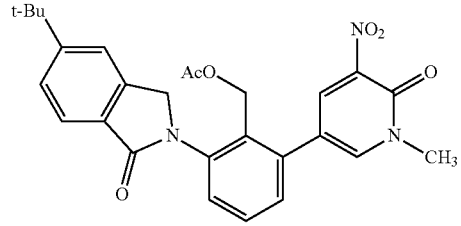

A 100-mL three-neck round-bottomed flask equipped with a magnetic stirrer was purged with nitrogen and charged with 122b (560 mg, 2.00 mmol), 103f (830 mg, 2.00 mmol), sodium carbonate (848 mg, 8.00 mmol), dioxane (30 mL) and water (6 mL). This mixture was degassed with nitrogen for 15 min. Tetrakis(triphenyl-phosphine)palladium (231 mg, 0.200 mmol) was added. After heating at 100° C. for 5 h, the reaction mixture was cooled to room temperature and diluted with ethyl acetate (200 mL). The resulting mixture was washed with saturated aqueous sodium bicarbonate (30 mL) and brine (30 mL), dried over sodium sulfate, filtered and concentrated under reduced pressure. The resulting residue was purified by flash chromatography on silica gel to afford an 81% yield (800 mg) of 122c as a crude product, which was used in next step without further purification.

Example 122d 2-(5-Amino-1-methyl-6-oxo-1,6-dihydropyridin-3-yl)-6-(5-tert-butyl-1-oxoisoindolin-2-yl)benzyl Acetate 122d

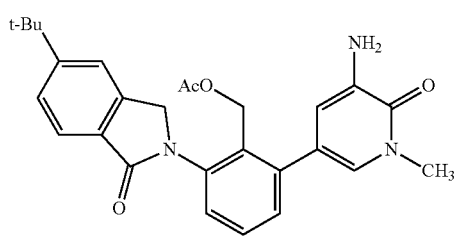

A 50-mL single-neck round-bottomed flask equipped with a magnetic stirrer was purged with nitrogen and charged with 122c (600 mg, 1.23 mmol), acetic acid (10 mL) and THF (5 ml). Zinc dust (1.56 g, 20.5 mmol) was added in portions. The reaction mixture was stirred at room temperature for 1 h. After this time, the reaction mixture was filtered, and the filtrate was evaporated under reduced pressure. The resulting residue was purified by flash chromatography to afford a 81% (460 mg) yield of 122d as a yellow oil: $^1$H NMR (500 MHz, CDCl$_3$) δ 7.85 (d, 1H, J=8.0 Hz), 7.58 (d, 1H, J=8.0 Hz), 7.52 (s, 1H), 7.45 (t, 1H, J=8.0 Hz), 7.28 (d, 2H, J=8.0 Hz), 6.74 (d, 1H, J=2.0 Hz), 6.57 (d, 1H, J=2.0 Hz), 5.08 (s, 2H), 4.78 (s, 2H), 4.37 (s, 2H), 3.60 (s, 3H), 1.85 (s, 3H), 1.40 (s, 9H); MS (ESI+) m/z 460.3 (M+H).

Example 122e

3-Chloro-6-(4-methylpiperazin-1-yl)pyridazine 122e

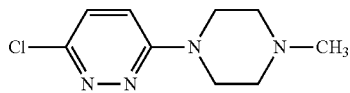

A 25-mL single-neck round bottomed flask equipped with a magnetic stirrer was purged with nitrogen and charged with 3,6-dichloropyridazine (1.49 g, 10.0 mmol) and N-methylpiperazine (1.17 g, 11.7 mmol), and the flask was placed in an oil bath, which was heated to 100° C. After 1.5 h the flask was cooled to room temperature, and the resulting cake was crushed and triturated with acetonitrile (10 mL). The suspension was filtered, and the filter cake was mixed with 10% aqueous potassium carbonate (15 mL). The resulting mixture was extracted with MtBE (2×35 mL). The organic extracts were combined, dried over sodium sulfate and filtered. The filtrate was evaporated under reduced pressure to afford a 60% yield (1.27 g) of 122e as a white solid: mp 106-107° C.; $^1$H NMR (300 MHz, CDCl$_3$) δ 7.20 (d, 1H, J=9.5 Hz), 6.89 (d, 1H, J=9.6 Hz), 3.65 (t, 4H, J=5.1 Hz), 2.53 (t, 4H, J=5.1 Hz), 2.35 (s, 3H); MS (ESI+) m/z 213.1 (M+H).

Example 122

5-tert-Butyl-2-(2-(hydroxymethyl)-3-(1-methyl-5-(6-(4-methylpiperazin-1-yl)pyridazin-3-ylamino)-6-oxo-1,6-dihydropyridin-3-yl)phenyl)isoindolin-1-one 122

A 100-mL three-neck round-bottomed flask equipped with a magnetic stirrer, nitrogen inlet and reflux condenser was charged with 122d (550 mg, 1.19 mmol), 122e (255 mg, 1.19 mmol), cesium carbonate (860 mg, 2.64 mmol) and 1,4-dioxane (20 mL). After bubbling nitrogen through the resulting mixture for 20 minutes, Xantphos (59.0 mg, 0.102 mmol) and tris(dibenzylideneacetone)dipalladium(0) (55.0 mg, 0.06 mmol) were added, and the reaction mixture was heated at reflux for 5 h. After this time, the reaction was cooled to room temperature, filtered and concentrated under reduced pressure to afford a brown residue. Another 100-mL single-neck round-bottomed flask equipped with a magnetic stirrer and reflux condenser was charged with residue obtained above, THF (10 mL), ethanol (10 mL), water (10 mL) and lithium hydroxide (115 mg, 4.80 mmol). The mixture was stirred at 50° C. for 2 h. After this time, the reaction mixture was concentrated under reduced pressure. The resulting residue was purified by flash chromatography to afford a 23% (165 mg) yield of 122 as a white solid: mp 171-172° C.; $^1$H NMR (500 MHz, DMSO-d$_6$) δ 8.66 (d, 1H, J=2.0 Hz), 8.57 (s, 1H), 7.72 (d, 1H, J=8.5 Hz), 7.71 (s, 1H), 7.61 (d, 1H, J=8.0, 1.5 Hz), 7.54 (d, 1H, J=9.5 Hz), 7.50 (t, 1H, J=8.0 Hz), 7.45 (dd, 1H, J=8.0, 1.5 Hz), 7.38-7.36 (m, 2H), 7.30 (d, 1H, J=9.5 Hz), 4.94 (s, 2H), 4.84 (t, 1H, J=5.0 Hz), 4.34 (d, 2H, J=5.0 Hz), 3.60 (s, 3H), 3.41 (t, 4H, J=5.0 Hz), 2.39 (t, 4H, J=5.0 Hz), 2.20 (s, 3H), 1.36 (s, 9H); MS (ESI+) m/z 594.3 (M+H).

Example 123

Example 123a

Methyl 2-Cyano-4-fluorobenzoate 123a

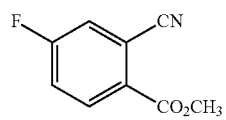

A 100-mL single-neck round-bottomed flask equipped with a magnetic stirrer was purged with nitrogen and charged with methyl 2-chloro-4-fluorobenzoate (10.0 g, 53.0 mmol), copper (I) cyanide (5.22 g, 58.3 mmol) and 2-methylpyrrolidinone (30 mL). After heating at 195° C. for 1.5 h, the reaction mixture was cooled to room temperature and poured into water (600 mL). The resulting suspension was filtered, and the filter cake was washed with water (100 mL). To the solid obtained was then added a solution of sodium cyanide (3.00 g, 61.2 mmol) in water (110 mL), and the reaction mixture was stirred at room temperature for 50 min. After this time, ethyl acetate (500 mL) was added, and the layers were separated. The aqueous phase was extracted with ethyl acetate (2×10 mL), and the organic extracts were combined, dried over sodium sulfate, filtered and concentrated under reduced pressure. The resulting residue was purified by flash chromatography to afford 123a in 73% yield (6.99 g) as a white solid: mp 92-93° C.; ¹H NMR (500 MHz, CDCl₃) δ 8.18 (dd, 1H, J=9.0, 5.5 Hz), 7.50 (dd, 1H, J=8.0, 2.5 Hz), 7.38 (m, 1H), 4.01 (s, 3H).

Example 123b

5-Fluoroisoindolin-1-one 123b

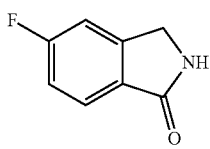
123b

A 250-mL Parr reactor bottle was purged with nitrogen and charged with Raney nickel (4.00 g) and a solution of 123a (2.00 g, 11.2 mmol) in ethanol (20 mL). The bottle was attached to a Parr hydrogenator, evacuated, charged with hydrogen gas to a pressure of 50 psi and shaken for 16 h. After this time, the hydrogen was evacuated, and nitrogen was charged into the bottle. Celite 521 (5.00 g) was added, and the mixture was filtered through a pad of Celite 521. The filter cake was washed with ethanol (2×75 mL), and the combined filtrates were concentrated to dryness under reduced pressure to afford a 76% yield of 123b (1.29 g) as a colorless oil: ¹H NMR (500 MHz, CDCl₃) δ 7.85 (dd, 1H, J=8.5, 5.5 Hz), 7.21-7.16 (m, 2H), 7.05 (br s, 1H), 4.56 (s, 2H).

Example 123c 5-(Dimethylamino)isoindolin-1-one 123c

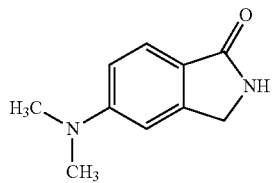
123c

A 500-mL high-pressure bomb reactor was charged with 123b (2.20 g, 14.5 mmol) ethanol (30 mL) and excess dimethylamine (50 mL). The mixture was heated at 165° C. for 36h. After this time, the mixture was concentrated and the resulting residue was purified by flash column chromatography (silica, 98:2 ethyl acetate/triethyl-amine) to afford an 81% yield (2.40 g) of 123c as a yellow solid: mp 122-124° C.;

¹H NMR (300 MHz, DMSO-d₆) δ 7.99 (s, 1H), 7.44 (d, 1H, J=9.3 Hz), 6.77 (m, 2H), 4.24 (s, 2H), 2.99 (s, 6H).

Example 123d

2-Bromo-6-(5-(dimethylamino)-1-oxoisoindolin-2-yl)benzyl Acetate 123d

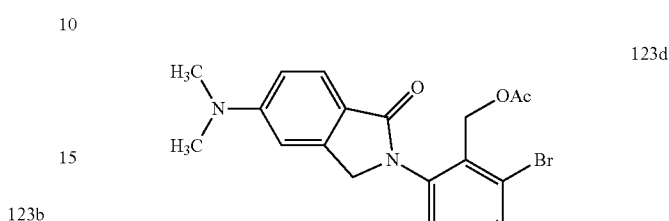
123d

A 100-mL single-neck round-bottomed flask equipped with a magnetic stirrer and nitrogen inlet was charged with 123c (2.40 g, 13.6 mmol), 102d (8.34 g, 27.3 mmol), cesium carbonate (1.34 g, 4.10 mmol), N,N'-dimethylethylenediamine (181 mg, 2.05 mmol) and 1,4-dioxane (12 mL). After bubbling nitrogen through the resulting suspension for 30 min, copper iodide (195 mg, 1.03 mmol) was added. A reflux condenser was attached to the flask, and the reaction mixture was heated at 105° C. for 16 h. After this time, the mixture was cooled to room temperature and filtered. The filtrate was diluted with ethyl acetate (150 mL) and water (75 mL), and the layers were separated. The aqueous layer was extracted with ethyl acetate (2×50 mL), and the combined organic layers were washed with brine (100 mL) and dried over sodium sulfate. The drying agent was removed by filtration. The filtrate was concentrated under reduced pressure, and the resulting residue was purified by flash column chromatography (silica, 70:30 hexanes/ethyl acetate) to afford a 48% yield (2.65 g) of 123d as a white solid: mp 93-95° C.; ¹H NMR (500 MHz, DMSO-d₆) δ 7.75 (d, 1H, J=8.5 Hz), 7.62 (dd, 1H, J=7.5, 1.0 Hz), 7.27 (m, 2H), 6.81 (t, 1H, J=6.5 Hz), 6.68 (s, 1H), 5.21 (s, 2H), 4.69 (s, 2H), 3.09 (s, 6H), 2.00 (s, 3H); (ESI+) m/z 403.6 (M+H).

Example 123e 2-(5-(Dimethylamino)-1-oxoisoindolin-2-yl)-6-(4,4,5,5-tetramethyl-1,3,2-dioxaborolan-2-yl)benzyl Acetate 123e

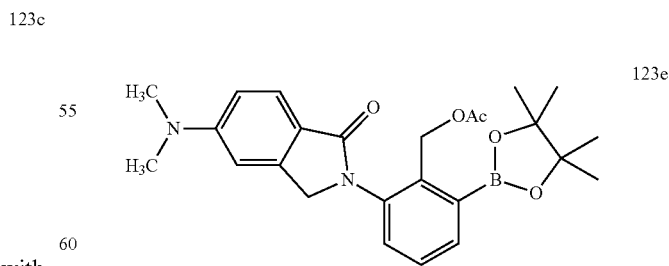
123e

Using the same general procedure as described for the preparation of 102g reaction of 123d (2.65 g, 6.59 mmol) with bis(pinacolato)diboron (5.02 g, 19.8 mmol) gave a 100% yield (3.00 g) of 123e as a brown solid: mp 75-76° C.; ¹H NMR (300 MHz, CDCl₃) δ 7.85 (dd, 1H, J=4.2, 1.8 Hz), 7.76

(d, 1H, J=8.7 Hz), 7.45 (m, 2H), 6.80 (dd, 1H, J=8.7, 2.1 Hz), 6.69 (s, 1H), 5.13 (s, 2H), 4.69 (s, 2H), 3.08 (s, 6H), 1.93 (s, 3H), 1.34 (s, 12H).

Example 123

5-(Dimethylamino)-2-(2-(hydroxymethyl)-3-(1-methyl-5-(5-methyl-4,5,6,7-tetrahydropyrazolo[1,5-a]pyrazin-2-ylamino)-6-oxo-1,6-dihydropyridin-3-yl)phenyl)isoindolin-1-one 123

Using the same general procedure as described for the preparation of 103 reaction of 123e (450 mg, 1.00 mmol) with 103l (260 mg, 0.800 mmol) followed by a hydrolysis gave a 24% yield (130 mg) of 123 as a white solid: mp 148-150° C.; $^1$H NMR (500 MHz, DMSO-$d_6$) δ 8.09 (s, 1H), 7.98 (d, 1H, J=2.0 Hz), 7.56 (d, 1H, J=8.0 Hz), 7.47 (t, 1H, J=8.0 Hz), 7.39 (dd, 1H, J=8.0, 1.5 Hz), 7.33 (dd, 1H, J=8.0, 1.5 Hz), 7.24 (d, 1H, J=2.0 Hz), 6.88-6.85 (m, 2H), 5.88 (s, 1H), 4.89 (t, 1H, J=5.0 Hz), 4.85 (s, 2H), 4.31 (d, 2H, J=5.0 Hz), 3.91 (t, 2H, J=5.5 Hz), 3.59 (s, 3H), 3.48 (s, 2H), 3.04 (s, 6H), 2.77 (t, 2H, J=5.5 Hz), 2.34 (s, 3H); MS (ESI+) m/z 540.3 (M+H).

Example 124

Example 124

5-(Dimethylamino)-2-(2-(hydroxymethyl)-3-(1-methyl-6-oxo-5-(pyrimidin-4-ylamino)-1,6-dihydropyridin-3-yl)phenyl)isoindolin-1-one 124

Using the same general procedure as described for the preparation of 104, reaction of 123e (400 mg, 0.890 mmol) with 107a (207 mg, 0.740 mmol) followed by a hydrolysis gave a 28% yield (120 mg) of 124 as a white solid: mp 206-208° C.; $^1$H NMR (500 MHz, DMSO-$d_6$) δ 9.17 (s, 1H), 8.73 (d, 1H, J=2.0 Hz), 8.65 (s, 1H), 8.30 (d, 1H, J=6.0 Hz), 7.57 (d, 1H, J=8.5 Hz), 7.55 (d, 1H, J=2.5 Hz), 7.49 (t, 1H, J=2.5 Hz), 7.43 (dd, 1H, J=8.0, 1.5 Hz), 7.37 (dd, 1H, J=8.0, 1.5 Hz), 7.31 (dd, 1H, J=6.0, 1.5 Hz), 6.88-6.85 (m, 2H), 4.94 (t, 1H, J=4.5 Hz), 4.86 (s, 2H), 4.32 (d, 2H, J=4.5 Hz), 3.61 (s, 3H), 3.04 (s, 6H); MS (ESI+) m/z 483.2 (M+H).

Example 125

Example 125a

Methyl 4-(Bromomethyl)-2-tert-butylthiazole-5-carboxylate 125a

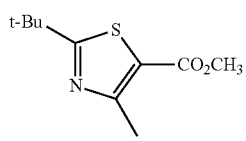

Using the same general procedure as described for the preparation of 102e, reaction of methyl 4-methyl-2-tert-butylthiazole-5-carboxylate with N-bromo-succinimide in carbon tetrachloride afforded 125a.

Example 125b 2-(tert-Butyldimethylsilyloxy)methyl)-3-(4,4,5,5-tetramethyl-1,3,2-dioxaborolan-2-yl)aniline 125b Using the same general procedure as described for the preparation of 101f, reaction of 125a with 4,4,4',4',5,5,5',5'-octamethyl-2,2'-bi(1,3,2-dioxaborolane) afforded 125b.

Example 125c

Methyl 2-tert-Butyl-4-((2-((tert-butyldimethylsilyloxy)methyl)-3-(4,4,5,5-tetramethyl-1,3,2-dioxaborolan-2-yl)phenylamino)methyl)thiazole-5-carboxylate 125c

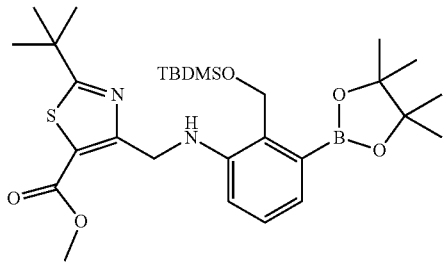 [SMILES: COC(=O)c1sc(C(C)(C)C)nc1CNc1cccc(B2OC(C)(C)C(C)(C)O2)c1CO[Si](C)(C)C(C)(C)C]

A suspension of 125a (1 g, 3.4 mmol), 2-((tert-butyldimethylsilyloxy)methyl)-3-(4,4,5,5-tetramethyl-1,3,2-dioxaborolan-2-yl)benzenamine (125b) (1.1 g, 3.1 mmol) and cesium carbonate (1.3 g, 4.1 mmol) in acetonitrile (30 mL) was stirred at 45° C. overnight. The reaction mixture was filtered and the filtrate was concentrated at reduced pressure. The residue was purified on silica gel eluting with 0 to 1% EtOAc in petroleum ether to afford 125c as yellow oil (1.1 g, 56%). LCMS: (M+H)$^+$ 575.

Example 125d

Methyl 2-tert-Butyl-5-((2-((tert-butyldimethylsilyloxy)methyl)-3-(1-methyl-6-oxo-5-(pyrimidin-4-ylamino)-1,6-dihydropyridin-3-yl)phenylamino)methyl)thiazole-4-carboxylate 125d

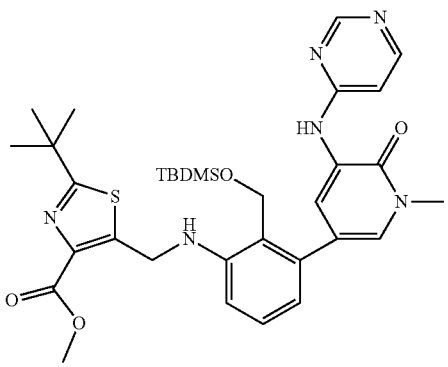 [SMILES: COC(=O)c1nc(C(C)(C)C)sc1CNc1cccc(-c2cc(Nc3ccncn3)c(=O)n(C)c2)c1CO[Si](C)(C)C(C)(C)C]

A flask was charged with 107a (379 mg, 1.3 mmol), methyl 2-tert-butyl-4-(2-((tert-butyldimethylsilyloxy)methyl)-3-(4,4,5,5-tetramethyl-1,3,2-dioxaborolan-2-yl)-phenylamino)methyl)thiazole-5-carboxylate (125c) (775 mg, 1.3 mmol), PdCl$_2$(dppf) (266 mg, 0.32 mmol), 1.0 M of K$_3$PO$_4$.3H$_2$O (2.6 ml), 1.0 M of NaOAc (2.6 mL) and 40 mL of MeCN. The mixture was stirred at 110° C. under nitrogen for 16 h. After flash column purification with petroleum ether/ethyl acetate (6:1) as eluent, 125d was obtained as white solid (0.6 g, 69%). LCMS: (M+H)$^+$ 649.

Example 125e 2-tert-butyl-5-((2-((tert-butyldimethylsilyloxy)methyl)-3-(1-methyl-6-oxo-5-(pyrimidin-4-ylamino)-1,6-dihydropyridin-3-yl)phenylamino)methyl)thiazole-4-carboxylic acid 125e

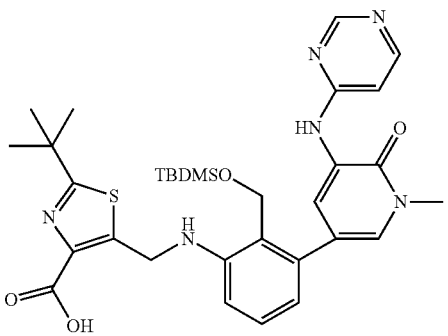 [SMILES: Cn1cc(-c2cccc(NCc3sc(C(C)(C)C)nc3C(=O)O)c2CO[Si](C)(C)C(C)(C)C)cc(Nc2ccncn2)c1=O]

A mixture of methyl 2-tert-butyl-5-((2-((tert-butyldimethylsilyloxy)methyl)-3-(1-methyl-6-oxo-5-(pyrimidin-4-ylamino)-1,6-dihydropyridin-3-yl)phenylamino)-methyl)thiazole-4-carboxylate (125d) (590 mg, 0.9 mmol) and lithium hydroxide (1090 mg, 45 mmol) in isopropyl alcohol (20 mL) and water (20 mL) was stirred at 25° C. for 5 h. The reaction mixture was concentrated to about 50% of the original volume and acidified to pH~4 with 1M HCl (aq.). It was then extracted with CH$_2$Cl$_2$:MeOH(~7:1). The organic layers were combined, dried with anhydrous MgSO$_4$, and concentrated to afford 125e, which was used in the next step without further purification. LCMS: (M+H)$^+$ 635.

Example 125

2-tert-Butyl-5-(2-(hydroxymethyl)-3-(1-methyl-6-oxo-5-(pyrimidin-4-ylamino)-1,6-dihydropyridin-3-yl)phenyl)-4,5-dihydropyrrolo[3,4-d]thiazol-6-one 125

To a solution of 2-tert-butyl-5-((2-((tert-butyldimethylsilyloxy)methyl)-3-(1-methyl-6-oxo-5-(pyrimidin-4-ylamino)-1,6-dihydropyridin-3-yl)phenylamino)-methyl)thiazole-4-carboxylic acid (125e) (500 mg, 0.78 mmol) in methylene chloride (40 mL) was added N,N-Diisopropylethylamine (503 mg, 3.9 mmol) and N,N,N',N'-tetramethyl-O-(7-azabenzotriazol-1-yl)uronium hexafluorophosphate (900 mg, 2.37 mmol). The mixture was stirred at 25° C. for 2 h. After flash column purification with PE:EA (1:3 to 1:6) as eluent, 125 was obtained as white solid (32 mg, 10%). LCMS: (M+H)$^+$ 503. $^1$H NMR (500 MHz, MeOD) ppm 8.84 (d, J=2 Hz, 1H), 8.66 (s, 1 H), 8.29 (d, J=5.5 Hz, 1H), 7.49-7.56 (m, 4 H), 7.09 (d, J=5.5 Hz, 2 H), 5.04 (s, 2 H), 4.57 (s, 2 H), 3.73 (s, 3 H), 1.54 (s, 9 H).

Example 126

Example 126a tert-Butyl 5-Amino-3-cyclopropyl-1H-pyrazole-1-carboxylate 126a

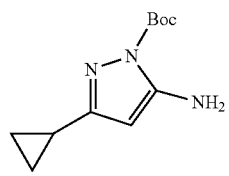 [SMILES: CC(C)(C)OC(=O)n1nc(C2CC2)cc1N]

To a mixture of 3-cyclopropyl-1H-pyrazol-5-amine (0.25 g, 2 mmol) and K$_2$CO$_3$ (0.828 g, 6 mmol) in THF (5 mL) was added (Boc)$_2$O (0.436 g, 2 mmol) in THF (5 mL). The reaction mixture was stirred at room temperature for 15 h. It was then filtered and concentrated. The residue was purified by flash column eluting with 6:1 petroleum ether/ethyl acetate to afford 126a as a white solid (240 mg, 54%).
LCMS: (M-Boc)$^+$ 124.

Example 126b

5-Bromo-3-(3-cyclopropyl-1H-pyrazol-5-ylamino)-1-methylpyridin-2(1H)-one 126b

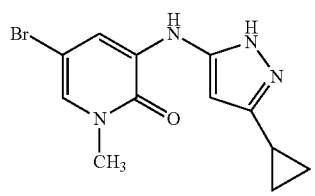

A 100-mL single-neck round-bottomed flask equipped with a magnetic stirrer and reflux condenser was charged with 1,4-dioxane (15 mL), tert-butyl 5-amino-3-cyclopropyl-1H-pyrazole-1-carboxylate (126a) (455 mg, 1.95 mmol), 3,5-dibromo-1-methylpyridin-2(1H)-one (0.40 g, 1.5 mmol), and cesium carbonate (1.22 g, 3.75 mmol). After bubbling nitrogen through the resulting mixture for 30 minutes, XantPhos (87 mg, 0.15 mmol) and tris(dibenzylideneacetone)dipalladium(0) (70 mg, 0.075 mmol) were added, and the reaction mixture was heated at reflux for 15 h. After this time the reaction was cooled to room temperature, partitioned between ethyl acetate (30 mL) and water (30 mL). The aqueous layer was separated and extracted with ethyl acetate (50 mL×2). The organic layers were combined, washed with brine (50 mL) and dried over sodium sulfate. The drying agent was removed by filtration and the filtrate was concentrated under reduced pressure. The residue was purified on flash column eluting with 50:1 DCM/MeOH to afford 126b as a yellow solid (320 mg, 50%). LCMS: (M+H)$^+$ 309.

¹H NMR (500 MHz, DMSO) δ 11.85 (s, 1H), 8.23 (s, 1H), 8.02 (d, J=2.5, 1H), 7.35 (d, J=2.5, 1H), 5.77 (d, J=2, 1H), 3.46 (s, 3H), 1.83 (m, 1H), 0.90 (m, 2H), 0.64 (m, 2H)

Example 126c

Methyl 2-tert-Butyl-5-((2-(((tert-butyldimethylsilyloxy)methyl)-3-(5-(3-cyclopropyl-1H-pyrazol-5-ylamino)-1-methyl-6-oxo-1,6-dihydropyridin-3-yl)phenylamino)methyl)thiazole-4-carboxylate 125c

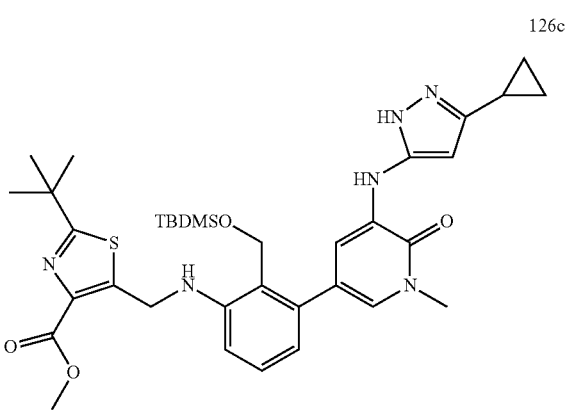 [SMILES: COC(=O)c1nc(C(C)(C)C)sc1CNc1cccc(-c2cc(Nc3cc(C4CC4)n[nH]3)c(=O)n(C)c2)c1CO[Si](C)(C)C(C)(C)C]

Following the procedures as described for compound 125d and starting with 1.7 g of methyl 2-tert-butyl-4-((2-(((tert-butyldimethylsilyloxy)methyl)-3-(4,4,5,5-tetramethyl-1,3,2-dioxaborolan-2-yl)phenylamino)methyl)thiazole-5-carboxylate (125c) and 0.9 g of 5-bromo-3-(3-cyclopropyl-1H-pyrazol-5-ylamino)-1-methyl-1pyridin-2(1H)-one(126b), 126c was obtained as a yellow solid (0.8 g, 40%).
LCMS: (M+H)⁺ 677.

Example 126d 2-tert-Butyl-5-((2-(((tert-butyldimethylsilyloxy)methyl)-3-(5-(3-cyclopropyl-1H-pyrazol-5-ylamino)-1-methyl-6-oxo-1,6-dihydropyridin-3-yl)phenylamino)methyl)thiazole-4-carboxylic acid 126d

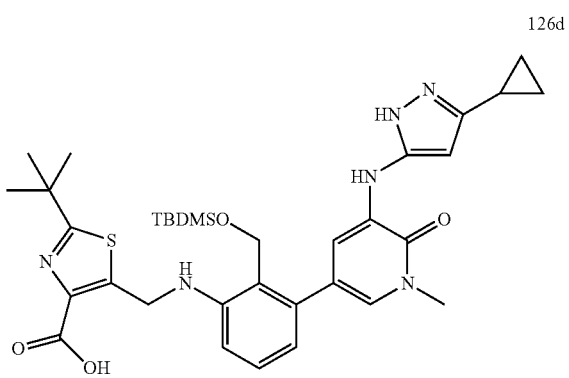 [SMILES: Cn1cc(-c2cccc(NCc3sc(C(C)(C)C)nc3C(=O)O)c2CO[Si](C)(C)C(C)(C)C)cc(Nc2cc(C3CC3)n[nH]2)c1=O]

Following the procedures as described for compound 125e and starting with methyl 2-tert-butyl-5-((2-(((tert-butyldimethylsilyloxy)methyl)-3-(5-(3-cyclopropyl-1H-pyrazol-5-ylamino)-1-methyl-6-oxo-1,6-dihydropyridin-3-yl)phenylamino)-methyl)thiazole-4-carboxylate, 125d was obtained as a yellow solid (crude). LCMS: (M+H)⁺ 663.

Example 126

2-tert-butyl-5-(3-(5-(5-cyclopropyl-1H-pyrazol-3-ylamino)-1-methyl-6-oxo-1,6-dihydropyridin-3-yl)-2-(hydroxymethyl)phenyl)-4H-pyrrolo[3,4-d]thiazol-6(5H)-one 126

Following the procedures in Example 125 and starting with 125d, 126 was obtained as a white solid (30 mg, 5%, three steps). LCMS: (M+H)⁺ 531. ¹H NMR (500 MHz, MeOD) ppm 7.75 (d, J=1.5 Hz, 1H), 7.51 (m, 3 H), 7.21 (s, 1H), 5.80 (s, 1 H), 5.03 (d, J=10 Hz, 2H), 4.54 (s, 1 H), 4.57 (s, 2 H), 3.70 (s, 3 H), 1.88 (m, 1 H), 1.55 (s, 3 H), 0.97 (d, J=7.5 Hz, 2 H), 0.73 (m, 2 H).

Example 901

Biochemical Btk Assay

A generalized procedure for a standard biochemical Btk Kinase Assay that can be used to test Formula I compounds is as follows. A master mix minus Btk enzyme is prepared containing 1× Cell Signaling kinase buffer (25 mM Tris-HCl, pH 7.5, 5 mM beta-glycerophosphate, 2 mM dithiothreitol, 0.1 mM $Na_3VO_4$, 10 mM $MgCl_2$), 0.5 μM Promega PTK Biotinylated peptide substrate 2, and 0.01% BSA. A master mix plus Btk enzyme is prepared containing 1× Cell Signaling kinase buffer, 0.5 μM PTK Biotinylated peptide substrate 2, 0.01% BSA, and 100 ng/well (0.06 mU/well) Btk enzyme. Btk enzyme is prepared as follows: full length human wild-type Btk (accession number NM-000061) with a C-terminal V5 and 6×His tag was subcloned into pFastBac vector for making baculovirus carrying this epitope-tagged Btk. Generation of baculovirus is done based on Invitrogen's instructions detailed in its published protocol "Bac-to-Bac Baculovirus Expression Systems" (Cat. Nos. 10359-016 and 10608-016). Passage 3 virus is used to infect Sf9 cells to overexpress the recombinant Btk protein. The Btk protein is then purified to homogeneity using Ni-NTA column. The purity of the final protein preparation is greater than 95% based on the sensitive Sypro-Ruby staining. A solution of 200 μM ATP is prepared in water and adjusted to pH7.4 with 1N NaOH. A quantity of 1.25 μL of compounds in 5% DMSO is transferred to a 96-well ½ area Costar polystyrene plate. Compounds are tested singly and with an 11-point dose-responsive curve (starting concentration is 10 μM; 1:2 dilution). A quantity of 18.75 μL of master mix minus enzyme (as a negative control) and master mix plus enzyme is transferred to appropriate wells in 96-well ½ area costar polystyrene plate. 5 μL of 200 μM ATP is added to that mixture in the 96-well ½ area Costar polystyrene plate for final ATP concentration of 40 μM. The reaction is allowed to incubate for 1 hour at room temperature. The reaction is stopped with Perkin Elmer 1× detection buffer containing 30 mM EDTA, 20 nM SA-APC, and 1 nM PT66 Ab. The plate is read using time-resolved fluorescence with a Perkin Elmer Envision using excitation filter 330 nm, emission filter 665 nm, and $2^{nd}$ emission filter 615 nm. $IC_{50}$ values are subsequently calculated. Alternatively, the Lanthascreen assay can be used to evaluate Btk activity through quantification of its phosphorylated peptide product. The FRET (Fluorescence Resonance Energy Transfer) that occurs between the fluorescein on the peptide product and the terbium on the detection antibody decreases with the addition of inhibitors of Btk that reduce the phosphorylation of the peptide. In a final reaction volume of 25 uL, Btk (h) (0.1 ng/25 ul reaction) is incubated with 50 mM Hepes pH 7.5, 10 mM MgCl$_2$, 2 mM MnCl$_2$, 2 mM DTT, 0.2 mM NaVO4, 0.01% BSA, and 0.4 uM fluorescein poly-GAT. The reaction is initiated by the addition of ATP to 25 uM (Km of ATP). After incubation for 60 minutes at room temperature, the reaction is stopped by the addition of a final concentration of 2 nM Tb-PY20 detection antibody in 60 mM EDTA for 30 minutes at room temperature. Detection is determined on a Perkin Elmer Envision with 340 nM excitation and emission at 495 nm and 520 nm. Exemplary Btk inhibition IC50 values are in Tables and 2.

Example 902

Ramos Cell Btk Assay

Another generalized procedure for a standard cellular Btk Kinase Assay that can be used to test Formula I compounds is as follows. Ramos cells are incubated at a density of $0.5 \times 10^7$ cells/ml in the presence of test compound for 1 hr at 37° C. Cells are then stimulated by incubating with 10 µg/ml anti-human IgM F(ab)$_2$ for 5 minutes at 37° C. Cells are pelleted, lysed, and a protein assay is performed on the cleared lysate. Equal protein amounts of each sample are subject to SDS-PAGE and western blotting with either anti-phosphoBtk (Tyr223) antibody (Cell Signaling Technology #3531; Epitomics, cat. #2207-1) or phosphoBtk(Tyr551) antibody (BD Transduction Labs #558034) to assess Btk autophosphorylation or an anti-Btk antibody (BD Transduction Labs #611116) to control for total amounts of Btk in each lysate.

Example 903

B-Cell Proliferation Assay

A generalized procedure for a standard cellular B-cell proliferation assay that can be used to test Formula I compounds is as follows. B-cells are purified from spleens of 8-16 week old Balb/c mice using a B-cell isolation kit (Miltenyi Biotech, Cat #130-090-862). Testing compounds are diluted in 0.25% DMSO and incubated with $2.5 \times 10^5$ purified mouse splenic B-cells for 30 min prior to addition of 10 µg/ml of an anti-mouse IgM antibody (Southern Biotechnology Associates Cat #1022-01) in a final volume of 100 µl. Following 24 hr incubation, 1 µCi $^3$H-thymidine is added and plates are incubated an additional 36 hr prior to harvest using the manufacturer's protocol for SPA[$^3$H] thymidine uptake assay system (Amersham Biosciences #RPNQ 0130). SPA-bead based fluorescence is counted in a microbeta counter (Wallace Triplex 1450, Perkin Elmer).

Example 904

T Cell Proliferation Assay

A generalized procedure for a standard T cell proliferation assay that can be used to test Formula I compounds is as follows. T cells are purified from spleens of 8-16 week old Balb/c mice using a Pan T cell isolation kit (Miltenyi Biotech, Cat #130-090-861). Testing compounds are diluted in 0.25% DMSO and incubated with $2.5 \times 10^5$ purified mouse splenic T cells in a final volume of 100 µl in flat clear bottom plates precoated for 90 min at 37° C. with 10 µg/ml each of anti-CD3 (BD #553057) and anti-CD28 (BD #553294) antibodies. Following 24 hr incubation, 1 µCi $^3$H-thymidine is added and plates incubated an additional 36 hr prior to harvest using the manufacturer's protocol for SPA[$^3$H] thymidine uptake assay system (Amersham Biosciences #RPNQ 0130). SPA-bead based fluorescence was counted in a microbeta counter (Wallace Triplex 1450, Perkin Elmer).

Example 905

CD86 Inhibition Assay

A generalized procedure for a standard assay for the inhibition of B cell activity that can be used to test Formula I compounds is as follows. Total mouse splenocytes are purified from spleens of 8-16 week old Balb/c mice by red blood cell lysis (BD Pharmingen #555899). Testing compounds are diluted to 0.5% DMSO and incubated with $1.25 \times 10^6$ splenocytes in a final volume of 200 µl in flat clear bottom plates (Falcon 353072) for 60 min at 37° C. Cells are then stimulated with the addition of 15 µg/ml IgM (Jackson ImmunoResearch 115-006-020), and incubated for 24 hr at 37° C., 5% CO$_2$. Following the 24 hr incubation, cells are transferred to conical bottom clear 96-well plates and pelleted by centrifugation at 1200×g×5 min. Cells are preblocked by CD16/CD32 (BD Pharmingen #553142), followed by triple staining with CD19-FITC (BD Pharmingen #553785), CD86-PE (BD Pharmingen #553692), and 7AAD (BD Pharmingen #51-68981E). Cells are sorted on a BD FACSCalibur and gated on the CD19$^+$/7AAD$^-$ population. The levels of CD86 surface expression on the gated population is measured versus test compound concentration. Exemplary results are in Table 3.

TABLE 3

| Compound | CD86 inhibition EC$_{50}$ (µM) |
| --- | --- |
| 107 | 0.074 |
| 109 | 0.113 |
| 117 | 0.154 |
| 127 | 0.498 |
| 134 | 1.9 |
| 141 | 0.775 |
| 146 | 0.0289 |
| 152 | 0.306 |
| 154 | 0.149 |
| 157 | 0.2289 |
| 160 | 0.153 |

Example 906

B-ALL Cell Survival Assay

The following is a procedure for a standard B-ALL (acute lymphoblastic leukemia) cell survival study using an XTT readout to measure the number of viable cells. This assay can be used to test Formula I compounds for their ability to inhibit the survival of B-ALL cells in culture. One human B-cell acute lymphoblastic leukemia line that can be used is SUP-B 15, a human Pre-B-cell ALL line that is available from the ATCC.

SUP-B 15 pre-B-ALL cells are plated in multiple 96-well microtiter plates in 100 µl of Iscove's media+20% FBS at a concentration of $5 \times 10^5$ cells/ml. Test compounds are then added with a final conc. of 0.4% DMSO. Cells are incubated at 37° C. with 5% CO$_2$ for up to 3 days. After 3 days cells are split 1:3 into fresh 96-well plates containing the test compound and allowed to grow up to an additional 3 days. After each 24 h period, 50 ul of an XTT solution is added to one of the replicate 96-well plates and absorbance readings are taken at 2, 4 and 20 hours following manufacturer's directions. The reading taken with an OD for DMSO only treated cells within the linear range of the assay (0.5-1.5) is then taken and the percentage of viable cells in the compound treated wells are measured versus the DMSO only treated cells.

Example 907

CD69 Whole Blood Assay

Human blood is obtained from healthy volunteers, with the following restrictions: 1 week drug-free, non-smokers. Blood (approximately 20 mls to test 8 compounds) is collected by venipuncture into Vacutainer® (Becton, Dickinson and Co.) tubes with sodium heparin.

Solutions of Formula I compounds at 10 mM in DMSO are diluted 1:10 in 100% DMSO, then are diluted by three-fold serial dilutions in 100% DMSO for a ten point dose-response curve. The compounds are further diluted 1:10 in PBS and then an aliquot of 5.5 µl of each compound is added in duplicate to a 2 ml 96-well plate; 5.5 µl of 10% DMSO in PBS is added as control and no-stimulus wells. Human whole blood—HWB (100 µl) is added to each well. After mixing the plates are incubated at 37° C., 5% $CO_2$, 100% humidity for 30 minutes. Goat F(ab')2 anti-human IgM (10 µl of a 500 µg/ml solution, 50 µg/ml final) is added to each well (except the no-stimulus wells) with mixing and the plates are incubated for an additional 20 hours. At the end of the 20 hour incubation, samples are incubated with fluorescent labeled antibodies for 30 minutes, at 37° C., 5% $CO_2$, 100% humidity. Include induced control, unstained and single stains for compensation adjustments and initial voltage settings. Samples are then lysed with PharM Lyse™ (BD Biosciences Pharmingen) according to the manufacturer's instructions. Samples are then transferred to a 96 well plate suitable to be run on the BD Biosciences HTS 96 well system on the LSRII machine. Data acquired and Mean Fluorescence Intensity values were obtained using BD Biosciences DIVA Software. Results are initially analyzed by FACS analysis software (Flow Jo). The IC50 for test compounds is defined as the concentration which decreases by 50% the percent positive of CD69 cells that are also CD20 positive stimulated by anti-IgM (average of 8 control wells, after subtraction of the average of 8 wells for the no-stimulus background). The IC50 values are calculated by Prism version 5, using a nonlinear regression curve fit.

Exemplary IC50 values of selected compounds from Tables 1 and 2 in the CD69 Whole Blood Assay include:

TABLE 4

| Compound No. | IC50 (micromolar) |
|---|---|
| 107 | 0.605 |
| 110 | 1.1 |
| 119 | 0.157 |
| 122 | 0.185 |
| 139 | 0.0426 |
| 148 | 0.193 |
| 151 | 0.112 |
| 160 | 0.116 |

We claim:
1. A compound selected from Formula I:

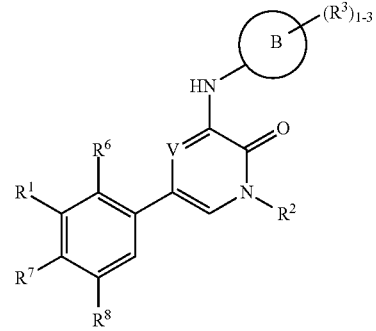

and stereoisomers, tautomers, or pharmaceutically acceptable salts thereof, wherein:
$R^1$ is selected from:

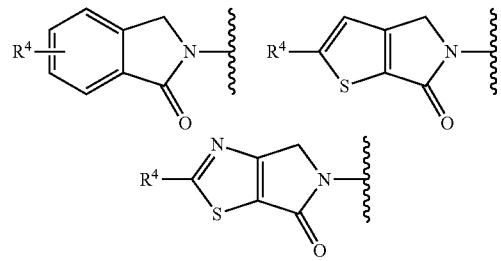

where the wavy line indicates the site of attachment;
$R^4$ is selected from OH, CN, $NR^bR^c$, piperidinyl, $C_3$-$C_6$ cycloalkyl optionally substituted with $C_1$-$C_6$ alkyl or $C_1$-$C_4$ haloalkyl, and $C_1$-$C_6$ alkyl optionally substituted with OH or $OC_1$-$C_4$ alkyl;
$R^2$ is H, $CH_3$ or $CF_3$;
ring B is selected from phenyl, 5-6 membered heteroaryl having at least one nitrogen ring atom, and 8-11 membered heterocyclyl having at least one nitrogen ring atom;
$R^3$ is independently selected from H, —$R^a$, —$OR^b$, —$SR^b$, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$; or two adjacent $R^3$ groups are optionally taken together to form a 5-6 membered ring having 0-2 heteroatoms selected from O, S or N, wherein said 5-6 membered ring is fused to ring B;
$R^a$ is $C_1$-$C_6$ alkyl, cycloalkyl, heterocycloalkyl, aryl, or heteroaryl, wherein each member of $R^a$ is optionally substituted with one to three $R^{11}$ groups;
$R^b$ is H, $C_1$-$C_6$ alkyl, cycloalkyl, heterocycloalkyl, aryl, or heteroaryl, wherein each member of $R^b$ except H is optionally substituted with one to three $R^{11}$ groups;
$R^c$ is H or $C_1$-$C_4$ alkyl optionally substituted with one or three $R^{11}$ groups; or $R^b$ and $R^c$, and the nitrogen to which they are attached, form an optionally substituted heterocycloalkyl group;
each $R^{11}$ is independently selected from $C_1$-$C_4$ alkyl, cycloalkyl, heterocycloalkyl, aryl, heteroaryl, aryl-$C_1$-

C₄ alkyl-, heteroaryl-C₁-C₄ alkyl-, cycloalkyl-C₁-C₄ alkyl-, heterocycloalkyl-C₁-C₄ alkyl-, C₁-C₄ haloalkyl-, —OC₁-C₄ alkyl, —O-heterocycloalkyl, —OC₁-C₄ alkylphenyl, —C₁-C₄ alkyl-OH, —OC₁-C₄ haloalkyl, halo, —OH, —NH₂, —C₁-C₄ alkyl-NH₂, —NH(C₁-C₄ alkyl), —N(C₁-C₄ alkyl)(C₁-C₄ alkyl), —N(C₁-C₄ alkyl)(C₁-C₄ alkylphenyl), —NH(C₁-C₄ alkylphenyl), cyano, nitro, oxo, —CO₂H, —C(O)OC₁-C₄ alkyl, —CON(C₁-C₄ alkyl)(C₁-C₄ alkyl), —CONH(C₁-C₄ alkyl), —CONH₂, —NHC(O)(C₁-C₄ alkyl), —NHC(O)(phenyl), —N(C₁-C₄ alkyl)C(O)(C₁-C₄ alkyl), —N(C₁-C₄ alkyl)C(O)(phenyl), —C(O)C₁-C₄ alkyl, —C(O)C₁-C₄ phenyl, —C(O)C₁-C₄ haloalkyl, —OC(O)C₁-C₄ alkyl, —SO₂(C₁-C₄ alkyl), —SO₂(phenyl), —SO₂(C₁-C₄ haloalkyl), —SO₂NH₂, —SO₂NH(C₁-C₄ alkyl), —SO₂NH(phenyl), —NHSO₂(C₁-C₄ alkyl), —NHSO₂(phenyl), and —NHSO₂(C₁-C₄ haloalkyl);

R⁵ is H or F;

R⁶ is H, CH₃, F, Cl, CN, OCH₃, OH, or methyl substituted with OH, OCH₃ or one or more halo groups;

R⁷ is H, CH₃, F, Cl, CN or OCH₃;

R⁸ is H, CH₃, CF₃, F, Cl, CN or OCH₃;

V is CH or N;

each R⁹ is independently C₁-C₃ alkyl; and each R¹⁰ is independently H or CH₃.

2. The compound of claim 1 wherein R² is H or CH₃.

3. The compound of claim 1 wherein R³ is H, —Rᵃ, —NRᵇRᶜ or —C(O)Rᵇ.

4. The compound of claim 1 wherein R³ is selected from cyclopropyl, azetidinyl, morpholinyl, piperidinyl, oxopiperidinyl, piperazinyl, and oxopiperazinyl, optionally substituted with F, OH, CH₃, or COCH₃.

5. The compound of claim 1 wherein R³ is:

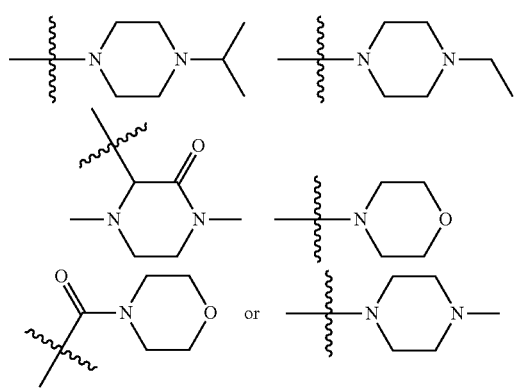

where the wavy line indicates the site of attachment.

6. The compound of claim 1 wherein R⁴ is H, t-butyl, N-pyrrolidinyl, N-piperidinyl, N-azepanyl, 2-hydroxy-2-methylpropyl, prop-1-en-2-yl, —N(CH₃)Et, i-propyl, cyclopentyl, cyclohexyl, 3-methylbutan-2-yl, —N(CH₃)(i-Pr), or —NH(cyclopropyl).

7. The compound of claim 1 wherein R⁵ is H or F.

8. The compound of claim 1 wherein R⁶ is H, CH₃, F, or CH₂OH.

9. The compound of claim 1 wherein R⁷ is H or F.

10. The compound of claim 1 wherein B is pyrazolo[1,5-a]pyrazin-2-yl, pyrazol-3-yl, pyrimidin-4-yl, or pyridin-2-yl.

11. The compound of claim 1 wherein:

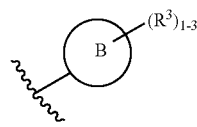

is selected from the structures:

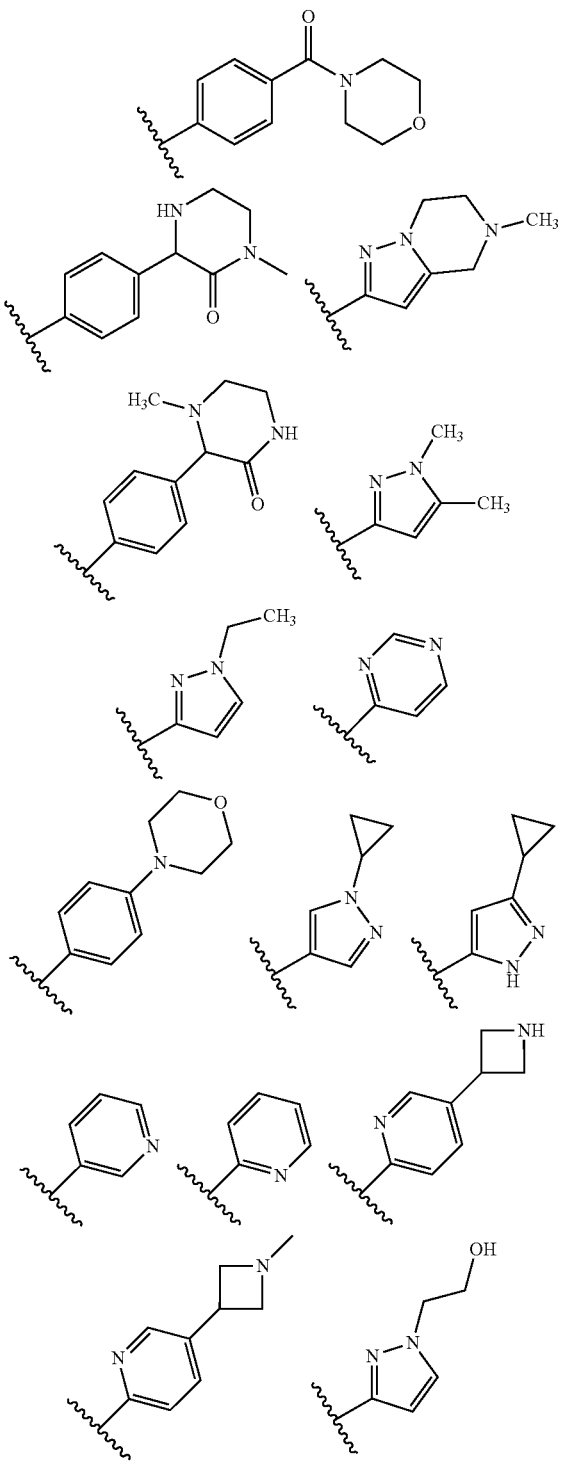

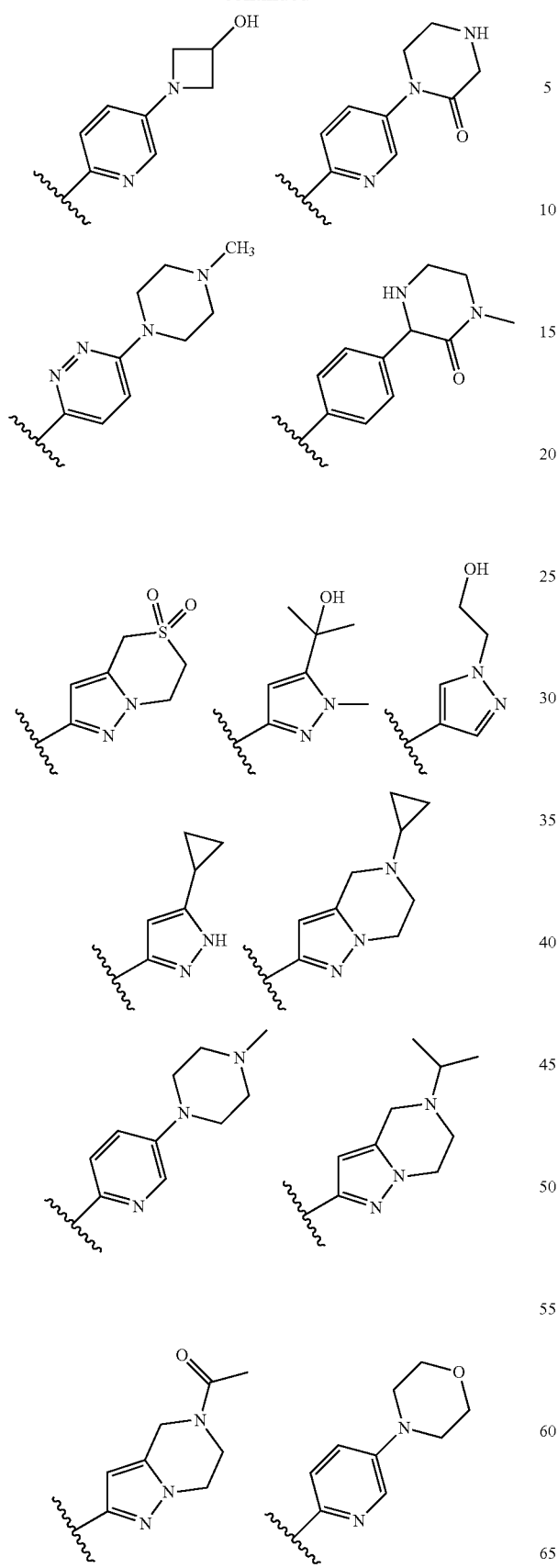
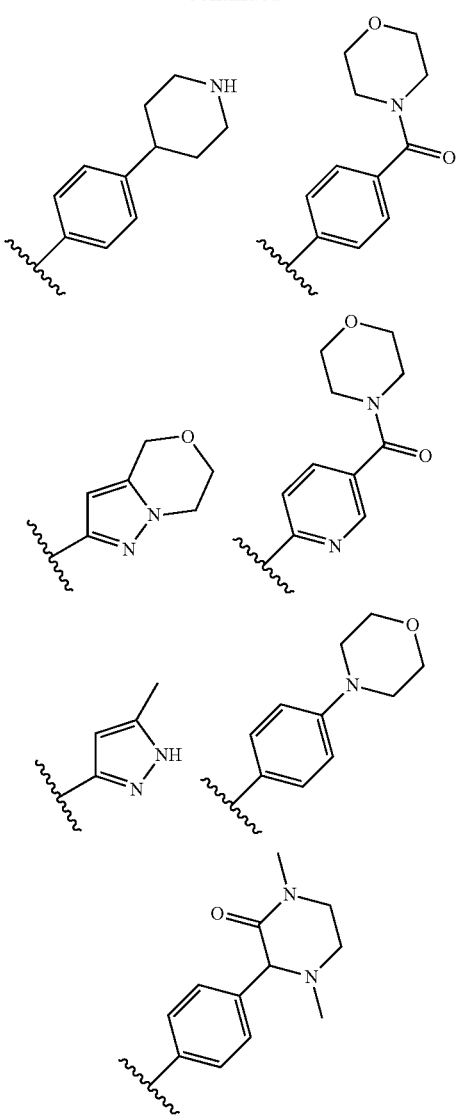
where the wavy line indicates the site of attachment.
12. The compound of claim 1 having the structure of Formula Ia:
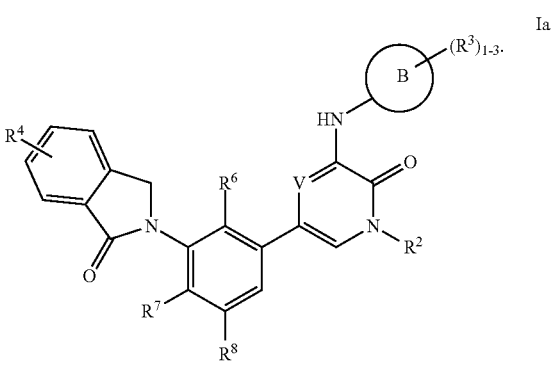

13. The compound of claim 1 having the structure of Formula Ib:

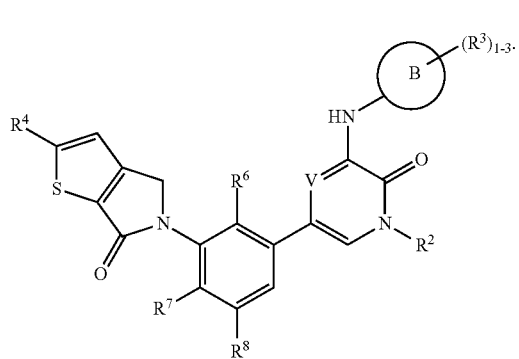

14. The compound of claim 1 having the structure of Formula Ic:

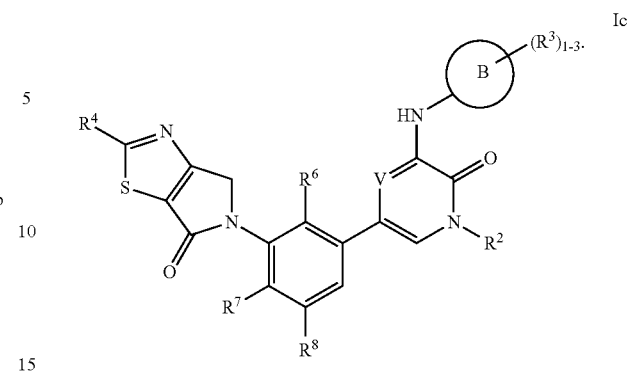

15. The compound of claim 1 chosen from Table 1.
16. The compound of claim 1 chosen from Table 2.
17. A pharmaceutical composition comprised of a compound of claim 1 and a pharmaceutically acceptable carrier, glidant, diluent, or excipient.
18. The pharmaceutical composition according to claim 17, further comprising a second therapeutic agent.
19. A kit for treating a condition mediated by Bruton's tyrosine kinase, comprising:
  a) a first pharmaceutical composition comprising a compound of claim 1; and
  b) instructions for use.

* * * * *